(12) United States Patent
Yamniuk et al.

(10) Patent No.: US 11,220,550 B2
(45) Date of Patent: Jan. 11, 2022

(54) ANTAGONISTIC ANTI-CD40 ANTIBODIES AND METHODS OF ANTAGONIZING CD40 ACTIVITY

(71) Applicant: Bristol-Myers Squibb Company, Princeton, NJ (US)

(72) Inventors: Aaron Yamniuk, Lawrenceville, NJ (US); Mary Struthers, Edison, NJ (US); Suzanne J. Suchard, Portland, OR (US)

(73) Assignee: Bristol-Myers Squibb Company, Princeton, NJ (US)

( * ) Notice: Subject to any disclaimer, the term of this patent is extended or adjusted under 35 U.S.C. 154(b) by 377 days.

(21) Appl. No.: 15/988,554

(22) Filed: May 24, 2018

(65) Prior Publication Data

US 2018/0340031 A1  Nov. 29, 2018

Related U.S. Application Data

(60) Provisional application No. 62/511,079, filed on May 25, 2017.

(51) Int. Cl.
*A61K 39/395* (2006.01)
*C07K 16/28* (2006.01)

(52) U.S. Cl.
CPC ........ *C07K 16/2887* (2013.01); *A61K 39/395* (2013.01); *C07K 16/28* (2013.01); *C07K 2317/30* (2013.01); *C07K 2317/51* (2013.01); *C07K 2317/52* (2013.01); *C07K 2317/565* (2013.01); *C07K 2317/71* (2013.01); *C07K 2317/73* (2013.01); *C07K 2317/732* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,530,101 | A | 6/1996 | Queen et al. |
| 5,585,089 | A | 12/1996 | Queen et al. |
| 5,693,762 | A | 12/1997 | Queen et al. |
| 6,180,370 | B1 | 1/2001 | Queen et al. |
| 6,687,673 | B2 | 2/2004 | Mann |
| 6,737,056 | B1 | 5/2004 | Presta |
| 7,183,387 | B1 | 2/2007 | Presta |
| 8,674,083 | B2 | 3/2014 | Presta |
| 9,090,696 | B2 | 7/2015 | Barrett et al. |
| 9,475,879 | B2 | 10/2016 | Suri et al. |
| 10,435,475 | B2 | 10/2019 | Honczarenko et al. |
| 2005/0054832 | A1 | 3/2005 | Lazar et al. |
| 2006/0235208 | A1 | 10/2006 | Lazar et al. |
| 2007/0003546 | A1 | 1/2007 | Lazar et al. |
| 2008/0199471 | A1 | 8/2008 | Bernett et al. |
| 2013/0209445 | A1 | 8/2013 | Lazar et al. |
| 2014/0079701 | A1* | 3/2014 | Miller ............... C07K 16/241 424/135.1 |
| 2014/0099317 | A1 | 4/2014 | Suri et al. |
| 2014/0335089 | A1* | 11/2014 | Igawa ............... A61P 35/00 424/136.1 |
| 2014/0363428 | A1 | 12/2014 | Igawa et al. |
| 2015/0018529 | A1* | 1/2015 | Humphreys ......... C07K 16/468 530/387.3 |
| 2015/0210763 | A1 | 7/2015 | Kuramochi et al. |
| 2015/0299296 | A1 | 10/2015 | Katada et al. |
| 2015/0315284 | A1 | 11/2015 | Lazar et al. |
| 2015/0337053 | A1 | 11/2015 | McCarthy et al. |
| 2016/0039912 | A1 | 2/2016 | Mimoto et al. |
| 2016/0075785 | A1* | 3/2016 | Ast ...................... C07K 16/32 424/136.1 |
| 2016/0355596 | A1 | 12/2016 | Honczarenko et al. |
| 2016/0376371 | A1 | 12/2016 | Ravetch et al. |
| 2020/0157233 | A1 | 5/2020 | Yamniuk et al. |

FOREIGN PATENT DOCUMENTS

| | | |
|---|---|---|
| EP | 2471813 B1 | 12/2014 |
| WO | WO-2004/099249 A2 | 11/2004 |
| WO | WO-2006/019447 A1 | 2/2006 |
| WO | WO-2008/091954 A2 | 7/2008 |
| WO | WO-2008/137475 A2 | 11/2008 |

(Continued)

OTHER PUBLICATIONS

"Study of HCD122 (Lucatumumab) and Bendamustine Combination Therapy in CD40+ Rituximab-Refractory Follicular Lymphoma," Clinical Trials Feeds, on the Internet at hypertext transfer protocol: clinicaltrialsfeeds.org/clinical-trials/show/NCT01275209 (last updated Jan. 11, 2011).

Adams, Andrew B., et al., 2005, "Development of a chimeric anti-CD40 monoclonal antibody that synergizes with LEA29Y to prolong islet allograft survival," *J. Immunol.* 174: 542-550.

Davies, Clare C., et al., "TRAF6 is required for TRAF2-dependent CD40 signal transduction in nonhemopoietic cells," *Mol. Cell Biol.* 25: 9806-19 (2005).

Cai, B., et al, "C☐terminal lysine processing of human immunoglobulin G2 heavy chain in vivo," *Biotechnol Bioeng.* Feb. 2011; 108(2):404-12, Abstract only.

Hoogenboom, Hennie R., et al., "Multi-subunit proteins on the surface of filamentous phage: methodologies for displaying antibody (Fab) heavy and light chains," *Nucleic Acids Res.* 1991, vol. 19, No. 15, pp. 4133-4137.

(Continued)

*Primary Examiner* — Phillip Gambel
(74) *Attorney, Agent, or Firm* — Faegre Drinker Biddle & Reath LLP

(57) ABSTRACT

The disclosure provides for antibodies that bind CD40, including a humanized antibody and a chimeric antibody with different Fc domains. The antibodies bind CD40 and do not exhibit CD40 agonist activity. The antibodies may comprise a modified IgG1 Fc domain, and exhibit minimal activation of immature dendritic cells. Compositions comprising antibodies, methods of use for treatment of diseases involving CD40 activity, and use in the preparation of a medicament for treatment of a disease involving CD40 activity are provided.

15 Claims, 8 Drawing Sheets

Specification includes a Sequence Listing.

(56) References Cited

FOREIGN PATENT DOCUMENTS

| WO | WO-2012/065950 A1 | 5/2012 |
|---|---|---|
| WO | WO-2012/145673 A1 | 10/2012 |
| WO | WO-2014/006217 A1 | 1/2014 |
| WO | WO-2014/184545 A2 | 11/2014 |
| WO | WO-2015/0134988 A1 | 9/2015 |
| WO | WO-2016/028810 A1 | 2/2016 |
| WO | WO-2016/196314 A1 | 12/2016 |
| WO | WO-2017/004006 A1 | 1/2017 |
| WO | WO-2017/059196 A2 | 4/2017 |
| WO | WO-2018/065389 A1 | 4/2018 |
| WO | WO-2018/169993 A1 | 9/2018 |
| WO | WO-2018/175279 A2 | 9/2018 |
| WO | WO-2018/217976 A1 | 11/2018 |
| WO | WO-2018/217988 A1 | 11/2018 |
| WO | WO-2018/217988 A9 | 11/2018 |
| WO | WO-2018/218056 A1 | 11/2018 |
| WO | WO-2020/106620 A1 | 5/2020 |
| WO | WO-2020/112781 A1 | 6/2020 |

OTHER PUBLICATIONS

Vonderheide, Robert H., et al., "Clinical Activity and Immune Modulation in Cancer Patients Treated with CP-870,893, a Novel CD40 Agonist Monoclonal Antibody," *J Clin Oncol.* 2007, 25(7): 876-883.

Mimoto, F., et al., "Engineered antibody Fc variant with selectively enhanced FcγRIIb binding over both FcγRIIaR131 and FcγRIIaH131," *Protein Engineering, Design and Selection* 2001, 26(10): 589-598.

Yamniuk, Aaron, et al., "Modified IgG1 Fc Domains and Anti-CD40 Domain Antibody Fusions Therewith," filed May 24, 2018 (PCT/US18/34330), 95 pages.

Vidarsson, Gestur, et al., "IgG Subclasses and allotypes: from structure to effector functions," Frontiers in Immunology, vol. 5, Oct. 20, 2014, pp. 1-17.

International Search Report and Written Opinion dated Jul. 24, 2018 for PCT/US2018/034330.

Ristov et al. (2018) "Characterization of the in vitro and in vivo properties of CFZ533, a blocking and non-depleting anti-CD40 monoclonal antibody," Am J Transplant. 18(12):2895-2904. [Epub May 24, 2018 1.

International Search Report dated Sep. 11, 2018 in International Application No. PCT/US2018/034315.

Written Opinion dated Sep. 11, 2018 in International Application No. PCT/US2018/034315.

International Preliminary Report on Patentability dated Dec. 5, 2019 in International Application No. PCT/US2018/034315.

International Preliminary Report on Patentability dated Dec. 5, 2019 in International Application No. PCT/US2018/034330.

International Preliminary Report on Patentability dated Jun. 3, 2021 in International Application No. PCT/US2019/062011.

International Search Report and the Written Opinion dated Apr. 9, 2020 in International Application No. PCT/US2019/062011.

\* cited by examiner

6B

ANTAGONISTIC ANTI-CD40 ANTIBODIES AND METHODS OF ANTAGONIZING CD40 ACTIVITY

CROSS REFERENCE TO RELATED APPLICATIONS

This application claims the benefit of U.S. Provisional Application No. 62/511,079 filed May 25, 2017, which is hereby incorporated in its entirety for all purposes.

SEQUENCE LISTING

The instant application contains a Sequence Listing which has been submitted electronically in ASCII format and is hereby incorporated by reference in its entirety. Said ASCII copy, created on May 23, 2018, is named 200896_0013_00_US_ST25.txt and is 186,723 bytes in size.

FIELD

The disclosure provides for antibodies that bind CD40, including a humanized antibody and a chimeric antibody with different Fc domains. The antibody polypeptides bind CD40 and do not exhibit CD40 agonist activity. The antibodies may comprise a modified IgG1 Fc domain, and exhibit minimal activation of immature dendritic cells. Compositions comprising antibodies, methods of use for treatment of diseases involving CD40 activity, and use in the preparation of a medicament for treatment of a disease involving CD40 activity are provided.

BACKGROUND

CD40 is a co-stimulatory molecule belonging to the tumor necrosis factor (TNF) receptor superfamily that is present on antigen presenting cells (APC), including dendritic cells, B cells, and macrophages. APCs are activated when CD40 binds its ligand, CD154 (CD40L), on $T_H$ cells. CD40-mediated APC activation is involved in a variety of immune responses, including cytokine production, up-regulation of co-stimulatory molecules (such as CD86), and enhanced antigen presentation and B cell proliferation. CD40 can also be expressed by endothelial cells, smooth muscle cells, fibroblasts, and epithelial cells.

CD40 activation is also involved in a variety of undesired T cell responses related to autoimmunity, transplant rejection, or allergic responses, for example. One strategy for controlling undesirable T cell responses is to target CD40 with an antagonistic antibody. For example, monoclonal antibody HCD122 (Lucatumumab), formerly known as Chiron 1212, is currently in clinical trials for the treatment of certain CD40-mediated inflammatory diseases. See "Study of HCD122 (Lucatumumab) and Bendamustine Combination Therapy in CD40+ Rituximab-Refractory Follicular Lymphoma," Clinical Trials Feeds, on the Internet at hypertext transfer protocol: clinicaltrialsfeeds.org/clinical-trials/show/NCT01275209 (last updated Jan. 11, 2011). Monoclonal antibodies, however, can display agonist activity. For example, the usefulness of the anti-CD40 antibody, Chi220, is limited by its weak stimulatory potential. See Adams, et al., "Development of a chimeric anti-CD40 monoclonal antibody that synergizes with LEA29Y to prolong islet allograft survival," *J. Immunol.* 174: 542-50 (2005).

SUMMARY

In a first embodiment, the present invention provides an isolated antibody, or antigen binding portion thereof, that specifically binds to human CD40, wherein the antibody comprises a heavy chain and a light chain, wherein said heavy chain comprises a CDR1 comprising GYTFTDLSMHW (SEQ ID NO: 1), a CDR2 comprising YITPSSGYTAYNQKFKG (SEQ ID NO: 2), a CDR3 comprising LILQRGAY (SEQ ID NO: 3); and said light chain comprises a CDR1 comprising RASKNVDSYGNSFMHW (SEQ ID NO: 4), a CDR2 comprising RASNLES (SEQ ID NO: 5), and a CDR3 comprising QQSNEDPLT (SEQ ID NO: 6).

In a second embodiment, the present invention provides an isolated antibody, or antigen binding portion thereof, that specifically binds to human CD40, wherein the antibody comprises a heavy chain and a light chain, wherein said heavy chain comprises a CDR1 comprising GYAFTNYLIE (SEQ ID NO: 17), a CDR2 comprising VINPGSGGTNYNEKFKG (SEQ ID NO: 18), and a CDR3 comprising SQLGRRFDY (SEQ ID NO: 19); and said light chain comprises a CDR1 comprising KASQDVRTGVA (SEQ ID NO: 20), a CDR2 comprising SASYRNT (SEQ ID NO: 21), and a CDR3 comprising QQHYSPPYT (SEQ ID NO: 22).

The isolated antibody or antigen binding portion thereof can antagonize activities of CD40. The isolated antibody or antigen binding portion thereof can be a chimeric antibody. The isolated antibody or antigen binding portion thereof can be a humanized antibody. The isolated antibody or antigen binding portion thereof can comprise a human heavy chain constant region and a human light chain constant region.

The isolated antibody or antigen binding portion thereof described herein can comprise a human IgG1 Fc domain comprising a mutation at Kabat position 238 that reduces binding to Fc-gamma-receptors (FcgRs), wherein proline 238 (P238) is mutated to one of the residues selected from the group consisting of lysine (K), serine (S), alanine (A), arginine (R) and tryptophan (W), and wherein the antibody or antigen binding portion thereof has reduced FcgR binding.

In certain embodiments, the isolated antibody or antigen binding portion thereof described herein can have P238 mutated to lysine (P238K) in a human IgG1 Fc domain. The isolated antibody or antigen binding portion thereof described herein, can comprise an Fc domain which comprises an amino acid sequence selected from:

```
EPKSCDKTHTCPPCPAPELLGGKSVFLFPPKPKDTLMISRTPEVTCVVVD
VSHEDPEVKFNWYVDGVEVHNAKTKPREEQYNSTYRVVSVLTVLHQDWLN
GKEYKCKVSNKALPAPIEKTISKAKGQPREPQVYTLPPSRDELTKNQVSL
TCLVKGFYPSDIAVEWESNGQPENNYKTTPPVLDSDGSFELYSKLTVDKS
RWQQGNVESCSVMHEALHNHYTQKSLSLSPG,
(IgG1a-P238K (-C-term Lys); SEQ ID NO: 98)

EPKSCDKTHTCPPCPAPELLGGKSVFLFPPKPKDTLMISRTPEVTCVVVD
VSHEDPEVKFNWYVDGVEVHNAKTKPREEQYNSTYRVVSVLTVLHQDWLN
GKEYKCKVSNKALPAPIEKTISKAKGQPREPQVYTLPPSRDELTKNQVSL
TCLVKGFYPSDIAVEWESNGQPENNYKTTPPVLDSDGSPPLYSKLTVDKS
RWQQGNVFSCSVMHEALHNHYTQKSLSLSPGK (IgG1a-P238K;
SEQ ID NO: 9),
```

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGKSVFLFPPKPICDTLMISRTPEVTCVVVDV

SHEDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVSLT

CLVKGFYPSDIAVEWESNGQPENNYKTTPPVLDSDGSFFLYSKLTVDKSR

WQQGNVESCSVMHEALHNHYTQKSLSLSPG (CH1-IgG1a-P238K
(-C-term Lys); SEQ ID NO: 99),

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGKSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK (CH1-IgG1a-P238K;
SEQ ID NO: 10),

EPKSCDKTHTCPPCPAPELLGGKSVFLFPPKPKDTLMISRTPEVTCVVVD

VSHEDPEVIKENWYVDGVEVHNAKTKPREEQYNSTYRVVSVLTVLHQDWL

NGKEYKCKVSNKALPAPIEKTISKAKGQPREPQVYTLPPSREEMTKNQVS

LTCLVKGFYPSDIAVEWESNGQPENNYKTTPPVLDSDGSFFLYSKLTVDK

SRWQQGNVFSCSVMHEALHNHYTQKSLSLSPG (IgG1f-P238K (-C-
term Lys); SEQ ID NO: 100),

EPKSCDKTHTCPPCPAPELLGGKSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSL

TCLVKGFYPSDIAVEWESNGQPENNYKTTPPVLDSDGSFFLYSKLTVDKS

RWQQGNVFSCSVMHEALHNHYTQKSLSLSPGK (IgG1f-P238K; SEQ
ID NO: 11),

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGKSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVESCSVMHEALFINHYTQKSLSLSPG (CH1-IgG1f-P238K
(-C-term Lys); SEQ ID NO: 101).
or

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGKSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVESCSVMHEALHNHYTQKSLSLSPGK (CH1-IgG1f-P238K;
SEQ ID NO: 12).

In certain specific embodiments, the isolated antibody or antigen binding portion thereof described herein can comprise a human IgG1 Fc domain comprising an alanine substituted at Kabat position 297. The isolated antibody or antigen binding portion thereof described herein can comprise the Fc domain wherein the Fc domain comprises an amino acid sequence selected from:

EPKSCDKTHTCPPCPAPELLGGPSVFLFPPKPKDTLMISRTPEVTCVVVD

VSHEDPEVKFNWYVDGVEVHNAKTKPREEQYASTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVESCSVMHEALHNHYTQKSLSLSPG (IgG1a-N297A(-C-
term Lys); SEQ ID NO: 102),

EPKSCDKTHTCPPCPAPELLGGPSVFLFPPKPKDTLMISRTPEVTCVVVD

VSHEDPEVKFNWYVDGVEVHNAKTKPREEQYASTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVESCSVMHEALHNHYTQKSLSLSPGK (IgG1a-N297A; SEQ
ID NO: 13),

ASTKGPSVFPLAPSSKSTSGGTAALGCLVICDYFPEPVTVSWNSGALTSG

VHTFPAVLQSSGLYSLSSVVTVPSSSLGTQTYICNVNHKPSNTKVDKRVE

PKSCDKTHTCPPCPAPELLGGPSVFLFPPKPKDTLMISRTPEVTCVVVDV

SHEDPEVKFNWYVDGVEVHNAKTKPREEQYASTYRVVSVLTVLHQDWLNG

KEYKCKVSNKALPAPIEKTISKAKGQPREPQVYTLPPSRDELTKNQVSLT

CLVKGFYPSDIAVEWESNGQPENNYKTTPPVLDSDGSFELYSKLTVDKSR

WQQGNVESCSVMHEALHNHYTQKSLSLSPG (CH1-IgG1a-N297A
(-C-term Lys); SEQ ID NO: 103),

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYASTYRVVSVLTVLHQDWLNGK

EYKCKVSNKALPAPIEKTISKAKGQPREPQVYTLPPSRDELTKNQVSLTC

LVKGEYPSDIAVEWESNGQPENNYKTTPPVLDSDGSFFLYSKLTVDKSRW

QQGNVFSCSVMHEALHNHYTQKSLSLSPGK (CH1-IgG1a-N297A;
SEQ ID NO: 14),

EPKSCDKTHTCPPCPAPELLGGPSVFLFPPKPKDTLMISRTPEVTCVVVD

VSHEDPEVKFNWYVDGVEVHNAKTKPREEQYASTYRVVSVLTVLHQDWLN

GKEYKCKVSNKALPAPIEKTISKAKGQPREPQVYTLPPSREEMTKNQVSL

TCLVKGFYPSDIAVEWESNGQPENNYKTTPPVLDSDGSFPLYSKLTVDKS

RWQQGNVFSCSVMHEALHNHYTQKSLSLSPG (IgG1f-N297A(-C-
term Lys); SEQ ID NO: 104),

-continued

EPKSCDKTHTCPPCPAPELLGGPSVFLFPPKPKDTLMISRTPEVTCVVVD

VSHEDPEVKFNWYVDGVEVHNAKTKPREEQYASTYRVVSVLTVLHQDWLN

GKEYKCKVSNKALPAPIEKTISKAKGQPREPQVYTLPPSREEMTKNQVSL

TCLVKGFYPSDIAVEWESNGQPENNYKTTPPVLDSDGSFELYSKLTVDKS

RWQQGNVESCSVMHEALHNHYTQKSLSLSPGK (IgG1f-N297A; SEQ
ID NO: 15),

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYASTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFELYSKLTVDKSRW

QQGNVESCSVMHEALHNHYTQKSLSLSPG(CH1-IgG1f-N297A(-C-
term Lys); SEQ ID NO: 105),
or

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYASTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFELYSKLTVDKSRW

QQGNVESCSVMHEALHNHYTQKSLSLSPGK (CH1-IgG1f-N297A;
SEQ ID NO: 16).

In certain specific embodiments, the isolated antibody or antigen binding portion thereof comprises: (1) a variable heavy chain ($V_H$) having the amino acid sequence of SEQ ID NO: 7 or (2) a variable light chain ($V_L$) having the amino acid sequence of SEQ ID NO: 8. For example, the isolated antibody or antigen binding portion comprises: (1) a variable heavy chain ($V_H$) having the amino acid sequence of SEQ ID NO: 7, and (2) a variable light chain ($V_L$) having the amino acid sequence of SEQ ID NO: 8. In a specific embodiment, the isolated antibody or antigen binding portion thereof comprises (1) a heavy chain having the amino acid sequence of SEQ ID NO: 85, and (2) a light chain having the amino acid sequence of SEQ ID NO: 88. In other specific embodiments, the isolated antibody or antigen binding portion thereof comprises:

(1) a heavy chain having the amino acid sequence of SEQ ID NO: 106 and (2) a light chain having the amino acid sequence of SEQ ID NO: 88;

(1) a heavy chain having the amino acid sequence of SEQ ID NO: 107 and (2) a light chain having the amino acid sequence of SEQ ID NO: 88;

(1) a heavy chain having the amino acid sequence of SEQ ID NO: 108 and (2) a light chain having the amino acid sequence of SEQ ID NO: 88; or (1) a heavy chain having an amino acid sequence selected from SEQ ID NO: 84, 109, 110, or 111; and (2) a 5F11-45 light chain having the amino acid sequence of SEQ ID NO: 88.

In other specific embodiments, the isolated antibody or antigen binding portion thereof comprises (1) a variable heavy chain ($V_H$) selected from the group consisting of: hz-HC1 (SEQ ID NO: 23), hz-HC2 (SEQ ID NO: 24), hz-HC3 (SEQ ID NO: 25), hz-HC4 (SEQ ID NO: 26), hz-HC5 (SEQ ID NO: 27), hz-HC6 (SEQ ID NO: 28), hz-HC7 (SEQ ID NO: 29), hz-HC8 (SEQ ID NO: 30), hz-HC9 (SEQ ID NO: 31), hz-HC10 (SEQ ID NO: 32), and hz-HC11 (SEQ ID NO: 33); and/or (2) a variable light chain ($V_L$) selected from the group consisting of: hz-LC1 (SEQ ID NO: 34), hz-LC2 (SEQ ID NO: 35), hz-LC3 (SEQ ID NO: 36), hz-LC4 (SEQ ID NO: 37), and hz-LC5 (SEQ ID NO: 38).

In certain specific embodiments, the isolated antibody or antigen binding portion thereof comprises (1) a heavy chain amino acid sequence selected from SEQ ID NO: 39, SEQ ID NO: 40, SEQ ID NO: 42, and SEQ ID NO: 43, wherein the C-terminus optionally further comprises a lysine; and/or (2) a variable light chain ($V_L$) amino acid sequence selected from SEQ ID NO: 41, and SEQ ID NO: 44. To illustrate, the isolated antibody or antigen binding portion thereof is selected from the group consisting of:

a) Y1238-hz1-P238K having a heavy chain of SEQ ID NO: 39 and light chain of SEQ ID NO: 41;

b) Y1238-hz1-N297A having a heavy chain of SEQ ID NO: 40 and light chain of SEQ ID NO: 41;

c) Y1238-hz2-P238K having a heavy chain of SEQ ID NO: 42 and light chain of SEQ ID NO: 44; and d) Y1238-hz2-N297A having a heavy chain of SEQ ID NO: 43 and light chain of SEQ ID NO: 44.

The antibody or antigen binding portion thereof disclosed herein, wherein the antigen binding portion is selected from the group consisting of Fv, Fab, F(ab')2, Fab', dsFv, scFv, sc(Fv)2, diabodies, and scFv-Fc.

The antibody or antigen binding portion thereof disclosed herein, wherein the antibody or antigen-binding portion thereof is linked to a therapeutic agent.

The antibody or antigen binding portion thereof disclosed herein, wherein the antibody or antigen-binding portion thereof is linked to a second functional moiety having a different binding specificity than said antibody or antigen binding portion thereof.

The antibody or antigen binding portion thereof disclosed herein further comprising an additional moiety.

A nucleic acid encoding an isolated antibody or antigen binding portion thereof is disclosed herein. An expression vector comprising the nucleic acid molecule is disclosed herein. Also contemplated is a cell transformed with the expression vector.

Also disclosed is a method of preparing an anti-human CD40 antibody, or antigen binding portion thereof, comprising:

a) expressing the antibody, or antigen binding portion thereof, in the cell transformed with the expression vector comprising the nucleic acid molecule encoding an isolated antibody or antigen binding portion thereof disclosed herein; and b) isolating the antibody, or antigen binding portion thereof, from the cell.

Also provided is a pharmaceutical composition comprising: a) the antibody, or antigen binding portion thereof disclosed herein; and b) a pharmaceutically acceptable carrier.

A method is provided of treating or preventing an immune response in a subject comprising administering to the subject the antibody, or the antigen binding portion thereof disclosed herein. In such method of treating or preventing an immune response in the subject, the subject has a disease selected from the group consisting of: Addison's disease, allergies, anaphylaxis, ankylosing spondylitis, asthma, atherosclerosis, atopic allergy, autoimmune diseases of the ear, autoimmune diseases of the eye, autoimmune hepatitis, autoimmune parotitis, bronchial asthma, coronary heart disease, Crohn's disease, diabetes, epididymitis, glomerulonephritis, Graves' disease, Guillain-Barre syndrome, Hashimoto's disease, hemolytic anemia, idiopathic thrombocytopenic purpura, inflammatory bowel disease, immune response to recombinant drug products (e.g., Factor VII in hemophiliacs), systemic lupus erythematosus, multiple sclerosis, myasthenia gravis, pemphigus, psoriasis, rheumatic fever, rheumatoid arthritis, sarcoidosis, scleroderma, Sjogren's syndrome, spondyloarthropathies, thyroiditis, transplant rejection, vasculitis, and ulcerative colitis.

Also contemplated is a use of an antibody, or antigen binding portion thereof as disclosed here, or a medicament comprising the same, for use to treat a subject in need thereof. Further contemplated is an antibody, or antigen binding portion thereof as disclosed herein in a therapeutically-effective amount, for use in treating or preventing an immune response, wherein the antibody or antigen binding portion thereof is for administering to a patient in need thereof.

BRIEF DESCRIPTION OF THE FIGURES

FIGS. 2A-2C, depicts iDC activation data for treatment of immature dendritic cells (iDCs) by anti-CD40 antibody 5F11 in two independent donors. Increases in IL-6 (interleukin-6) (FIG. 2A) from the cell culture media and cell surface marker expression (CD54 and CD86) as indicated by flow cytometry mean fluorescence staining with anti-CD86 and anti-CD54 antibodies. The mean fluorescence intensity (MFI) is measured on the Y-axis in both FIG. 2B and FIG. 2C. Concentration of antibody in μg/ml is indicated. Inclusion of CHO-CD32 cells in the assay is indicated by 'x-link'.

FIGS. 3A-3C, depicts iDC activation data for treatment of immature dendritic cells (iDCs) with the chimeric Y1238 anti-CD40 antibodies in two independent donors. Increases in IL-6 (FIG. 3A) and cell surface marker expression (i.e., CD54 and CD86) as indicated by flow cytometry mean fluorescence staining with anti-CD86 (FIG. 3C) and anti-CD54 (FIG. 3B) antibodies. Concentration of antibody in μg/ml is indicated. Inclusion of CHO-CD32 cells is indicated by 'x-link'.

FIGS. 4A-4C, depicts iDC activation data for treatment of immature dendritic cells (iDCs) by anti-CD40 antibodies Y1238-P238K and Y1238-N297A. Increases in IL-6 (FIG. 4A) from the cell culture media was measured. Cell surface marker expression (CD54 and CD86) was measured as indicated by flow cytometry mean fluorescence staining with anti-CD86 (FIG. 4B) and anti-CD54 (FIG. 4C) antibodies. Concentration of antibody in μg/ml is indicated. Inclusion of CHO-CD32 cells is indicated.

FIGS. 5A-5C, depicts iDC activation data for treatment of iDCs with humanized (hz) versions of Y1238 antibodies with (x-link) and without the addition of overexpressing CD32 CHO cells. The treatment concentration of the antibody 10, 30, or 100 μg/ml is indicated. FIG. 5A: Cytokine production IL-6 in pg/ml (top panel). FIG. 5B: The mean fluorescence intensity of staining for CD54. FIG. 5C: Mean fluorescence intensity of CD86.

FIGS. 6A-6C, depicts iDC activation data for treatment of immature dendritic cells (iDCs) by anti-CD40 antibody 5F11 in 8 independent donors. Increases in IL-6 (interleukin-6) (FIG. 6A) from the cell culture media and cell surface marker expression (CD54; FIG. 6B and CD86; FIG. 6C) as indicated by flow cytometry mean fluorescence staining with anti-CD86 and anti-CD54 antibodies The mean fluorescence intensity (MFI) is measured on the Y-axis in both FIG. 6B and FIG. 6C. Concentration of antibody in μg/ml is indicated (10, 30, or 100 μg/ml). Inclusion of CHO-CD32 cells in the assay is as indicated to mediate FcgR mediated cross-linking or clustering. CD40 agonist antibody #2141 and the anti-CD40-dAB-IgG4 serve as positive controls. An IgG4-L6 fusion protein serves as a negative control.

DETAILED DESCRIPTION

Figure 1:
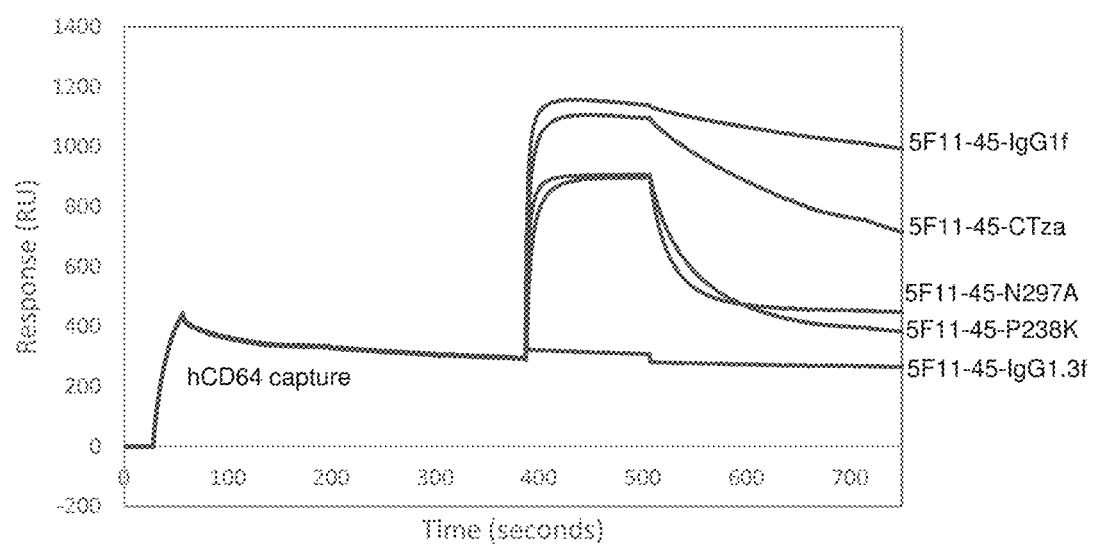
FIG. 1 depicts SPR sensorgram data for the capture of 7 μg/ml hCD64-His on an anti-His FAB surface with binding of 1 μM 5F11-45 antibodies.

The present disclosure is directed to anti-CD40 antibodies, and in particular, antagonistic anti-CD40 antibodies. For therapeutic targets such as CD40, FcgR-mediated cross-linking of anti-CD40 antibodies has the potential to lead to undesirable agonist signaling and potential for toxicity. The present disclosure also describes antagonistic anti-CD40 antibodies having reduced engagement of the "low affinity". FcgRs hCD32a/FcgRIIa, hCD32b/FcgRIIb, hCD16a/FcgRIIIa, and hCD16b/FcgRIIIb. Reduced engagement of low affinity FcgR's is expected to reduce the likelihood of undesirable agonist signaling and undesirable potential for toxicity.

Definitions & Abbreviations

Further abbreviations and definitions are provided below.
APC antigen presenting cells
CD54 also referred to as ICAM-1
CDR complementarity determining regions
$C_H$ or CH constant heavy chain
$C_L$ or CL constant light chain
CHO cell Chinese hamster ovary cell
dAb domain antibody
FcgR interchangeable with FcγR
FR Framework region
GM-CSF granulocyte macrophage colony stimulating factor
HC heavy chain
iDC immature dendritic cells
IFN interferon
IgG Immunoglobulin G
IL-6 Interleukin-6
LC light chain
mAb monoclonal antibody
mg milligram
ml or mL milliliter
ng nanogram
nM nanomolar
PI isoelectric point
SPR surface plasmon resonance
TNF tumor necrosis factor
μg microgram
μM micromolar
$V_L$ or $V_L$ variable light chain domain
$V_H$ or $V_H$ variable heavy chain domain
Further abbreviations and definitions are provided herein
In accordance with this detailed description, the following abbreviations and definitions apply. It must be noted that as used herein, the singular forms "a", "an", and "the" include plural referents unless the context clearly dictates otherwise. Thus, for example, reference to "an antibody" includes a plurality of such antibodies and reference to "the dosage" includes reference to one or more dosages and equivalents thereof known to those skilled in the art, and so forth.

As used here, the term "about" is understood by persons of ordinary skill in the art and will vary to some extent on the context in which it is used. Generally, "about" encompasses a range of values that are plus/minus 10% of a referenced value unless indicated otherwise in the specification.

It is understood that any and all whole or partial integers between the ranges set forth are included herein.

CD40 is also known and referred to as B-cell surface antigen CD40, Bp50, CD40L receptor, CDw40, CDW40, MGC9013, p50, TNFRSF5, and Tumor necrosis factor receptor superfamily member 5. "Human CD40" refers to the CD40 comprising the following amino acid sequence:

```
                                              (SEQ ID NO: 45)
MVRLPLQCVL  WGCLLTAVHP  EPPTACREKQ  YLINSQCCSL

CQPGQKLVSD  CTEFTETECL  PCGESEFLDT  WNRETHCHQH

KYCDPNLGLR  VQQKGTSETD  TICTCEEGWH  CTSEACESCV

LHRSCSPGFG  VKQIATGVSD  TICEPCPVGF  FSNVSSAFEK

CHPWTSCETK  DLVVQQAGTN  KTDVVCGPQD  RLRALVVIPI

IFGILFAILL  VLVFIKKVAK  KPTNKAPHPK  QEPQEINFPD

DLPGSNTAAP  VQETLHGCQP  VTQEDGKESR  ISVQERQ.
```

As used herein, the term "variable domain" refers to immunoglobulin variable domains defined by Kabat et al., *Sequences of Immunological Interest*, 5th ed., U.S. Dept. Health & Human Services, Washington, D.C. (1991). The numbering and positioning of CDR amino acid residues within the variable domains is in accordance with the well-known Kabat numbering convention. $V_{11}$, "variable heavy chain" and "variable heavy chain domain" refer to the variable domain of a heavy chain $V_L$, "variable light chain" and "variable light chain domain" refer to the variable domain of a light chain.

The term "human," when applied to antibodies, means that the antibody has a sequence, e.g., FR and/or CH domains, derived from a human immunoglobulin. A sequence is "derived from" a human immunoglobulin coding sequence when the sequence is either: (a) isolated from a human individual or from a cell or cell line from a human individual; (b) isolated from a library of cloned human antibody gene sequences or of human antibody variable domain sequences; or (c) diversified by mutation and selection from one or more of the polypeptides above.

An "isolated" compound as used herein means that the compound is removed from at least one component with which the compound is naturally associated with in nature.

Antibodies of the present disclosure can be administered to human patients while largely avoiding the anti-antibody immune response often provoked by the administration of antibodies from other species, e.g., mouse. For example, murine antibodies can be "humanized" by grafting murine CDRs onto a human variable domain FR, according to procedures known in the art. Human antibodies as disclosed herein, however, can be produced without the need for genetic manipulation of a murine antibody sequence.

The anti-CD40 antibodies useful in the present disclosure comprise three complementarity-determining regions (CDRs) and four framework regions (FRs), arranged from amino-terminus to carboxy-terminus in the following order: FR1, CDR1, FR2, CDR2, FR3, CDR3, FR4. The three CDRs contain most of the residues that form specific interactions with the antigen and are primarily responsible for antigen recognition.

In a specific embodiment, the anti-CD40 antibodies of the present disclosure can comprise CDRs of humanized antibody 5F11-45. Amino acid sequences of 5F11-45 are provided in Table 1.

TABLE 1

| 5E11-45 sequences | | |
|---|---|---|
| Heavy chain-variable region | QVQLVQSGAEVKKPGSSVKVSCKASGY TFTDLSMHWVRQAPGQGLEWMGYITP SSGYTAYNQKFKGKTTLTADKSTSTAY MELSSLRSEDTAVYYCARLILQRGAYW GQGTLVTVSS | SEQ ID NO: 7 |
| VH-CDR1 | GYTFTDLSMHW (SEQ ID NO: 1) | Amino acids 26-35 of SEQ ID NO: 7 |
| VH-CDR2 | YITPSSGYTAYNQKFKG (SEQ ID NO: 2) | Amino acids 50-66 of SEQ ID NO: 7 |
| VH-CDR3 | LILQRGAY (SEQ ID NO: 3) | A mino acids 99-106 of SEQ ID NO: 8 |
| HC_5F11-45-P238K-IgG1a with and without C-terminal lysine | QVQLVQSGAEVKKPGSSVKVSCKASGY TFTDLSMHWVRQAPGQGLEWMGYITP SSGYTAYNQKFKGKTTLTADKSTSTAY MELSSLRSEDTAVYYCARLILQRGAYW GQGTLVTVSSASTKGPSVFPLAPSSKST SGGTAALGCLVKDYFPEPVTVSWNSGA LTSGVHTFPAVLQSSGLYSLSSVVTVPS SSLGTQTYICNVNHKPSNTKVDKRVEP KSCDKTHTCPPCPAPELLGGKSVFLFPP KPKDTLMISRTPEVTCVVVDVSHEDPE VKFNWYVDGVEVHNAKTKPREEQYNS TYRVVSVLTVLHQDWLNGKEYKCKVS NKALPAPIEKTISKAKGQPREPQVYTLP PSRDELTKNQVSLTCLVKGFYPSDIAVE | SEQ ID NO: 85 |

TABLE 1-continued

| | 5E11-45 sequences | |
|---|---|---|
| | WESNGQPENNYKTTPPVLDSDGSFFLY SKLTVDKSRWQQGNVFSCSVMHEALH NHYTQKSLSLSPGK | |
| | QVQLVQSGAEVKKPGSSVKVSCKASGY TFTDLSMHWVRQAPGQGLEWMGYITP SSGYTAYNQKFKGKTTLTADKSTSTAY MELSSLRSEDTAVYYCARLILQRGAYW GQGTLVTVSSASTKGPSVFPLAPSSKST SGGTAALGCLVKDYFPEPVTVSWNSGA LTSGVHTFPAVLQSSGLYSLSSVVTVPS SSLGTQTYICNVNHKPSNTKVDKRVEP KSCDKTHTCPPCPAPELLGGKSVFLEPP KPKDTLMISRTPEVTCVVVDVSHEDPE VKFNWYVDGVEVHNAKTKPREEQYNS TYRVVSVLTVLHQDWLNGKEYKCKVS NKALPAPIEKTISKAKGQPREPQVYTLP PSRDELTKNQVSLTCLVKGFYPSDIAVE WESNGQPENNYKTTPPVLDSDGSFFLY SKLTVDKSRWQQGNVFSCSVMHEALH NHYTQKSLSLSPG | SEQ ID NO: 106 |
| HC_5F11-45-P238K-IgG1f with and without C-terminal lysine | QVQLVQSGAEVKKPGSSVKVSCKASGY TFTDLSMHWVRQAPGQGLEWMGYITP SSGYTAYNQKFKGKTTLTADKSTSTAY MELSSLRSEDTAVYYCARLILQRGAYW GQGTLVTVSSASTKGPSVFPLAPSSKST SGGTAALGCLVKDYFPEPVTVSWNSGA LTSGVHTFPAVLQSSGLYSLSSVVTVPS SSLGTQTYICNVNHKPSNTKVDKRVEP KSCDKTHTCPPCPAPELLGGKSVFLEPP KPKDTLMISRTPEVTCVVVDVSHEDPE VKFNWYVDGVEVHNAKTKPREEQYNS TYRVVSVLTVLHQDWLNGKEYKCKVS NKALPAPIEKTISKAKGQPREPQVYTLP PSREEMTKNQVSLTCLVKGFYPSDIAVE WESNGQPENNYKTTPPVLDSDGSFFLY SKLTVDKSRWQQGNVFSCSVMHEALH NHYTQKSLSLSPGK | SEQ ID NO: 108 |
| | QVQLVQSGAEVKKPGSSVKVSCKASGY TFTDLSMHWVRQAPGQGLEWMGYITP SSGYTAYNQKFKGKTTLTADKSTSTAY MELSSLRSEDTAVYYCARLILQRGAYW GQGTLVTVSSASTKGPSVFPLAPSSKST SGGTAALGCLVKDYFPEPVTVSWNSGA LTSGVHTFPAVLQSSGLYSLSSVVTVPS SSLGTQTYICNVNHKPSNTKVDKRVEP KSCDKTHTCPPCPAPELLGGKSVFLFPP KPKDTLMISRTPEVTCVVVDVSHEDPE VKFNWYVDGVEVHNAKTKPREEQYNS TYRVVSVLTVLHQDWLNGKEYKCKVS NKALPAPIEKTISKAKGQPREPQVYTLP PSREEMTKNQVSLTCLVKGFYPSDIAVE WESNGQPENNYKTTPPVLDSDGSFFLY SKLTVDKSRWQQGNVFSCSVMHEALH NHYTQKSLSLSPG | SEQ ID NO: 107 |
| HC_5F11-45-N297A-IgG with and without C-terminal lysine | QVQLVQSGAEVKKPGSSVKVSCKASGY fTFTDLSMHWVRQAPGQGLEWMGYITP SSGYTAYNQKFKGKTTLTADKSTSTAY MELSSLRSEDTAVYYCARLILQRGAYW GQGTLVTVSSASTKGPSVFPLAPSSKST SGGTAALGCLVKDYFPEPVTVSWNSGA LTSGVHTFPAVLQSSGLYSLSSVVTVPS SSLGTQTYICNVNHKPSNTKVDKRVEP KSCDKTHTCPPCPAPELLGGPSVFLFPP KPKDTLMISRTPEVTCVVVDVSHEDPE VKFNWYVDGVEVHNAKTKPREEQYAS TYRVVSVLTVLHQDWLNGKEYKCKVS NKALPAPIEKTISKAKGQPREPQVYTLP PSREEMTKNQVSLTCLVKGFYPSDIAVE WESNGQPENNYKTTPPVLDSDGSFFLY SKLTVDKSRWQQGNVFSCSVMHEALH NHYTQKSLSLSPGK | SEQ ID NO: 84 |
| | QVQLVQSGAEVKKPGSSVKVSCKASGY TFTDLSMHWVRQAPGQGLEWMGYITP SSGYTAYNQKFKGKTTLTADKSTSTAY MELSSLRSEDTAVYYCARLILQRGAYW GQGTLVTVSSASTKGPSVFPLAPSSKST | SEQ ID NO: 109 |

TABLE 1-continued

5E11-45 sequences

| | | |
|---|---|---|
| | SGGTAALGCLVKDYFPEPVTVSWNSGA<br>LTSGVHTFPAVLQSSGLYSLSSVVTVPS<br>SSLGTQTYICNVNHKPSNTKVDKRVEP<br>KSCDKTHTCPPCPAPELLGGPSVFLFPP<br>KPKDTLMISRTPEVTCVVVDVSHEDPE<br>VKFNWYVDGVEVHNAKTKPREEQYAS<br>TYRVVSVLTVLHQDWLNGKEYKCKVS<br>NKALPAPIEKTISKAKGQPREPQVYTLP<br>PSREEMTKNQVSLTCLVKGFYPSDIAVE<br>WESNGQPENNYKTTPPVLDSDGSFFLY<br>SKLTVDKSRWQQGNVFSCSVMHEALH<br>NHYTQKSLSLSPG | |
| HC_5F11-45-<br>N297A-IgG1a<br>with and<br>without C-<br>terminal<br>lysine | QVQLVQSGAEVKKPGSSVKVSCKASGY<br>TFTDLSMHWVRQAPGQGLEWMGYITP<br>SSGYTAYNQKFKGKTTLTADKSTSTAY<br>MELSSLRSEDTAVYYCARLILQRGAYW<br>GQGTLVTVSSASTKGPSVFPLAPSSKST<br>SGGTAALGCLVKDYFPEPVTVSWNSGA<br>LTSGVHTFPAVLQSSGLYSLSSVVTVPS<br>SSLGTQTYICNVNHKPSNTKVDKRVEP<br>KSCDKTHTCPPCPAPELLGGPSVFLFPP<br>KPKDTLMISRTPEVTCVVVDVSHEDPE<br>VKFNWYVDGVEVHNAKTKPREEQYAS<br>TYRVVSVLTVLHQDWLNGKEYKCKVS<br>NKALPAPIEKTISKAKGQPREPQVYTLP<br>PSRDELTKNQVSLTCLVKGFYPSDIAVE<br>WESNGQPENNYKTTPPVLDSDGSFFLY<br>SKLTVDKSRWQQGNVFSCSVMHEALH<br>NHYTQKSLSLSPGK | SEQ ID NO: 110 |
| | QVQLVQSGAEVKKPGSSVKVSCKASGY<br>TFTDLSMHWVRQAPGQGLEWMGYITP<br>SSGYTAYNQKFKGKTTLTADKSTSTAY<br>MELSSLRSEDTAVYYCARLILQRGAYW<br>GQGTLVTVSSASTKGPSVFPLAPSSKST<br>SGGTAALGCLVKDYFPEPVTVSWNSGA<br>LTSGVHTFPAVLQSSGLYSLSSVVTVPS<br>SSLGTQTYICNVNHKPSNTKVDKRVEP<br>KSCDKTHTCPPCPAPELLGGPSVFLEPP<br>KPKDTLMISRTPEVTCVVVDVSHEDPE<br>VKFNWYVDGVEVHNAKTKPREEQYAS<br>TYRVVSVLTVLHQDWLNGKEYKCKVS<br>NKALPAPIEKTISKAKGQPREPQVYTLP<br>PSRDELTKNQVSLTCLVKGFYPSDIAVE<br>WESNGQPENNYKTTPPVLDSDGSFFLY<br>SKLTVDKSRWQQGNVESCSVMHEALH<br>NHYTQKSLSLSPG | SEQ ID NO: 111 |
| Light chain-<br>variable<br>region | DIVLTQSPDSLAVSLGERATINCRASKN<br>VDSYGNSFMHWYQQKPGQPPKLLIYRA<br>SNLESGVPDRFSGSGSGTDFTLTISSLQA<br>EDVAVYYCQQSNEDPLTFGQGTKLEIK | SEQ ID NO: 8 |
| VL-CDR1 | RASKNVDSYGNSFMHW (SEQ ID NO: 4) | Amino acids 24-38 of<br>SEQ ID NO: 8 |
| VL-CDR2 | RASNLES (SEQ ID NO: 5) | Amino acids 54-60 of<br>SEQ ID NO: 8 |
| VL-CDR3 | QQSNEDPLT (SEQ ID NO: 6) | Amino acids 93-101<br>of SEQ ID NO: 8 |
| LC_5F11-45 | DIVLTQSPDSLAVSLGERATINCRASKNVDS<br>YGNSFMHWYQQKPGQPPKLLIYRASNLES<br>GVPDRFSGSGSGTDFTLTISSLQAEDVAVY<br>YCQQSNEDPLTFGQGTKLEIKRTVAAPSVFI<br>FPPSDEQLKSGTASVVCLLNNFYPREAKVQ<br>WKVDNALQSGNSQESVTEQDSKDSTYSLS<br>STLTLSKADYEKHKVYACEVTHQGLSSPVT<br>KSFNRGEC | SEQ ID NO: 88;<br>VL sequence is<br>underlined |

In one embodiment, the antibodies of the disclosure can comprise the amino acid sequences of the CDR1, CDR2, and CDR3 regions of the humanized 5F11-45 variable heavy and light chains sequences (see e.g., SEQ ID NOS: 7 and 8 respectively, as an example). Monoclonal antibodies contain all 6 CDRs (3 for the $V_H$ and 3 for the $V_L$), for example, GYTFTDLSMHW (SEQ ID NO: 1), YITPSSGYTAYNQKFKG (SEQ ID NO: 2), and LILQR-GAY (SEQ ID NO: 3) for the variable heavy chain CDRs 1-3 respectively and RASKNVDSYGNSFMHW (SEQ ID NO:

4), RASNLES (SEQ ID NO: 5), and QQSNEDPLT (SEQ ID NO: 6) for the variable light chain CDRs 1-3 respectively.

In another embodiment, the antibodies of the disclosure can comprise the amino acid sequences of the CDR1, CDR2, and CDR3 regions of the humanized Y1238 variable heavy and light chains sequences (see e.g., SEQ ID NOS: 23 and 34 respectively as examples). Monoclonal antibodies contain all 6 CDRs (3 for the $V_H$ and 3 for the $V_L$), for example, GYAFTNYLIE (SEQ ID NO: 17), VINPGSGGTNYNEKFKG (SEQ ID NO: 18), and SQL-GRRFDY (SEQ ID NO: 19) for the variable heavy chain CDRs 1-3 respectively and KASQDVRTGVA (SEQ ID NO: 20), SASYRNT (SEQ ID NO: 21), and QQHYSPPYT (SEQ ID NO: 22) for the variable light chain CDRs 1-3 respectively.

An "antibody" (Ab) shall include, without limitation, an immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises three constant domains, $C_{H1}$, $C_{H2}$ and $C_{H3}$. Each light chain comprises a light chain variable region (abbreviated herein as $V_L$) and a light chain constant region. The light chain constant region is comprises one constant domain, $C_L$. The $V_H$ and $V_L$ regions can be further subdivided into regions of hypervariability, termed complementarity determining regions (CDRs), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen.

An "antigen binding portion" of an Ab (also called an "antigen-binding fragment") or antigen binding portion thereof refers to one or more sequences of an Ab (full length or fragment of the full length antibody) that retain the ability to bind specifically to the antigen bound by the whole Ab. Examples of an antigen-binding fragment include Fab, F(ab')2, scFv (single-chain variable fragment), Fab', dsFv, sc(Fv)2, and scFv-Fc.

A "humanized" antibody refers to an Ab in which some, most or all of the amino acids outside the CDR domains of a non-human Ab are replaced with corresponding amino acids derived from human immunoglobulins. In one embodiment of a humanized form of an Ab, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the Ab to bind to a particular antigen. A "humanized" Ab retains an antigenic specificity similar to that of the original Ab.

A "chimeric antibody" refers to an Ab in which the variable regions are derived from one species and the constant regions are derived from another species, such as an Ab in which the variable regions are derived from a mouse Ab and the constant regions are derived from a human Ab.

As used herein, "specific binding" refers to the binding of an antigen by an antibody with a dissociation constant ($K_d$) of about 1 µM or lower as measured, for example, by surface plasmon resonance (SPR). Suitable assay systems include the BIAcore™ (GE Healthcare Life Sciences, Marlborough, Mass.) surface plasmon resonance system and BIAcore™ kinetic evaluation software (e.g., version 2.1).

Binding of the present antibodies to CD40 antagonizes CD40 activity. "CD40 activities" include, but are not limited to, T cell activation (e.g., induction of T cell proliferation or cytokine secretion), macrophage activation (e.g., the induction of reactive oxygen species and nitric oxide in the macrophage), and B cell activation (e.g., B cell proliferation, antibody isotype switching, or differentiation to plasma cells). CD40 activities can be mediated by interaction with other molecules. "CD40 activities" include the functional interaction between CD40 and the following molecules, which are identified by their Uniprot Accession Number is parentheses:

| | |
|---|---|
| CALR | (P27797); |
| ERP44 | (Q9BS26); |
| FBL | (P22087); |
| POLR2H | (P52434); |
| RFC5 | (P40937); |
| SGK1 | (O00141); |
| SLC30A7 | (Q8NEW0); |
| SLC39A7 | (Q92504); |
| TRAF2 | (Q5T1L5); |
| TRAF3 | (Q13114); |
| TRAF6 | (Q9Y4K3); |
| TXN | (Q5T937); |
| UGGT1 | (Q9NYU2); and |
| USP15 | (Q9Y4E8). |

For example, a CD40 "activity" includes an interaction with TRAF2. CD40/TRAF2 interaction activates NF-κB and JNK. See Davies et al., Mol. Cell Biol. 25: 9806-19 (2005). This CD40 activity thus can be determined by CD40-dependent cellular NF-κB and JNK activation, relative to a reference.

As used herein, the terms "activate," "activates," and "activated" refer to an increase in a given measurable CD40 activity by at least 10% relative to a reference, for example, at least 10%, 25%, 50%, 75%, or even 100%, or more. A CD40 activity is "antagonized" if the CD40 activity is reduced by at least 10%, and in an exemplary embodiment, at least about 20%, 30%, 40%, 50%, 60%, 70%, 80%, 90%, 95%, 97%, or even 100% (i.e., no detectable activity), relative to the absence of the antagonist. For example, an antibody may antagonize some or all CD40 activity, while not activating CD40. For example, the antibody may not activate B cell proliferation. The antibody may not activate cytokine secretion by T cells, where the cytokine is at least one cytokine selected from the group consisting of IL-2, IL-6, IL-10, IL-13, TNF-α, IFN-γ.

Variable domains may comprise one or more framework regions (PR) with the same amino acid sequence as a corresponding framework region encoded by a human germline antibody gene segment. Preferred framework sequences for use in the antibodies described herein are those that are structurally similar to the framework sequences used by antibodies described herein. The $V_H$ CDR1, 2 and 3 sequences, and the $V_L$ CDR1, 2 and 3 sequences, can be grafted onto framework regions that have the identical sequence as that found in the germline immunoglobulin gene from which the framework sequence derive, or the CDR sequences can be grafted onto framework regions that contain up to 20, preferably conservative, amino acid substitutions as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al.).

Exemplary framework regions include but are not limited to those in TABLES 2 and 3 below. The sequences are in amino-to-carboxy terminus format. Exemplified heavy chain framework regions are shown in TABLE 2. A preferred group of heavy framework sequences for the humanized 5F11-45 VH is: QVQLVQSGAEVKKPGSSVKVSCKAS (FR1; SEQ ID NO: 46), WVRQAPGQGLEWMG (FR2; SEQ ID NO: 49), KTTLTADKSTSTAYMELSSLRSEDTAVYYCAR (FR3; SEQ ID NO: 51), and WGQGTLVTVSS (FR4: SEQ ID NO: 60). A preferred group of heavy framework sequences for the humanized Y1238 VH is: QVQLVQSGAEVKKPGASVKVSCKAS (FR1; SEQ ID NO: 47), WVRQAPGQGLEWMG (FR2; SEQ ID NO: 49), RVTMTRDTSISTAYMELSRLRSDDTAVYYCAR (FR3; SEQ ID NO: 52), and WGQGTLVTVSS (FW4; SEQ ID NO: 60).

TABLE 2

| Heavy Framework Region | Sequence | SEQ ID NO. |
|---|---|---|
| FR1 | QVQLVQSGAEVKKPGSSVKVSCKAS | 46 |
| FR1 | QVQLVQSGAEVKKPGASVKVSCKAS | 47 |
| FR1 | QVQLVQSGAEVVKPGASVKVSCKAS | 48 |
| FR2 | WVRQAPGQGLEWMG | 49 |
| FR2 | WVRQRPGQGLEWMG | 50 |
| FR3 | KTTLTADKSTSTAYMELSSLRSEDTAVYYCAR | 51 |
| FR3 | RVTMTRDTSISTAYMELSRLRSDDTAVYYCAR | 52 |
| FR3 | RVTMTADTSISTAYMELSRLRSDDTAVYYCAR | 53 |
| FR3 | RVTMTRDKSISTAYMELSRLRSDDTAVYYCAR | 54 |
| FR3 | RVTMTADKSISTAYMELSRLRSDDTAVYYCAR | 55 |
| FR3 | RVTLTADKSISTAYMELSRLRSDDTAVYYCAR | 56 |
| FR3 | RVTMTADKSSSTAYMQLSRLRSDDTAVYFCAR | 57 |
| FR3 | RVTLTADKSSSTAYMQLSRLRSDDTAVYFCAR | 58 |
| FR3 | RVTMTRDKSSSTAYMELSRLRSDDTAVYFCAR | 59 |
| FR4 | WGQGTLVTVSS | 60 |

Exemplified light chain framework regions are shown in TABLE 3. A preferred group of light chain framework regions for the humanized 5F11-45 VL include the following: DIVLTQSPDSLAVSLGERATINC (FR1; SEQ ID NO: 61), WYQQKPGQPPKLLIY (FR2; SEQ ID NO: 63), GVPDRFSGSGSGTDFTLTISSLQAEDVAVYYC (FR3; SEQ ID NO: 66), and FGQGTKLEIK (FR4; SEQ ID NO: 71). A preferred group of light chain framework regions for the humanized Y1238 VL include the following:

```
                                  (FR1; SEQ ID NO: 62)
DIQMTQSPSSLSASVGDRVTITC, (FR2; SEQ ID NO: 64)
WYQQKPGKAPKLLIY, (FR3; SEQ ID NO: 67)
GVPSRFSGSGSGTDFTFTISSLQPEDIATYYC, (FR3; SEQ ID NO: 68)
GVPSRFSGSRSGTDFTFTISSLQPEDIATYYC,
and (FR4; SEQ ID NO: 72)
FGGGTKVEIK.
```

TABLE 3

| Light Framework Region | Sequence | SEQ ID NO. |
|---|---|---|
| FR1 | DIVLTQSPDSLAVSLGERATINC | 61 |
| FR1 | DIQMTQSPSSLSASVGDRVTITC | 62 |
| FR2 | WYQQKPGQPPKLLIY | 63 |
| FR2 | WYQQKPGKAPKLLIY | 64 |
| FR2 | WYQQKPGQSPKLLIY | 65 |
| FR3 | GVPDRFSGSGSGTDFTLTISSLQAEDVAVYYC | 66 |
| FR3 | GVPSRFSGSGSGTDFTFTISSLQPEDIATYYC | 67 |
| FR3 | GVPSRFSGSRSGTDFTFTISSLQPEDIATYYC | 68 |
| FR3 | GVPSRFSGSRSGTDFTFTISSLQPEDIAVYYC | 69 |
| FR3 | GVPSRFSGSRSGTDFTFTISSLQAEDIAVYYC | 70 |
| FR4 | FGQGTKLEIK | 71 |
| FR4 | FGGGTKVEIK | 72 |

A variant variable domain may differ from the variable domain of the humanized 5F11-45 or Y1238 sequence by up to 10 amino acids or any integral value between, where the variant variable domain specifically binds CD40. Alternatively, the variant variable domain may have at least 90% sequence identity (e.g., at least 92%, 95%, 98%, or 99% sequence identity) relative to the sequence of the humanized 5F11-45 or Y1238 sequence, respectively. Non-identical amino acid residues or amino acids that differ between two sequences may represent amino acid substitutions, additions, or deletions. Residues that differ between two sequences appear as non-identical positions, when the two sequences are aligned by any appropriate amino acid sequence alignment algorithm, such as BLAST® (a registered trademark of the U.S. National Library of Medicine).

Exemplary CD40 antibodies of the present invention can include an isolated antibody, or antigen binding portion thereof, that specifically binds to human CD40, wherein said antibody comprises a heavy chain and a light chain, wherein:

said heavy chain comprises a CDR1 comprising GYTFTDLSMHW (SEQ ID NO: 1), a CDR2 comprising YITPSSGYTAYNQKFKG (SEQ ID NO: 2), a CDR3 comprising LILQRGAY (SEQ ID NO: 3); and said light chain comprises a CDR1 comprising RASKNVDSYGNSFMHW (SEQ ID NO: 4), a CDR2 comprising RASNLES (SEQ ID NO: 5), and a CDR3 comprising QQSNEDPLT (SEQ ID NO: 6);

or said heavy chain comprises a CDR1 comprising GYAFTNYLIE (SEQ ID NO: 17), a CDR2 comprising VINPGSGGTNYNEKFKG (SEQ ID NO: 18), and a CDR3 comprising SQLGRRFDY (SEQ ID NO: 19); and said light chain comprises a CDR1 comprising KASQDVRTGVA (SEQ ID NO: 20), a CDR2 comprising SASYRNT (SEQ ID NO: 21), and a CDR3 comprising QQHYSPPYT (SEQ ID NO: 22).

In one specific embodiment, an antibody or antigen binding portion thereof, that specifically binds to human CD40, comprises (1) a heavy chain comprising a CDR1 comprising GYTFTDLSMHW (SEQ ID NO: 1), a CDR2 comprising YITPSSGYTAYNQKFKG (SEQ ID NO: 2), a CDR3 comprising LILQRGAY (SEQ ID NO: 3); and/or (2) comprises a light chain comprising a CDR1 comprising RASKNVDSYGNSFMHW (SEQ ID NO: 4), a CDR2 comprising RASNLES (SEQ ID NO: 5), and a CDR3 comprising QQSNEDPLT (SEQ ID NO: 6). Optionally, such antibody or antigen binding portion thereof comprises (1) a variable heavy chain of SEQ ID NO: 7; and/or (2) a light variable chain of SEQ ID NO: 8. To illustrate, such antibody or antigen binding portion thereof comprises (1) a heavy chain comprising the variable heavy chain of SEQ ID NO: 7; and (2) a light chain comprising the variable light chain of SEQ ID NO: 8.

An antibody or antigen binding portion thereof, that specifically binds to human CD40 can comprise a heavy chain comprising the variable heavy chain of SEQ ID NO: 7, and a light chain comprising the variable light chain of SEQ ID NO: 8, wherein the heavy chain comprises an Fc domain comprising the amino acid sequence of SEQ ID NO: 9 or SEQ ID NO: 98. An antibody or antigen binding portion thereof, that specifically binds to human CD40 can comprise a heavy chain comprising the variable heavy chain of SEQ ID NO: 7, and a light chain comprising the variable light chain of SEQ ID NO: 8, wherein the heavy chain comprises an Fc domain comprising the amino acid sequence of SEQ ID NO: 10 or SEQ ID NO: 99.

An antibody or antigen binding portion thereof, that specifically binds to human CD40 can comprise (1) a heavy chain comprising the amino acid sequence of SEQ ID NO: 85, SEQ ID NO: 106, 107, or 108; and (2) a light chain comprising the amino acid sequence of SEQ ID NO: 88. To illustrate, such antibody or antigen binding portion thereof comprises (1) a heavy chain comprising the amino acid sequence of SEQ ID NO: 85; and (2) a light chain comprising the amino acid sequence of SEQ ID NO: 88.

The isolated antibody or antigen binding portion thereof can antagonize activities of CD40. The isolated antibody or antigen binding portion thereof can be a chimeric antibody. The isolated antibody or antigen binding portion thereof can be a humanized antibody. The isolated antibody or antigen binding portion thereof can comprise a human heavy chain constant region and a human light chain constant region.

The isolated antibody or antigen binding portion thereof described herein can comprise a human IgG1 Fc domain comprising a mutation at Kabat position 238 that reduces binding to Fc-gamma-receptors (FcgRs), wherein proline 238 (P238) is mutated to one of the residues selected from the group consisting of lysine (K), serine (S), alanine (A), arginine (R) and tryptophan (W), and wherein the antibody or antigen binding portion thereof has reduced FcgR binding. The isolated antibody or antigen binding portion thereof described herein can have P238 mutated to lysine in a human IgG1 Fc domain.

The isolated antibody or antigen binding portion thereof comprises an Fc domain which comprises an amino acid sequence selected from:

EPKSCDKTHTCPPCPAPELLGGKSVFLFPPKPKDTLMISRTPEVTCVVVD
VSHEDPEVKFNWYVDGVEVHNAKTKPREEQYNSTYRVVSVLTVLHQDWLN
GKEYKCKVSNKALPAPIEKTISKAKGQPREPQVYTLPPSRDELTKNQVSL
TCLVKGFYPSDIAVEWESNGQPENNYKTTPPVLDSDGSFELYSKLTVDKS
RWQQGNVFSCSVMHEALHNHYTQKSLSLSPG (IgG1a-P238K (-C-
term Lys); SEQ ID NO: 98), EPKSCDKTHTCPPCPAPELLGGKSVFLFPPKPKDTLMISRTPEVTCVVVD
VSHEDPEVKFNWYVDGVEVHNAKTKPREEQYNSTYRVVSVLTVLHQDWLN
GKEYKCKVSNKALPAPIEKTISKAKGQPREPQVYTLPPSRDELTKNQVSL
TCLVKGFYPSDIAVEWESNGQPENNYKTTPPVLDSDGSPPLYSKLTVDKS
RWQQGNVFSCSVMHEALHNHYTQKSLSLSPGK (IgG1a-P238K;
SEQ ID NO: 9), ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVEP
KSCDKTHTCPPCPAPELLGGKSVFLFPPKPICDTLMISRTPEVTCVVVDV
SHEDPEVKFNWYVDGVEVHNAKTKPREEQYNSTYRVVSVLTVLHQDWLNG
KEYKCKVSNKALPAPIEKTISKAKGQPREPQVYTLPPSRDELTKNQVSLT
CLVKGFYPSDIAVEWESNGQPENNYKTTPPVLDSDGSFFLYSKLTVDKSR
WQQGNVFSCSVMHEALHNHYTQKSLSLSPG (CH1-IgG1a-P238K
(-C-term Lys); SEQ ID NO: 99), ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVEP
KSCDKTHTCPPCPAPELLGGKSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPGK (CH1-IgG1a-P238K;
SEQ ID NO: 10), EPKSCDKTHTCPPCPAPELLGGKSVFLFPPKPKDTLMISRTPEVTCVVVD
VSHEDPEVIKENWYVDGVEVHNAKTKPREEQYNSTYRVVSVLTVLHQDWL
NGKEYKCKVSNKALPAPIEKTISKAKGQPREPQVYTLPPSREEMTKNQVS
LTCLVKGFYPSDIAVEWESNGQPENNYKTTPPVLDSDGSFFLYSKLTVDK
SRWQQGNVFSCSVMHEALHNHYTQKSLSLSPG (IgG1f-P238K (-C-
term Lys); SEQ ID NO: 100), EPKSCDKTHTCPPCPAPELLGGKSVFLFPPKPKDTLMISRTPEVTCVVVD
VSHEDPEVKFNWYVDGVEVHNAKTKPREEQYNSTYRVVSVLTVLHQDWLN
GKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKS
RWQQGNVFSCSVMHEALHNHYTQKSLSLSPGK (IgG1f-P238K; SEQ
ID NO: 11), ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVEP
KSCDKTHTCPPCPAPELLGGKSVFLFPPKPKDTLMISRTPEVTCVVVDVS
HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVESCSVMHEALFINHYTQKSLSLSPG (CH1-IgG1f-P238K
(-C-term Lys); SEQ ID NO: 101).
or

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGKSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVESCSVMHEALHNHYTQKSLSLSPGK (CH1-IgG1f-P238K;
SEQ ID NO: 12).

The isolated antibody or antigen binding portion thereof described herein can comprise a human IgG1 Fc domain comprising an alanine substituted at Kabat position 297. For example, the isolated antibody or antigen binding portion thereof comprises an Fc domain which comprises an amino acid sequence selected from:

EPKSCDKTHTCPPCPAPELLGGPSVFLFPPKPKDTLMISRTPEVTCVVVD

VSHEDPEVKFNWYVDGVEVHNAKTKPREEQYASTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVESCSVMHEALHNHYTQKSLSLSPG (IgG1a-N297A(-C-
term Lys); SEQ ID NO: 102),

EPKSCDKTHTCPPCPAPELLGGPSVFLFPPKPKDTLMISRTPEVTCVVVD

VSHEDPEVKFNWYVDGVEVHNAKTKPREEQYASTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVESCSVMHEALHNHYTQKSLSLSPGK (IgG1a-N297A; SEQ
ID NO: 13),

ASTKGPSVFPLAPSSKSTSGGTAALGCLVICDYFPEPVTVSWNSGALTSG

VHTFPAVLQSSGLYSLSSVVTVPSSSLGTQTYICNVNHKPSNTKVDKRVE

PKSCDKTHTCPPCPAPELLGGPSVFLFPPKPKDTLMISRTPEVTCVVVDV

SHEDPEVKFNWYVDGVEVHNAKTKPREEQYASTYRVVSVLTVLHQDWLNG

KEYKCKVSNKALPAPIEKTISKAKGQPREPQVYTLPPSRDELTKNQVSLT

CLVKGFYPSDIAVEWESNGQPENNYKTTPPVLDSDGSFELYSKLTVDKSR

WQQGNVESCSVMHEALHNHYTQKSLSLSPG (CH1-IgG1a-N297A
(-C-term Lys); SEQ ID NO: 103),

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYASTYRVVSVLTVLHQDWLNGK

EYKCKVSNKALPAPIEKTISKAKGQPREPQVYTLPPSRDELTKNQVSLTC

LVKGEYPSDIAVEWESNGQPENNYKTTPPVLDSDGSFFLYSKLTVDKSRW

QQGNVFSCSVMHEALHNHYTQKSLSLSPGK (CH1-IgG1a-N297A;
SEQ ID NO: 14),

EPKSCDKTHTCPPCPAPELLGGPSVFLFPPKPKDTLMISRTPEVTCVVVD

VSHEDPEVKFNWYVDGVEVHNAKTKPREEQYASTYRVVSVLTVLHQDWLN

GKEYKCKVSNKALPAPIEKTISKAKGQPREPQVYTLPPSREEMTKNQVSL

TCLVKGFYPSDIAVEWESNGQPENNYKTTPPVLDSDGSFPLYSKLTVDKS

RWQQGNVFSCSVMHEALHNHYTQKSLSLSPG (IgG1f-N297A(-C-
term Lys); SEQ ID NO: 104),

EPKSCDKTHTCPPCPAPELLGGPSVFLFPPKPKDTLMISRTPEVTCVVVD

VSHEDPEVKFNWYVDGVEVHNAKTKPREEQYASTYRVVSVLTVLHQDWLN

GKEYKCKVSNKALPAPIEKTISKAKGQPREPQVYTLPPSREEMTKNQVSL

TCLVKGFYPSDIAVEWESNGQPENNYKTTPPVLDSDGSFELYSKLTVDKS

RWQQGNVESCSVMHEALHNHYTQKSLSLSPGK (IgG1f-N297A; SEQ
ID NO: 15),

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYASTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFELYSKLTVDKSRW

QQGNVESCSVMHEALHNHYTQKSLSLSPG(CH1-IgG1f-N297A(-C-
term Lys); SEQ ID NO: 105),
or

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYASTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFELYSKLTVDKSRW

QQGNVESCSVMHEALHNHYTQKSLSLSPGK (CH1-IgG1f-N297A;
SEQ ID NO: 16).

The isolated antibody or antigen binding portion described herein, wherein the antibody comprises (1) a variable heavy chain ($V_H$) selected from the group consisting of: hz-HC1 (SEQ ID NO: 23), hz-HC2 (SEQ ID NO: 24), hz-HC3 (SEQ ID NO: 25), hz-HC4 (SEQ ID NO: 26), hz-HC5 (SEQ ID NO: 27), hz-HC6 (SEQ ID NO: 28), hz-HC7 (SEQ ID NO: 29), hz-HC8 (SEQ ID NO: 30), hz-HC9 (SEQ ID NO: 31), hz-HC10 (SEQ ID NO: 32), and hz-HC11 (SEQ ID NO: 33); and/or (2) a variable light chain ($V_L$) selected from the group consisting of: hz-LC1 (SEQ ID NO: 34), hz-LC2 (SEQ ID NO: 35), hz-LC3 (SEQ ID NO: 36), hz-LC4 (SEQ ID NO: 37), and hz-LC5 (SEQ ID NO: 38).

The isolated antibody or antigen binding portion thereof disclosed herein, wherein the antibody comprises a heavy chain amino acid sequence selected from SEQ ID NO: 39, SEQ ID NO: 40, SEQ ID NO: 42, and SEQ ID NO: 43.

The isolated antibody or antigen binding portion thereof disclosed herein, wherein the antibody comprises a light chain amino acid sequence selected from SEQ ID NO: 41 and SEQ ID NO: 44.

The isolated antibody or antigen binding portion thereof disclosed herein, wherein the antibody is selected from the group consisting of:
 a) Y1238-hz1-P238K having a heavy chain of SEQ ID NO: 39 and light chain of SEQ ID NO: 41;
 b) Y1238-hz1-N297A having a heavy chain of SEQ ID NO: 40 and light chain of SEQ ID NO: 41;
 c) Y1238-hz2-P238K having a heavy chain of SEQ ID NO: 42 and light chain of SEQ ID NO: 44; and
 d) Y1238-hz2-N297A having a heavy chain of SEQ ID NO: 43 and light chain of SEQ ID NO: 44.

The antibody or antigen binding portion thereof disclosed herein, wherein the antigen binding portion is selected from the group consisting of Fv, Fab, F(ab')2, Fab', dsFv, scFv, sc(Fv)2, diabodies, and scFv-Fc.

The antibody or antigen binding portion thereof disclosed herein can be an immunoconjugate wherein the antibody or antigen-binding portion thereof is linked to a therapeutic agent.

The antibody or antigen binding portion thereof disclosed herein can be a bispecific antibody, wherein the antibody or antigen-binding portion thereof is linked to a second functional moiety having a different binding specificity than said antibody or antigen binding portion thereof.

The antibody or antigen binding portion thereof disclosed herein further comprising an additional moiety.

Fc Domain

The carboxy-terminal "half" of a heavy chain defines a constant region (Fc) and which is primarily responsible for effector function. As used herein, the term "Fc domain" refers to the constant region antibody sequences comprising CH2 and CH3 constant domains as delimited according to Kabat et al., *Sequences of Immunological Interest*, 5$^{th}$ ed., U.S. Dept. Health & Human Services, Washington, D.C. (1991). The Fc region may be derived from a human IgG. For instance, the Fc region may be derived from a human IgG1 or a human IgG4 Fc region. A heavy variable domain can be fused to an Fc domain. The carboxyl terminus of the variable domain may be linked or fused to the amino terminus of the Fc CH2 domain. Alternatively, the carboxyl terminus of the variable domain may be linked or fused to the amino terminus of a linker amino acid sequence, which itself is fused to the amino terminus of an Fc domain. Alternatively, the carboxyl terminus of the variable domain may be linked or fused to the amino terminus of a CH1 domain, which itself is fused to the Fc CH2 domain. Optionally, the protein may comprise the hinge region after the CH1 domain in whole or in part. Optionally an amino acid linker sequence is present between the variable domain and the Fc domain. The carboxyl terminus of the light variable domain may be linked or fused to the amino terminus of a CL domain.

An exemplary sequence for a heavy chain CH1 is amino acids 118-215 of SEQ ID NO: 85. An exemplary sequence for a light chain CL is amino acids 112-218 of SEQ ID NO: 88.

The antibody can be a fusion antibody comprising a first variable domain that specifically binds human CD40, and a second domain comprising an Fc domain.

Exemplary Fc domains used in the fusion protein can include human IgG domains. Exemplary human IgG Fc domains include IgG4 Fc domain and IgG1 Fc domain. While human IgG heavy chain genes encode a C-terminal lysine, the lysine is often absent from endogenous antibodies as a result of cleavage in blood circulation. Antibodies having IgG heavy chains including a C-terminal lysine, when expressed in mammalian cell cultures, may also have variable levels of C-terminal lysine present (Cai et al, 2011, *Biotechnol Bioeng.* 108(2):404-12). Accordingly, the C-terminal lysine of any IgG heavy chain Fc domain disclosed herein may be omitted.

The isolated antibody or antigen binding portion thereof described herein, can comprise an Fc domain which comprises an amino acid sequence of:

```
EPKSCDKTHTCPPCPAPELLGG(P/K)SVFLEPPKPKDTLMISRTPEVT

CVVVDVSHEDPEVKFNWYVDGVEVHNAKTKPREEQY(N/A)STYRVVSV

LTVLHQDWLNGKEYKCKVSNKALPAPIEKTISKAKGQPREPQVYTLPPS

R(D/E)E(L/M)TKNQVSLTCLVKGEYPSDIAVEWESNGQPENNYKTTP

PVLDSDGSFELYSKLTVDKSRWQQGNVFSCSVMHEALHNHYTQKSLSLS

PG(K/not present) (Fc consensus; SEQ ID NO: 112).
```

The Fc domain can comprise an amino acid sequence selected from the sequences in TABLE 4. SEQ ID NOS: 10, 12, 14, 16, 99, 101, 103 and 105 comprise a CH1 domain at the N-terminal (residues 1-98).

TABLE 4

| Sequence | SEQ ID NO |
|---|---|
| EPKSCDKTHTCPPCPAPELLGG<u>K</u>SVFLFPPKPKDTLMISRT PEVTCVVVDVSHEDPEVKFNWYVDGVEVHNAKTKPREE QYNSTYRVVSVLTVLHQDWLNGKEYKCKVSNKALPAPIE KTISKAKGQPREPQVYTLPPSRDELTKNQVSLTCLVKGFY PSDIAVEWESNGQPENNYKTTPPVLDSDGSFFLYSKLTVD KSRWQQGNVFSCSVMHEALHNHYTQKSLSLSPG (IgG1a-P238K; no C-terminal lysine) | 98 |
| EPKSCDKTHTCPPCPAPELLGG<u>K</u>SVFLFPPKPKDTLMISRT PEVTCVVVDVSHEDPEVKFNWYVDGVEVHNAKTKPREE QYNSTYRVVSVLTVLHQDWLNGKEYKCKVSNKALPAPIE KTISKAKGQPREPQVYTLPPSRDELTKNQVSLTCLVKGFY PSDIAVEWESNGQPENNYKTTPPVLDSDGSFFLYSKLTVD KSRWQQGNVFSCSVMHEALHNHYTQKSLSLSPGK (IgG1a-P238K) | 9 |
| ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKRVEPKSCDKTHTCPPCPAPELLGG KSVFLFPPKPKDTLMISRTPEVTCVVVDVSHEDPEVKFNW YVDGVEVHNAKTKPREEQYNSTYRVVSVLTVLHQDWLN GKEYKCKVSNKALPAPIEKTISKAKGQPREPQVYTLPPSR DELTKNQVSLTCLVKGFYPSDIAVEWESNGQPENNYKTT PPVLDSDGSFELYSKLTVDKSRWQQGNVFSCSVMHEALH NHYTQKSLSLSPG (CH1-IgG1a-P238K; no C-terminal lysine) | 99 |
| ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKRVEPKSCDKTHTCPPCPAPELLGG KSVFLFPPKPKDTLMISRTPEVTCVVVDVSHEDPEVKFNW YVDGVEVHNAKTKPREEQYNSTYRVVSVLTVLHQDWLN GKEYKCKVSNKALPAPIEKTISKAKGQPREPQVYTLPPSR DELTKNQVSLTCLVKGFYPSDIAVEWESNGQPENNYKTT PPVLDSDGSFFLYSKLTVDKSRWQQGNVFSCSVMHEALH NHYTQKSLSLSPGK (CH1-IgG1a-P238K) | 10 |
| EPKSCDKTHTCPPCPAPELLGG<u>K</u>SVFLFPPKPKDTLMISRT PEVTCVVVDVSHEDPEVKFNWYVDGVEVHNAKTKPREE QYNSTYRVVSVLTVLHQDWLNGKEYKCKVSNKALPAPIE KTISKAKGQPREPQVYTLPPSREEMTKNQVSLTCLVKGFY | 100 |

TABLE 4-continued

| Sequence | SEQ ID NO |
|---|---|
| PSDIAVEWESNGQPENNYKTTPPVLDSDGSFFLYSKLTVD KSRWQQGNVFSCSVMHEALHNHYTQKSLSLSPG (IgG1f-P238K; no C-terminal lysine) | |
| EPKSCDKTHTCPPCPAPELLGG<u>K</u>SVFLFPPKPKDTLMISRT PEVTCVVVDVSHEDPEVKFNWYVDGVEVHNAKTKPREE QYNSTYRVVSVLTVLHQDWLNGKEYKCKVSNKALPAPIE KTISKAKGQPREPQVYTLPPSREEMTKNQVSLTCLVKGFY PSDIAVEWESNGQPENNYKTTPPVLDSDGSFFLYSKLTVD KSRWQQGNVFSCSVMHEALHNHYTQKSLSLSPGK (IgG1f-P238K) | 11 |
| ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKRVEPKSCDKTHTCPPCPAPELLGG <u>K</u>SVFLFPPKPKDTLMISRTPEVTCVVVDVSHEDPEVKFNW YVDGVEVHNAKTKPREEQYNSTYRVVSVLTVLHQDWLN GKEYKCKVSNKALPAPIEKTISKAKGQPREPQVYTLPPSR EEMTKNQVSLTCLVKGFYPSDIAVEWESNGQPENNYKTT PPVLDSDGSFFLYSKLTVDKSRWQQGNVFSCSVMHEALH NHYTQKSLSLSPG (CH1-IgG1f-P238K; no C-terminal lysine) | 101 |
| ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKRVEPKSCDKTHTCPPCPAPELLGG <u>K</u>SVFLFPPKPKDTLMISRTPEVTCVVVDVSHEDPEVKFNW YVDGVEVHNAKTKPREEQYNSTYRVVSVLTVLHQDWLN GKEYKCKVSNKALPAPIEKTISKAKGQPREPQVYTLPPSR EEMTKNQVSLTCLVKGFYPSDIAVEWESNGQPENNYKTT PPVLDSDGSFFLYSKLTVDKSRWQQGNVFSCSVMHEALH NHYTQKSLSLSPGK (CH1-IgG1f-P238K) | 12 |
| EPKSCDKTHTCPPCPAPELLGG<u>P</u>SVFLFPPKPKDTLMISRT PEVTCVVVDVSHEDPEVKFNWYVDGVEVHNAKTKPREE QY<u>A</u>STYRVVSVLTVLHQDWLNGKEYKCKVSNKALPAPIE KTISKAKGQPREPQVYTLPPSRDELTKNQVSLTCLVKGFY PSDIAVEWESNGQPENNYKTTPPVLDSDGSFFLYSKLTVD KSRWQQGNVFSCSVMHEALHNHYTQKSLSLSPG (IgG1a-N297A; no C-terminal lysine) | 102 |
| EPKSCDKTHTCPPCPAPELLGG<u>P</u>SVFLFPPKPKDTLMISRT PEVTCVVVDVSHEDPEVKFNWYVDGVEVHNAKTKPREE QY<u>A</u>STYRVVSVLTVLHQDWLNGKEYKCKVSNKALPAPIE KTISKAKGQPREPQVYTLPPSRDELTKNQVSLTCLVKGFY PSDIAVEWESNGQPENNYKTTPPVLDSDGSFFLYSKLTVD KSRWQQGNVFSCSVMHEALHNHYTQKSLSLSPGK (IgG1a-N297A) | 13 |
| ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKRVEPKSCDKTHTCPPCPAPELLGG PSVFLFPPKPKDTLMISRTPEVTCVVVDVSHEDPEVKFNW YVDGVEVHNAKTKPREEQYASTYRVVSVLTVLHQDWLN GKEYKCKVSNKALPAPIEKTISKAKGQPREPQVYTLPPSR DELTKNQVSLTCLVKGFYPSDIAVEWESNGQPENNYKTT PPVLDSDGSFFLYSKLTVDKSRWQQGNVFSCSVMHEALH NHYTQKSLSLSPG (IgG1a-N297A; no C-terminal lysine) | 103 |
| ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKRVEPKSCDKTHTCPPCPAPELLGG PSVFLFPPKPKDTLMISRTPEVTCVVVDVSHEDPEVKFNW YVDGVEVHNAKTKPREEQYASTYRVVSVLTVLHQDWLN GKEYKCKVSNKALPAPIEKTISKAKGQPREPQVYTLPPSR DELTKNQVSLTCLVKGFYPSDIAVEWESNGQPENNYKTT PPVLDSDGSFFLYSKLTVDKSRWQQGNVFSCSVMHEALH NHYTQKSLSLSPGK (IgG1a-N297A) | 14 |
| EPKSCDKTHTCPPCPAPELLGG<u>P</u>SVFLFPPKPKDTLMISRT PEVTCVVVDVSHEDPEVKFNWYVDGVEVHNAKTKPREE QY<u>A</u>STYRVVSVLTVLHQDWLNGKEYKCKVSNKALPAPIE KTISKAKGQPREPQVYTLPPSREEMTKNQVSLTCLVKGFY | 104 |
| PSDIAVEWESNGQPENNYKTTPPVLDSDGSFFLYSKLTVD KSRWQQGNVFSCSVMHEALHNHYTQKSLSLSPG (IgG1f-N297A; no C-terminal lysine) | |
| EPKSCDKTHTCPPCPAPELLGG<u>P</u>SVFLFPPKPKDTLMISRT PEVTCVVVDVSHEDPEVKFNWYVDGVEVHNAKTKPREE QY<u>A</u>STYRVVSVLTVLHQDWLNGKEYKCKVSNKALPAPIE KTISKAKGQPREPQVYTLPPSREEMTKNQVSLTCLVKGFY PSDIAVEWESNGQPENNYKTTPPVLDSDGSFFLYSKLTVD KSRWQQGNVFSCSVMHEALHNHYTQKSLSLSPGK (IgG1f-N297A) | 15 |
| ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKRVEPKSCDKTHTCPPCPAPELLGG PSVFLFPPKPKDTLMISRTPEVTCVVVDVSHEDPEVKFNW YVDGVEVHNAKTKPREEQY<u>A</u>STYRVVSVLTVLHQDWLN GKEYKCKVSNKALPAPIEKTISKAKGQPREPQVYTLPPSR EEMTKNQVSLTCLVKGFYPSD1AVEWESNGQPENNYKTT PPVLDSDGSFFLYSKLTVDKSRWQQGNVFSCSVMHEALH NHYTQKSLSLSPG (CH1-IgG1F-N297A; no C-terminal lysine) | 105 |
| ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKRVEPKSCDKTHTCPPCPAPELLGG PSVFLFPPKPKDTLMISRTPEVTCVVVDVSHEDPEVKFNW YVDGVEVHNAKTKPREEQY<u>A</u>STYRVVSVLTVLHQDWLN GKEYKCKVSNKALPAPIEKTISKAKGQPREPQVYTLPPSR EEMTKNQVSLTCLVKGFYPSDIAVEWESNGQPENNYKTT PPVLDSDGSFFLYSKLTVDKSRWQQGNVFSCSVMHEALH NHYTQKSLSLSPGK (CH1-IgG1F-N297 A) | 16 |

The variable regions of the present antibodies may optionally be linked to the Fc domain by an "amino acid linker" or "linker." For example, the C-terminus of a variable heavy chain domain may be fused to the N-terminus of an amino acid linker, and an Fc domain may be fused to the C-terminus of the linker. Although amino acid linkers can be any length and consist of any combination of amino acids, the linker length may be relatively short (e.g., five or fewer amino acids) to reduce interactions between the linked domains. The amino acid composition of the linker also may be adjusted to reduce the number of amino acids with bulky side chains or amino acids likely to introduce secondary structure. Suitable amino acid linkers include, but are not limited to, those up to 3, 4, 5, 6, 7, 10, 15, 20, or 25 amino acids in length. Representative amino acid linker sequences include GGGGS (SEQ ID NO: 73), and a linker comprising 2, 3, 4, or 5 copies of GGGGS (SEQ ID NOs: 74-77, respectively). TABLE 5 lists suitable linker sequences for use in the present disclosure.

TABLE 5

| Representative Linker Sequences | |
|---|---|
| GGGGS | SEQ ID NO: 73 |
| (GGGGS)$_2$ | SEQ ID NO: 74 |
| (GGGGS)$_3$ | SEQ ID NO: 75 |
| (GGGGS)$_4$ | SEQ ID NO: 76 |
| (GGGGS)$_5$ | SEQ ID NO: 77 |
| AST | SEQ ID NO: 78 |

| TABLE 5-continued |  |
|---|---|
| Representative Linker Sequences |  |
| TVAAPS | SEQ ID NO: 79 |
| TVA | SEQ ID NO: 80 |
| ASTSGPS | SEQ ID NO: 97 |

Antibody Preparation

The antibody can be produced and purified using ordinary skill in a suitable mammalian host cell line, such as CHO, 293, COS, NSO, and the like, followed by purification using one or a combination of methods, including protein A affinity chromatography, ion exchange, reverse phase techniques, or the like.

As well known in the art, multiple codons can encode the same amino acid. Nucleic acids encoding a protein sequence thus include nucleic acids having codon degeneracy. The polypeptide sequences disclosed herein can be encoded by a variety of nucleic acids. The genetic code is universal and well known. Nucleic acids encoding any polypeptide sequence disclosed herein can be readily conceived based on conventional knowledge in the art as well as optimized for production. While the possible number of nucleic acid sequence encoding a given polypeptide is large, given a standard table of the genetic code, and aided by a computer, the ordinarily skilled artisan can easily generate every possible combination of nucleic acid sequences that encode a given polypeptide.

A representative nucleic acid sequence coding a 5F11-45 heavy chain variable domain is:

```
                                   (SEQ ID NO: 113)
caggtgcagctggtgcagtctggggctgaggtgaagaagcctgggtcctc ggtgaaggtctcctgcaaggcttctggatacaccttcactgacttatcga tgcactgggtgcgacaggcccctggacaagggcttgagtggatgggatac attactcctagcagtggatatactgcgtacaatcagaagttcaagggcaa gaccacgttgaccgcggacaaatccacgagcacagcctacatggagctga gcagcctgagatctgaggacacggccgtgtattactgtgcgagattgatc ttacaacggggagcttactggggccagggaaccctggtcaccgtctcctc a.
```

In this sequence, nucleotides 76-105 encode CDR1, nucleotides 148-198 encode CDR2, and nucleotides 295-318 encode CDR3 of the 5F11-45 variable domain of the heavy chain.

A representative nucleic acid sequence coding a 5F11-45 light chain variable domain is:

```
                                   (SEQ ID NO: 114)
gacatcgtgctgacccagtctccagactcctggctgtgtctctgggcgag agggccaccatcaactgcagagccagtaaaaatgttgatagttatggcaat agttttatgcactggtaccagcagaaaccaggacagcctcctaagctgtc atttaccgtgcatccaacctagaatctggggtccctgaccgattcagtggc agcgggtctgggacagatttcactctcaccatcagcagcctgcaggctgaa
```

```
gatgtggcagtttattactgtcagcaaagtaatgaggatcctctcacgttt ggccaggggaccaagctggagatcaaa.
```

In this sequence, nucleotides 70-117 encode CDR1, nucleotides 160-180 encode CDR2, and nucleotides 277-303 encode CDR3 of the 5F11-45 variable domain of the light chain.

A representative nucleic acid sequence coding a 5F11-45 heavy chain comprising a P238K Fc domain is:

```
                                   (SEQ ID NO: 115)
caggtgcagctggtgcagtctggggctgaggtgaagaagcctgggtcctc ggtgaaggtctcctgcaaggcttctggatacaccttcactgacttatcga tgcactgggtgcgacaggcccaggacaagggcttgagtggatgggataca ttactcctagcagtggatatactgcgtacaatcagaagttcaagggcaag accacgttgaccgcggacaaatccacgagcacagcctacatggagctgag cagcctgagatctgaggacacggccgtgtattactgtgcgagattgatct tacaacggggagcttactggggccagggaaccctggtcaccgtctcctca gctagcaccaagggcccatcggtcttcccctggcaccctcctccaagag cacctctgggggcacagcggccctgggctgcctggtcaaggactacttcc ccgaaccggtgacggtgtcgtggaactcaggcgccctgaccagcggcgtg cacaccttcccggctgtcctacagtcctcaggactctactccctcagcag cgtggtgaccgtgccctccagcagcttgggcacccagacctacatctgca acgtgaatcacaagcccagcaacaccaaggtggacaagagagttgagccc aaatcagtgacaaaactcacacatgcccaccgtgcccagcacctgaactc ctggggggaaagtcagtcttcctcttccccccaaaacccaaggacaccct catgatctcccggacccctgaggtcacatgcgtggtggtggacgtgagcc acgaagaccctgaggtcaagttcaactggtacgtggacggcgtggaggtg cataatgccaagacaaagccgcgggaggagcagtacaacagcacgtaccg tgtggtcagcgtcctcaccgtcctgcaccaggactggctgaatggcaagg agtacaagtgcaaggtctccaacaaagccctcccagcccccatcgagaaa accatctccaaagccaaagggcagccccgagaaccacaggtgtacaccct gcccccatcccgggatgagctgaccaagaaccaggtcagcctgacctgcc tggtcaaaggcttctatcccagcgacatcgccgtggagtgggagagcaat gggcagccggagaacaactacaagaccacgcctcccgtgctggactccga cggctccttcttcctctacagcaagctcaccgtggacaagagcaggtggc agcaggggaacgtcttctcatgctccgtgatgcatgaggctctgcacaac cactacacgcagaagagcctctccctgtctccgggt.
```

In this sequence, nucleotides 1-351 encode the variable domain of the heavy chain. Nucleotides 352-645 encode the CH1 domain, and nucleotides 646-1338 encode the Fc domain. Optionally, a codon for lysine can be added to 3' end of the Fc domain sequence.

A representative nucleic acid sequence coding a 5F11-45 light chain is:

(SEQ ID NO: 116)
gacatcgtgctgacccagtctccagactccctggctgtgtctctgggcga gagggccaccatcaactgc<u>agagccagtaaaaatgttgatagttatggca</u>

<u>atagttttatgcactgg</u>taccagcagaaaccaggacagcctcctaagctg ctcatttacc<u>gtgcatccaacctagaatct</u>ggggtccctgaccgattcag tggcagcgggtctgggacagatttcactctcaccatcagcagcctgcagg ctgaagatgtggcagtttattactgt<u>cagcaaagtaatgaggatcctctc</u>

<u>acg</u>tttggccaggggaccaagctggagatcaaacgtacggtggctgcacc atctgtcttcatcttcccgccatctgatgagcagttgaaatctggaactg cctctgagtgtgcctgctgaataacttctatcccagagaggccaaagtac agtggaaggtggataacgccctccaatcgggtaactcccaggagagtgtc acagagcaggacagcaaggacagcacctacagcctcagcagcaccctgac gctgagcaaagcagactacgagaaacacaaagtctacgcctgcgaagtca cccatcagggcctgagctcgcccgtcacaaagagcttcaacaggggagag tgt.

In this sequence, nucleotides 1-333 encode the variable domain of the light chain, and nucleotides 334-654 encode CL.

The coding sequence for the heavy and/or light chain may encode a signal peptide, such as MRAWIFFLLCLAGRALA (SEQ ID NO: 119), at the 5' end of the coding sequence. Exemplary coding sequences for a 5F11-45 heavy chain and light chain, each including a signal peptide coding sequence, are:

(SEQ ID NO: 117)
atgagggcttggatcactttctgctctgcctggccgggagagcgctcgca caggtgcagctggtgcagtctggggctgaggtgaagaagcctgggtcctc ggtgaaggtacctgcaaggcttctggatacaccttcactgacttatcgat gcactgggtgcgacaggcccctggacaagggcttgagtggatgggataca ttactcctagcagtggatatactgcgtacaatcagaagttcaagggcaag accacgttgaccgcggacaaatccacgagcacagcctacatggagctgag cagcctgagatctgaggacacggccgtgtattactgtgcgagattgatct tacaacggggagcttactggggccagggaaccctggtcaccgtctcctca gctagcaccaagggcccatcggtcttccccctggcaccctcctccaagag cacctctgggggcacagcggccctgggctgcctggtcaaggactacttcc ccgaaccggtgacggtgtcgtggaactcaggcgccctgaccagcggcgtg cacaccaccggccgtcctacagtcctcaggactctactccctcagcagc gtggtgaccgtgccctccagcagatgggcacccagacctacatctgcaac gtgaatcacaagcccagcaacaccaaggtggacaagagagttgagcccaa atcttgtgacaaaactcacacatgcccaccgtgcccagcacctgaactcc tggggggaaagtcagtcttcctcttcccccaaaacccaaggacaccctc atgatctcccggacccctgaggtcacatgcgtggtggtggacgtgagcca cgaagaccctgaggtcaagttcaactggtacgtggacggcgtggaggtgc ataatgccaagacaaagccgcgggaggagcagtacaacagcacgtaccgt -continued
gtggtcagcgtcctcaccgtcctgcaccaggactggctgaatggcaagga gtacaagtgcaaggtctccaacaaagccctcccagcccccatcgagaaaa ccatctccaaagccaaagggcagccccgagaaccacaggtgtacaccctg cccccatcccgggatgagctgaccaagaaccaggtcagcctgacctgcct ggtcaaaggcttctatcccagcgacatcgccgtggagtgggagagcaatg ggcagccggagaacaactacaagaccacgcctcccgtgctggactccgac ggctccttcttcctctacagcaagctcaccgtggacaagagcaggtggca gcaggggaacgtcttctcatgctccgtgatgcatgaggctctgcacaacc actacacgcagaagagcctctccctgtaccgggt and (SEQ ID NO: 118)
atgagggcttggatcttctttctgctctgcctggccgggcgcgccttggc cgacatcgtgctgacccagtctccagactccctggctgtgtctctgggcg agagggccaccatcaactgcagagccagtaaaaatgttgatagttatggc aatagttttatgcactggtaccagcagaaaccaggacagcctcctaagct gctcatttaccgtgcatccaacctagaatctggggtccctgaccgattca gtggcagcgggtctgggacagatttcactctcaccatcagcagcctgcag gctgaagatgtggcagtttattactgtcagcaaagtaatgaggatcctct cacgtttggccaggggaccaagctggagatcaaacgtacggtggctgcac catctgtcttcatcttcccgccatctgatgagcagttgaaatctggaact gcctctgttgtgtgcctgctgaataacttctatcccagagaggccaaagt acagtggaaggtggataacgccctccaatcgggtaactcccaggagagtg tcacagagcaggacagcaaggacagcacctacagcctcagcagcaccctg acgctgagcaaagcagactacgagaaacacaaatctacgcctgcgaagtc acccatcagggcctgagctcgcccgtcacaaagagcttcaacaggggaga gtgt.

Accordingly, a nucleic acid encoding an antibody disclosed herein is also contemplated. Such a nucleic acid may be inserted into a vector, such as a suitable expression vector, e.g., pHEN-1 (Hoogenboom et al. (1991) Nucleic Acids Res. 19:4133-4137). Further provided is an isolated host cell comprising the vector and/or the nucleic acid.

The antibody of the disclosure can be produced and purified using only ordinary skill in any suitable mammalian host cell line, such as CHO (Chinese hamster ovary cells), 293 (human embryonic kidney 293 cells), COS cells, NSO cells, and the like, followed by purification using one or a combination of methods, including protein A affinity chromatography, ion exchange, reverse phase techniques, or the like.

Pharmaceutical Compositions and Methods of Treatment

A pharmaceutical composition comprises a therapeutically-effective amount of one or more antibodies and optionally a pharmaceutically acceptable carrier. Pharmaceutically acceptable carriers include, for example, water, saline, phosphate buffered saline, dextrose, glycerol, ethanol and the like, as well as combinations thereof. Pharmaceutically acceptable carriers can further comprise minor amounts of auxiliary substances, such as wetting or emulsifying agents, preservatives, or buffers that enhance the shelf-life or effectiveness of the fusion protein. The compositions can be formulated to provide quick, sustained, or delayed release of the active ingredient(s) after administration. Suitable pharmaceutical compositions and processes for preparing them are known in the art. See, e.g., Remington, THE SCIENCE AND PRACTICE OF PHARMACY, A. Gennaro, et al., eds., 21st ed., Mack Publishing Co. (2005).

The pharmaceutical composition further may comprise an immunosuppressive/immunomodulatory and/or anti-inflammatory agent.

A method of treating an immune disease in a patient in need of such treatment may comprise administering to the patient a therapeutically effective amount of the antibody. Antagonizing CD40-mediated T cell activation could inhibit undesired T cell responses occurring during autoimmunity, transplant rejection, or allergic responses, for example. Inhibiting CD40-mediated T cell activation could moderate the progression and/or severity of these diseases.

Also provided is the use of an antibody of the disclosure, or a pharmaceutically acceptable salt thereof, in the preparation of a medicament for treatment of an immune disease in a patient in need of such treatment. The medicament can, for example, be administered in combination with an immunosuppressive/immunomodulatory and/or anti-inflammatory agent.

As used herein, a "patient" means an animal, e.g., mammal, including a human. The patient may be diagnosed with an immune disease. "Treatment" or "treat" or "treating" refers to the process involving alleviating the progression or severity of a symptom, disorder, condition, or disease. An "immune disease" refers to any disease associated with the development of an immune reaction in an individual, including a cellular and/or a humoral immune reaction. Examples of immune diseases include, but are not limited to, inflammation, allergy, autoimmune disease, or graft-related disease. An "autoimmune disease" refers to any disease associated with the development of an autoimmune reaction in an individual, including a cellular and/or a humoral immune reaction. An example of an autoimmune disease is inflammatory bowel disease (IBD), including, but not limited to ulcerative colitis and Crohn's disease. Other autoimmune diseases include systemic lupus erythematosus, multiple sclerosis, rheumatoid arthritis, diabetes, psoriasis, scleroderma, and atherosclerosis. Graft-related diseases include graft versus host disease (GVHD), acute transplantation rejection, and chronic transplantation rejection.

Diseases that can be treated by administering the antibody of the disclosure may be selected from the group consisting of Addison's disease, allergies, anaphylaxis, ankylosing spondylitis, asthma, atherosclerosis, atopic allergy, autoimmune diseases of the ear, autoimmune diseases of the eye, autoimmune hepatitis, autoimmune parotitis, bronchial asthma, coronary heart disease, Crohn's disease, diabetes, epididymitis, glomerulonephritis, Graves' disease, Guillain-Barre syndrome, Hashimoto's disease, hemolytic anemia, idiopathic thrombocytopenic purpura, inflammatory bowel disease, immune response to recombinant drug products (e.g., Factor VII in hemophiliacs), systemic lupus erythematosus, multiple sclerosis, myasthenia gravis, pemphigus, psoriasis, rheumatic fever, rheumatoid arthritis, sarcoidosis, scleroderma, Sjogren's syndrome, spondyloarthropathies, thyroiditis, transplant rejection, vasculitis, and ulcerative colitis.

The pharmaceutical composition may be administered alone or as a combination therapy, (i.e., simultaneously or sequentially) with an immunosuppressive/immunomodulatory and/or anti-inflammatory agent. Different immune diseases can require use of specific auxiliary compounds useful for treating immune diseases, which can be determined on a patient-to-patient basis. For example, the pharmaceutical composition may be administered in combination with one or more suitable adjuvants, e.g., cytokines (IL-10 and IL-13, for example) or other immune stimulators, e.g., chemokines, tumor-associated antigens, and peptides. Suitable adjuvants are known in the art.

Any suitable method or route can be used to administer the antibody or the pharmaceutical composition. Routes of administration include, for example, intravenous, intraperitoneal, subcutaneous, or intramuscular administration. A therapeutically effective dose of administered antibody depends on numerous factors, including, for example, the type and severity of the immune disease being treated, the use of combination therapy, the route of administration of the antibody or pharmaceutical composition, and the weight of the patient. A non-limiting range for a therapeutically effective amount of a domain antibody is 0.1-20 milligram/kilogram (mg/kg), and in an aspect, 1-10 mg/kg, relative to the body weight of the patient.

Kits

A kit useful for treating an immune disease in a human patient is provided. The kit can comprise (a) a dose of an antibody of the present disclosure and (b) instructional material for using the antibody in the method of treating an immune disease in a patient.

"Instructional material," as that term is used herein, includes a publication, a recording, a diagram, or any other medium of expression, which can be used to communicate the usefulness of the composition and/or compound of the invention in a kit. The instructional material of the kit may, for example, be affixed to a container that contains the compound and/or composition of the invention or be shipped together with a container, which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

EXAMPLES

Example 1: Fc-Formatting of Anti-CD40 Antibodies Impacts Activation of Immature Dendritic Cells Antibodies can be engineered to have different affinities and selectivity for FcgRs (FcγRs) by mutating the heavy chain constant region, such as in the hinge and Fc domain. Mutations can be introduced to either enhance or reduce FcgR binding. These mutations can increase or decrease FcgR-mediated cross-linking and/or signaling. For therapeutic targets such as CD40, FcgR-mediated cross-linking of anti-CD40 antibodies can has the potential to lead to undesirable agonist signaling and potential for toxicity. It is important to identify anti-CD40 antagonist antibodies that demonstrate reduced FcgR binding and potential for cross-linking and/or signaling, specifically, reduced engagement of the "low affinity" FcgRs hCD32a/FcgRIIa, hCD32b/FcgRIIb, hCD16a/FcgRIIIa, and hCD16b/FcgRIIIb. Engagement of the "high affinity" receptor CD64/FcgRI is generally believed to be of lower concern due to saturation of this receptor with serum IgG.

Antibody 5F11-45 is disclosed in U.S. Pat. Pub. 20160376371 (incorporated herein by reference) as a humanized antibody with high affinity to human CD40 that is engineered to have agonist activity, and the ability to bind preferentially to CD32a-R131 and CD32b. TABLE 6 below provides the amino acid sequences of the variable regions of the heavy and light chains of 5F11-45. In the heavy chain variable region, CDR1 is amino acids 26-35, CDR2 is amino acids 50-66, and CDR3 is amino acids 99-106. In the light chain variable region, CDR1 is amino acids 24-38, CDR2 is amino acids 54-60, and CDR3 is amino acids 93-101. The CDRs are underlined in each variable region.

To explore Fc formatting impact on activation of immature dendritic cells (iDC), the humanized anti-CD40 antibody 5F11-45 was formatted with a wild type human IgG1f isotype (5F11-45-IgG1f) as well as four isotypes with mutations designed to reduce FcgR binding (i.e., 5F11-45-IgG1.3f, 5F11-45-CTza, 5F11-45-P238K, 5F11-45-N297A). See SEQ ID NOS: 81-85 in TABLE 6. TABLE 6 further lists the heavy and light chain constant regions for each 5F11-45 antibody. The Fc domain is underlined in Table 6. The heavy chain variable region (amino acids 1-117) and the light chain variable region (amino acids 1-111) are in bolded font. The sequence (amino acids 118-215 of the heavy chain) between the variable region (in bolded font) and the Fc domain (underlined) comprises the CH1 domain in the heavy chain. The non-bolded sequence (amino acids 112-218) in the light chain comprises the CL domain.

TABLE 6

| Protein ID | HC | LC |
|---|---|---|
| 5F11-45 variable regions | QVQLVQSGAEVKKPGSSVKVSC KASGYTFTDLSMHWVRQAPGQ GLEWMGYITPSSGYTAYNQKFK GKTTLTADKSTSTAYMELSSLRS EDTAVYYCARLILQRGAYWGQG TLVTVSS SEQ ID NO: 7 | DIVLTQSPDSLAVSLGE RATINCRASKNVDSYGN SFMHWYQQKPGQPPKL LIYRASNLESGVPDRFS GSGSGTDFTLTISSLQAE DVAVYYCQQSNEDPLTF GQGTKLEIK SEQ ID NO: 8 |
| 5F11-45-IgG1f | QVQLVQSGAEVKKPGSSVKVSC KASGYTFTDLSMHWVRQAPGQ GLEWMGYITPSSGYTAYNQKFK GKTTLTADKSTSTAYMELSSLRS EDTAVYYCARLILQRGAYWGQG TLVTVSSASTKGPSVFPLAPSSKST SGGTAALGCLVKDYFPEPVTVSW NSGALTSGVHTFPAVLQSSGLYSL SSVVTVPSSSLGTQTYICNVNHKPS NTKVDKRVEPKSCDKTHTCPPCPA PELLGGPSVFLFPPKPKDTLMISRT PEVTCVVVDVSHEDPEVKFNWYV DGVEVHNAKTKPREEQYNSTYRV VSVLTVLHQDWLNGKEYKCKVSN KALPAPIEKTISKAKGQPREPQVYT LPPSREEMTKNQVSLTCLVKGFYP SDIAVEWESNGQPENNYKTTPPVL DSDGSFELYSKLTVDKSRWQQGN VFSCSVMHEALHNHYTQKSLSLSP GK SEQ ID NO: 81 | DIVLTQSPDSLAVSLGE RATINCRASKNVDSYGN SFMHWYQQKPGQPPKL LIYRASNLESGVPDRFS GSGSGTDFTLTISSLQAE DVAVYYCQQSNEDPLTF GQGTKLEIKRTVAAPSV FIFPPSDEQLKSGTASVVC LLNNFYPREAKVQWKVD NALQSGNSQESVTEQDS KDSTYSLSSTLTLSKADY EKHKVYACEVTHQGLSS PVTKSFNRGEC SEQ ID NO: 88 |
| 5F11-45-IgG1.3f | QVQLVQSGAEVKKPGSSVKVSC KASGYTFTDLSMHWVRQAPGQ GLEWMGYITPSSGYTAYNQKFK GKTTLTADKSTSTAYMELSSLRS EDTAVYYCARLILQRGAYWGQG TLVTVSSASTKGPSVFPLAPSSKST SGGTAALGCLVKDYFPEPVTVSW NSGALTSGVHTFPAVLQSSGLYSL SSVVTVPSSSLGTQTYICNVNHKPS NTKVDKRVEPKSCDKTHTCPPCPA PEAEGAPSVFLFPPKPKDTLMISRT PEVTCVVVDVSHEDPEVKFNWYV DGVEVHNAKTKPREEQYNSTYRV VSVLTVLHQDWLNGKEYKCKVSN KALPAPIEKTISKAKGQPREPQVYT LPPSREEMTKNQVSLTCLVKGFYP SDIAVEWESNGQPENNYKTTPPVL DSDGSFFLYSKLTVDKSRWQQGN VFSCSVMHEALHNHYTQKSLSLSP GK SEQ ID NO: 82 | DIVLTQSPDSLAVSLGE RATINCRASKNVDSYGN SFMHWYQQKPGQPPKL LIYRASNLESGVPDRFS GSGSGTDFTLTISSLQAE DVAVYYCQQSNEDPLTF GQGTKLEIKRTVAAPSV FIFPPSDEQLKSGTASVVC LLNNFYPREAKVQWKVD NALQSGNSQESVTEQDS KDSTYSLSSTLTLSKADY EKHKVYACEVTHQGLSS PVTKSFNRGEC SEQ ID NO: 88 |
| 5F11-45-CTza | QVQLVQSGAEVKKPGSSVKVSC KASGYTFTDLSNIHWVRQAPGQ GLEWMGYITPSSGYTAYNQKFK GKTTLTADKSTSTAYMELSSLRS EDTAVYYCARLILQRGAYWGQG | DIVLTQSPDSLAVSLGE RATINCRASKNVDSYGN SFMHWYQQKPGQPPKL LIYRASNLESGVPDRFS GSGSGTDFTLTISSLQAE |

TABLE 6-continued

| Protein ID | HC | LC |
|---|---|---|
| | TLVTVSSASTKGPSVFPLAPSSKST SGGTAALGCLVKDYFPEPVTVSW NSGALTSGVHTFPAVLQSSGLYSL SSVVTVPSSSLGTQTYICNVNHKPS NTKVDKKVEPKSCDKTHTSPPSPA PELLGGSSVFLFPPKPKDTLMISRT PEVTCVVVDVSHEDPEVKFNWYV DGVEVHNAKTKPREEQYNSTYRV VSVLTVLHQDWLNGKEYKCKVSN KALPAPIEKTISKAKGQPREPQVYT LPPSRDELTKNQVSLTCLVKGFYP SDIAVEWESNGQPENNYKTTPPVL DSDGSFFLYSKLTVDKSRWQQGN VFSCSVMHEALHNHYTQKSLSLSP GK SEQ ID NO: 83 | DVAVYYCQQSNEDPLTF GQGTKLEIKRTVAAPSV FIFPPSDEQLKSGTASVVC LLNNFYPREAKVQWKVD NALQSGNSQESVTEQDS KDSTYSLSSTLTLSKADY EKHKVYACEVTHQGLSS PVTKSFNRGEC SEQ ID NO: 88 |
| 5F11-45-N297A | QVQLVQSGAEVKKPGSSVKVSC KASGYTFTDLSMHWVRQAPGQ GLEWMGYITPSSGYTAYNQKFK GKTTLTADKSTSTAYMELSSLRS EDTAVYYCARLILQRGAYWGQG TLVTVSSASTKGPSVFPLAPSSKST SGGTAALGCLVKDYFPEPVTVSW NSGALTSGVHTFPAVLQSSGLYSL SSVVTVPSSSLGTQTYICNVNHKPS NTKVDKRVEPKSCDKTHTCPPCPA PELLGGPSVFLFPPKPKDTLMISRT PEVTCVVVDVSHEDPEVKFNWYV DGVEVHNAKTKPREEQYASTYRV VSVLTVLHQDWLNGKEYKCKVSN KALPAPIEKTISKAKGQPREPQVYT LPPSREEMTKNQVSLTCLVKGFYP SDIAVEWESNGQPENNYKTTPPVL DSDGSFFLYSKLTVDKSRWQQGN VFSCSVMHEALHNHYTQKSLSLSP GK SEQ ID NO: 84 | DIVLTQSPDSLAVSLGE RATINCRASKNVDSYGN SFMHWYQQKPGQPPKL LIYRASNLESGVPDRFS GSGSGTDFTLTISSLQAE DVAVYYCQQSNEDPLTF GQGTKLEIK**RTVAAPSV FIFPPSDEQLKSGTASVC LLNNFYPREAKVQWKVD NALQSGNSQESVTEQDS KDSTYSLSSTLTLSKADY EKHKVYACEVTHQGLSS PVTKSFNRGEC SEQ ID NO: 88 |
| 5F11-45-P238K | QVQLVQSGAEVKKPGSSVKVSC KASGYTFTDLSMHWVRQAPGQ GLEWMGYITPSSGYTAYNQKFK GKTTLTADKSTSTAYMELSSLRS EDTAVYYCARLILQRGAYWGQG TLVTVSSASTKGPSVFPLAPSSKST SGGTAALGCLVKDYFPEPVTVSW NSGALTSGVHTFPAVLQSSGLYSL SSVVTVPSSSLGTQTYICNVNHKPS NTKVDKRVEPKSCDKTHTCPPCPA PELLGGKSVFLFPPKPKDTLMISRT PEVTCVVVDVSHEDPEVKFNWYV DGVEVHNAKTKPREEQYNSTYRV VSVLTVLHQDWLNGKEYKCKVSN KALPAPIEKTISKAKGQPREPQVYT LPPSRDELTKNQVSLTCLVKGFYP SDIAVEWESNGQPENNYKTTPPVL DSDGSFFLYSKLTVDKSRWQQGN VFSCSVMHEALHNHYTQKSLSLSP GK SEQ ID NO: 85 | DIVLTQSPDSLAVSLGE RATINCRASKNVDSYGN SFMHWYQQKPGQPPKL LIYRASNLESGVPDRFS GSGSGTDFTLTISSLQAE DVAVYYCQQSNEDPLTF GQGTKLEIK**RTVAAPSV FIFPPSDEQLKSGTASVVC LLNNFYPREAKVQWKVD NALQSGNSQESVTEQDS KDSTYSLSSTLTLSKADY EKHKVYACEVTHQGLSS PVTKSFNRGEC SEQ ID NO: 88 |
| 5F11-45-SE | QVQLVQSGAEVKKPGSSVKVSC KASGYTFTDLSMHWVRQAPGQ GLEWMGYITPSSGYTAYNQKFK GKTTLTADKSTSTAYMELSSLRS EDTAVYYCARLILQRGAYWGQG TLVTVSSASTKGPSVFPLAPSSKST SGGTAALGCLVKDYFPEPVTVSW NSGALTSGVHTFPAVLQSSGLYSL SSVVTVPSSSLGTQTYICNVNHKPS NTKVDKRVEPKSCDKTHTCPPCPA PELLGGPSVFLFPPKPKDTLMISRT PEVTCVVVDVEHEDPEVKFNWYV DGVEVHNAKTKPREEQYNSTYRV VSVLTVLHQDWLNGKEYKCKVSN KALPAPIEKTISKAKGQPREPQVYT LPPSREEMTKNQVSLTCLVKGFYP | DIVLTQSPDSLAVSLGE RATINCRASKNVDSYGN SFIVIHWYQQKPGQPPKL LIYRASNLESGVPDRFS GSGSGTDFTLTISSLQAE DVAVYYCQQSNEDPLTF GQGTKLEIK**RTVAAPSV FIFPPSDEQLKSGTASVVC LLNNFYPREAKVQWKVD NALQSGNSQESVTEQDS KDSTYSLSSTLTLSKADY EKHKVYACEVTHQGLSS PVTKSFNRGEC SEQ ID NO: 88 |

TABLE 6-continued

| Protein ID | HC | LC |
|---|---|---|
| | SDIAVEWESNGQPENNYKTTPPVL<br>DSDGSFFLYSKLTVDKSRWQQGN<br>VFSCSVMHEALHNHYTQKSLSLSP<br>GK<br>SEQ ID NO: 86 | |
| 5F11-45-V11 | QVQLVQSGAEVKKPGSSVKVSC<br>KASGYTFTDLSMHWVRQAPGQ<br>GLEWMGYITPSSGYTAYNQKFK<br>GKTTLTADKSTSTAYMELSSLRS<br>EDTAVYYCARLILQRGAYWGQG<br>TLVTVSSASTKGPSVFPLAPSSKST<br>SGGTAALGCLVKDYFPEPVTVSW<br>NSGALTSGVHTFPAVLQSSGLYSL<br>SSVVTVPSSSLGTQTYICNVNHKPS<br>NTKVDKRVEPKSCDKTHTCPPCPA<br>PELLGDDSVFLFPPKPKDTLMISRT<br>PEVTCVVVDVSDEDGEVKFNWYV<br>DGVEVHNAKTKPREEQYNSTYRV<br>VSVLTVLHQDWLNGKEYKCKVSN<br>KALPRPIEKTISKAKGQPREPQVYT<br>LPPSREEMTKNQVSLTCLVKGFYP<br>SDIAVEWESNGQPENNYKTTPPVL<br>DSDGSFFLYSKLTVDKSRWQQGN<br>VFSCSVMHEALHNHYTQKSLSLSP<br>GK<br>SEQ ID NO: 87 | DIVLTQSPDSLAVSLGE<br>RATINCRASKNVDSYGN<br>SFMHWYQQKPGQPPKL<br>LIYRASNLESGVPDRFS<br>GSGSGTDFTLTISSLQAE<br>DVAVYYCQQSNEDPLTF<br>GQGTKLEIKRTVAAPSV<br>FIFPPSDEQLKSGTASVVC<br>LLNNFYPREAKVQWKVD<br>NALQSGNSQESVTEQDS<br>KDSTYSLSSTLTLSKADY<br>EKHKVYACEVTHQGLSS<br>PVTKSFNRGEC<br>SEQ ID NO: 88 |

As controls, the same 5F11-45 antibody was engineered for enhanced binding to human CD32a and CD32b proteins (5F11-45-SE; heavy (HC) and light chains (LC) are depicted as SEQ ID NOS: 86 and 88 respectively) or enhanced selectivity for hCD32b over hCD32a (5F11-45-V11; heavy and light chains are depicted SEQ ID NOS: 87 and 88 respectively).

All 5G11-45 Fc variants demonstrated high affinity binding to CD40 target by surface plasmon resonance (SPR) TABLE 7.

TABLE 7

SPR kinetic and affinity data for human-CD40 monomer binding to 5F11-45 antibodies captured on a protein A sensor chip surface.

| Sample | ka (1/Ms) | kd (1/s) | KD (nM) |
|---|---|---|---|
| 5F11-45-IgG1f | 6.9E+04 | 4.6E−04 | 6.7 |
| 5F11-45-SE | 7.1E+04 | 4.7E−04 | 6.6 |
| 5F11-45-V11 (n = 3) | 7.9 ± 0.6E+04 | 3.0 ± 1.4E−04 | 3.9 ± 2.1 |
| 5F11-45-IgG1.3f | 8.2E+04 | 1.3E−04 | 1.6 |
| 5F11-45-CTza | 8.8E+04 | 1.4E−04 | 1.6 |
| 5F11-45-N297A | 8.0E+04 | 2.2E−04 | 2.8 |
| 5F11-45-P238K | 7.9E+04 | 2.7E−04 | 3.3 |

The FcgR binding profiles of the Fc-engineered 5F11-45 antibodies were characterized by SPR to determine if the Fc mutations had the desired impacts on FcgR binding and selectivity. The SPR data for FcgR binding are shown in TABLE 8.

TABLE 8

% Rmax data for 1 μM or 10 μM 5F11-45 antibodies binding to anti-his Fab captured hFcgR-his proteins.

| Sample | Conc (μM) | hCD64 | hCD32a-H131 | hCD32a-R131 | hCD32b | hCD16a-V158 | hCD16b-NA2 |
|---|---|---|---|---|---|---|---|
| 5F11-45-IgG1f | 1 | 63% | 28% | 19% | 4% | 33% | 13% |
| 5F11-45-SE | 1 | 62% | 27% | 67% | 45% | 19% | 4% |
| 5F11-45-V11 | 1 | 37% | −3% | 29% | 54% | 2% | −7% |
| 5F11-45-IgG1.3f | 1 | 2% | 0% | 1% | 0% | 0% | 0% |
| 5F11-45-CTza | 1 | 60% | 0% | 0% | 0% | 1% | 0% |
| 5F11-45-N297A | 1 | 46% | 0% | 0% | 0% | 0% | 0% |
| 5F11-45-P238K | 1 | 46% | 0% | 0% | 0% | 0% | 0% |
| 5F11-45-IgG1f | 10 | 64% | 59% | 50% | 22% | 55% | 37% |
| 5F11-45-IgG1.3f | 10 | 12% | 1% | 9% | 4% | 1% | 1% |
| 5F11-45-CTza | 10 | 63% | 1% | 2% | 1% | 1% | 0% |
| 5F11-45-N297A | 10 | 58% | 0% | 0% | 0% | 1% | 0% |
| 5F11-45-P238K | 10 | 58% | 0% | 0% | 0% | 0% | 0% |

As shown in TABLE 8, 5F11-45-IgG1f binds to all FcgRs, with particularly strong binding to CD64, CD16a-V158, and CD32a-H131. The S267E variant (5F11-45-SE) (control) demonstrates the expected enhanced binding to CD32a and CD32b proteins. The five mutations present in the IgG1 V11 isotype of 5F11-45-V11 provided enhanced selectivity for CD32b.

The other four 5F11-45 Fc variants shown reduced FcgR binding. 5F11-45-IgG1.3f demonstrated reduced binding to all FcgRs including the weakest binding to CD64. At very high antibody concentrations (i.e., 10 µM), some weak binding of 5F11-45-IgG1.3f to CD32a-R131 is observed. In contrast, the other three variants (5F11-45-CTza, 5F11-45-P238K, and 5F11-45-N297A) demonstrated nearly undetectable binding to any of the low affinity FcgRs, even at a 10 µM antibody concentration. See TABLE 7 above. Differences were also observed in CD64 binding, especially in the dissociation rates, which were considerably faster for 5F11-45-P238K and 5F11-45-N297A compared to 5F11-45-CTza or 5F11-45-IgG1f, FIG. 1.

Immature dendritic cells (iDC) are sensitive to indirect activation of CD40 through clustering/cross-linking which can lead to activation of immature DCs leading to cytokine release (e.g., interleukin-6, Il-6) and cell surface activation signal upregulation (e.g., CD86 and CD54). Chinese hamster ovary (CHO) cells highly over-expressing CD32a, and having a low affinity to FcgR were used to demonstrate the potential for FcgR-mediated clustering/cross-linking. The ratio of CHO cells to iDCs is 1:6, representing an exaggerated level of clustering/cross-linking.

Figure 2:
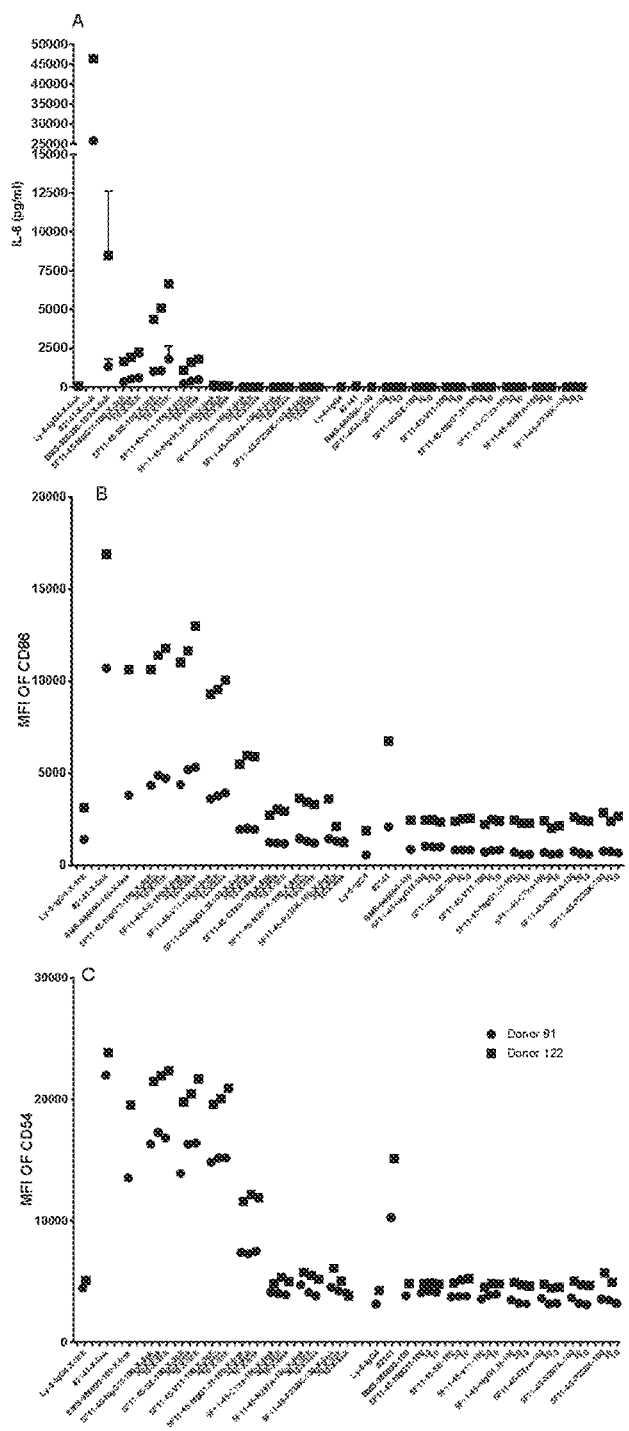
FIG. 2, comprising

BMS-986090 is an anti-CD40 antagonist domain antibody fused to IgG4 Fc domain and has the amino acid sequence:

(which is SEQ ID NO: 1287 in WO 2012/145673). The solid underlined portion of the BMS-986090 sequence corresponds to BMS3h-56-269 domain antibody (which is SEQ ID NO: 417 in WO 2012/145673). The dotted underline "AST" (SEQ ID NO: 78) is a linker and the rest is the Fc domain called IgG4.1. 2141 (mAb 134-2141) is a CD40 agonist antibody (see Robert Vonderheide et al., "Clinical Activity and Immune Modulation in Cancer Patients Treated with CP-870,893, a Novel CD40 Agonist Monoclonal Antibody," 25(7): 876-883 (2007)). BMS-986090 and 2141 were used as positive controls for cross-linking mediated anti-CD40 iDC activation. L6-IgG4, a fusion protein with no CD40 binding capability, served as a negative control. As seen in FIG. 2, 5F11-45-CTza, 5F11-45-P238K and 5F11-45-N297A show no cross-linking mediated anti-CD40 iDC activation as measured by increased cytokine (interleukin-6; Il-6; FIG. 2A) or activation marker increases (CD86 MFI; FIG. 2C and CD54 MFI; FIG. 2B) either when soluble or cross-linked/clustered by cell surface CD32. 5F11-45-IgG1.3f demonstrated modest iDC activation only when co-incubated with CD32 CHO cells, as indicated by increases in CD54 and CD86 cell surface staining. All of the variants which demonstrated binding to the low affinity FcgRs (i.e., 5F11-45-IgG1f, 5F11-45-SE and 5F11-45-V11) demonstrated iDC activation that was dramatically increased with the addition of CD32 CHO cells, FIG. 2. The 5F11-45 antibody formatted with CTza, P238K and N297A did not demonstrate any detectable iDC activation. These data support that 5F11-45 antibody formatted with CTza, P238K or N297A antagonizes CD40 activity.

To further assess these observations in other antibodies, a potent mouse anti-human-CD40 antibody Y1238 was formatted as a chimeric antibody with these isotypes and as IgG1.3f (SEQ ID NOS: 90-93 for the heavy chains and SEQ ID NO: 94 for the light chains). See TABLE 9. The heavy chain variable region is amino acids 1-118 (bolded font). In the heavy chain variable region, CDR1 is amino acids 26-36, CDR2 is amino acids 50-66, and CDR3 is amino acids 99-107. The Fc domain is amino acids 217-448. The sequence (amino acids 119-216 of the heavy chain) between the variable region (in bolded font) and the Fc domain (underlined) comprises the CH1 domain in the heavy chain. The light chain variable region is amino acids 1-107. In the light chain variable region, CDR1 is amino acids 24-34, CDR2 is amino acids 50-56, and CDR3 is amino acids 89-97. Amino acids 108-214 in the light chain comprise the CL domain.

(SEQ ID NO: 89)

EVQLLESGGGLVQPGGSLRLSCAASGFTFRDYEMWWVRQAPGKGLERVSAINPQG

TRTYYADSVKGRFTISRDNSKNTLYLQMNSLRAEDTAVYYCAKLPFRFSDRGQGTL

VTVSSASTESKYGPPCPPCPAPEFLGGPSVFLFPPKPKDTLMISRTPEVTCVVVDVSQ

EDPEVQFNWYVDGVEVHNAKTKPREEQFNSTYRVVSVLTVLHQDWLNGKEYKCK

VSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEGNVFS

CSVMHEALHNHYTQKSLSLSLGK,

TABLE 9

| Protein ID | Heavy Chain (HC) | Light Chain (LC) |
| --- | --- | --- |
| Y1238-IgG1.3f | QVQLQQSGAELVRPGTSVKVS CKASGYAFTNYLIEWVKQRPG QGLEWIGVINPGSGGTNYNEK FKGKATLTADKSSSTAYMQLS SLTSDDSAVYFCARSQLGRRF DYWGQGTTLTVSSASTKGPSV FPLAPSSKSTSGGTAALGCLVKD YFPEPVTVSWNSGALTSGVHTF PAVLQSSGLYSLSSVVTVPSSSL GTQTYICNVNHKPSNTKVDKRV EPKSCDKTHTCPPCPAPEAEGAP SVFLFPPKPKDTLMISRTPEVTC VVVDVSHEDPEVKFNWYVDGV EVHNAKTKPREEQYNSTYRVVS VLTVLHQDWLNGKEYKCKVSN KALPAPIEKTISKAKGQPREPQV YTLPPSREEMTKNQVSLTCLVK GFYPSDIAVEWESNGQPENNYK TTPPVLDSDGSFFLYSKLTVDKS RWQQGNVFSCSVMHEALHNHY TQKSLSLSPGK SEQ ID NO: 90 | DIVMTQSHKFMSTVG DRVSITCKASQDVRTGV AWYQQKPGQSPKLLIY SASYRNTGVPDRFTGSR SGTDFTFTISSVQAEDLA VYYCQQHYSPPYTFGG GTKLEIKRTVAAPSVFIF PPSDEQLKSGTASVVCLL NNFYPREAKVQWKVDN ALQSGNSQESVTEQDSK DSTYSLSSTLTLSKADYE KHKVYACEVTHQGLSSP VTKSFNRGEC SEQ ID NO: 94 |
| Y1238-CTza | QVQLQQSGAELVRPGTSVKVS CKASGYAFTNYLIEWVKQRPG QGLEWIGVINPGSGGTNYNEK FKGKATLTADKSSSTAYMQLS SLTSDDSAVYFCARSQLGRRF DYWGQGTTLTVSSASTKGPSV FPLAPSSKSTSGGTAALGCLVKD YFPEPVTVSWNSGALTSGVHTF PAVLQSSGLYSLSSVVTVPSSSL GTQTYICNVNHKPSNTKVDKKV EPKSCDKTHTSPPSPAPELLGGS SVFLFPPKPKDTLMISRTPEVTC VVVDVSHEDPEVKFNWYVDGV EVHNAKTKPREEQYNSTYRVVS VLTVLHQDWLNGKEYKCKVSN KALPAPIEKTISKAKGQPREPQV YTLPPSRDELTKNQVSLTCLVK GFYPSDIAVEWESNGQPENNYK TTPPVLDSDGSFFLYSKLTVDKS RWQQGNVFSCSVMHEALHNHY TQKSLSLSPGK SEQ ID NO: 91 | DIVMTQSHKFMSTVG DRVSITCKASQDVRTGV AWYQQKPGQSPKLLIY SASYRNTGVPDRFTGSR SGTDFTFTISSVQAEDLA VYYCQQHYSPPYTFGG GTKLEIKRTVAAPSVFIF PPSDEQLKSGTASVVCLL NNFYPREAKVQWKVDN ALQSGNSQESVTEQDSK DSTYSLSSTLTLSKADYE KHKVYACEVTHQGLSSP VTKSFNRGEC SEQ ID NO: 94 |
| Y1238-N297A | QVQLQQSGAELVRPGTSVKVS CKASGYAFTNYLIEWVKQRPG QGLEWIGVINPGSGGTNYNEK FKGKATLTADKSSSTAYMQLS SLTSDDSAVYFCARSQLGRRF DYWGQGTTLTVSSASTKGPSV FPLAPSSKSTSGGTAALGCLVKD YFPEPVTVSWNSGALTSGVHTF PAVLQSSGLYSLSSVVTVPSSSL GTQTYICNVNHKPSNTKVDKRV EPKSCDKTHTCPPCPAPELLGGP SVFLFPPKPKDTLMISRTPEVTC VVVDVSHEDPEVKFNWYVDGV EVHNAKTKPREEQYASTYRVVS VLTVLHQDWLNGKEYKCKVSN KALPAPIEKTISKAKGQPREPQV YTLPPSREEMTKNQVSLTCLVK GFYPSDIAVEWESNGQPENNYK TTPPVLDSDGSFFLYSKLTVDKS RWQQGNVFSCSVMHEALHNHY TQKSLSLSPGK SEQ ID NO: 92 | DIVMTQSHKFMSTVG DRVSITCKASQDVRTGV AWYQQKPGQSPKLLIY SASYRNTGVPDRFTGSR SGTDFTFTISSVQAEDLA VYYCQQHYSPPYTFGG GTKLEIKRTVAAPSVFIF PPSDEQLKSGTASVVCLL NNFYPREAKVQWKVDN ALQSGNSQESVTEQDSK DSTYSLSSTLTLSKADYE KIIKVYACEVTHQGLSSP VTKSFNRGEC SEQ ID NO: 94 |
| Y1238-P238K | QVQLQQSGAELVRPGTSVKVS CKASGYAFTNYLIEWVKQRPG QGLEWIGVINPGSGGTNYNEK FKGKATLTADKSSSTAYMQLS SLTSDDSAVYFCARSQLGRRF DYWGQGTTLTVSSASTKGPSV FPLAPSSKSTSGGTAALGCLVKD YFPEPVTVSWNSGALTSGVHTF PAVLQSSGLYSLSSVVTVPSSSL | DIVMTQSHKFMSTVG DRVSITCKASQDVRTGV AWYQQKPGQSPKLLIY SASYRNTGVPDRFTGSR SGTDFTFTISSVQAEDLA VYYCQQHYSPPYTFGG GTKLEIKRTVAAPSVFIF PPSDEQLKSGTASVVCLL NNFYPREAKVQWKVDN |

TABLE 9-continued

| Protein ID | Heavy Chain (HC) | Light Chain (LC) |
|---|---|---|
| | GTQTYICNVNHKPSNTKVDKRV<br>EPKSCDKTHTCPPCPAPELLGGK<br>SVFLEPPKPKDTLMISRTPEVTC<br>VVVDVSHEDPEVKFNWYVDGV<br>EVHNAKTKPREEQYNSTYRVVS<br>VLTVLHQDWLNGKEYKCKVSN<br>KALPAPIEKTISKAKGQPREPQV<br>YTLPPSRDELTKNQVSLTCLVK<br>GFYPSDIAVEWESNGQPENNYK<br>TTPPVLDSDGSFFLYSKLTVDKS<br>RWQQGNVFSCSVMHEALHNHY<br>TQKSLSLSPGK<br>SEQ ID NO: 93 | ALQSGNSQESVTEQDSK<br>DSTYSLSSTLTLSKADYE<br>KHKVYACEVTHQGLSSP<br>VTKSFNRGEC<br>SEQ ID NO: 94 |

These chimeric antibodies were tested for CD40 and FcgR binding by SPR, as well as for iDC activation. All of the Fc variant Y1238 chimeric antibodies demonstrated high affinity for human-CD40, TABLE 10.

TABLE 10

SPR kinetic and affinity data for human-CD40 monomer binding to chimeric Y1238 antibodies captured on a protein A sensor chip surface.

| Sample | ka (1/Ms) | kd (1/s) | KD (nM) |
|---|---|---|---|
| Y1238-hIgG1.3f | 1.0E+05 | 2.1E−04 | 2.1 |
| Y1238-CTza | 1.0E+05 | 2.3E−04 | 2.3 |
| Y1238-N297A | 9.7E+04 | 2.4E−04 | 2.5 |
| Y1238-P238K | 9.7E+04 | 2.6E−04 | 2.6 |

Like 5F11-45, the chimeric Y1238 antibodies with engineered Fc domains demonstrated much weaker FcgR binding as compared to the IgG1f isotype control. The Y1238-IgG1.3f molecule demonstrated some weak but measurable binding responses towards the low affinity FcgRs, in particular CD32a-R131 and CD32b. In contrast, the CTza, P238K and N297A variants had very weak or undetectable binding to these FcgRs, even at 10 μM antibody concentration, TABLE 11.

TABLE 11

% Rmax data for 1 μM or 10 μM chimeric Y1238 antibodies binding to anti-His Fab captured hFcgR-his proteins.

| Sample | Conc (μM) | hCD64 | hCD32a-H131 | hCD32a-R131 | hCD32b | hCD16a-V158 | hCD16b-NA2 |
|---|---|---|---|---|---|---|---|
| control-mAb-IgG1f | 1 | 63% | 33% | 23% | 5% | 37% | 16% |
| Y1238-hIgG1.3f | 1 | 7% | 0% | 5% | 2% | 1% | 0% |
| Y1238-CTza | 1 | 65% | 0% | 1% | 0% | 1% | 0% |
| Y1238-N297A | 1 | 57% | 0% | 0% | 0% | 1% | 0% |
| Y1238-P238K | 1 | 59% | 0% | 0% | 0% | 0% | 0% |
| control-mAb-IgG1f | 10 | 65% | 62% | 55% | 26% | 57% | 41% |
| Y1238-hIgG1.3f | 10 | 30% | 4% | 28% | 14% | 4% | 3% |
| Y1238-CTza | 10 | 66% | 3% | 7% | 4% | 4% | 0% |
| Y1238-N297A | 10 | 63% | 0% | 1% | 0% | 2% | 0% |
| Y1238-P238K | 10 | 64% | 0% | 0% | 0% | 0% | 0% |

CD64 binding was similar for the chimeric Y1238 antibodies as with the 5F11-45 variants, with IgG1.3f demonstrating the weakest CD64 binding. Both the P238K and N297A variants have significantly faster dissociation rates than CTza, whether in the Y1238 chimeric antibody form or in the 5F11-45.

Figure 3:
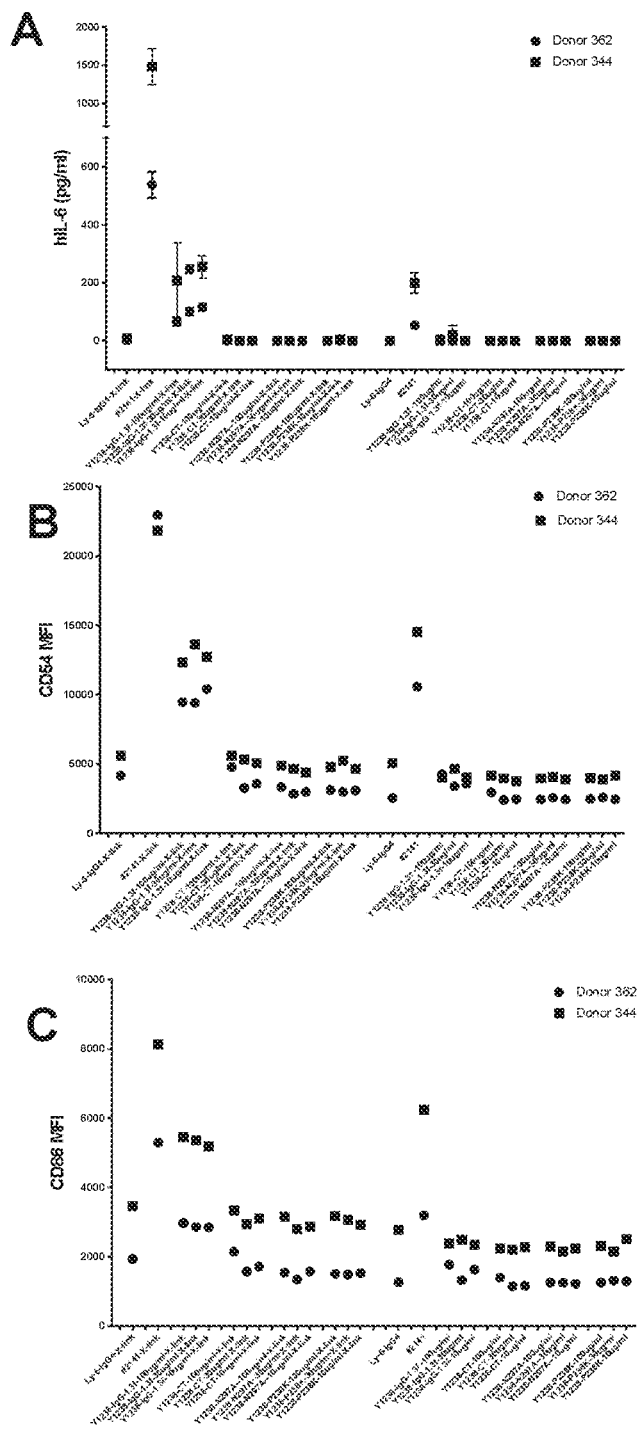
FIG. 3, comprising

Like 5F11-45, the chimeric Y1238 demonstrated no activation of iDC either alone or with the addition of FcgR (CD32) over expressing CHO cells when formatted with the CTza, P238K, or N297A isotypes, FIG. 3. Minimal activation was observed for chimeric. Y1238 with the IgG1.3f Fc sequence. However iDC cytokine release (FIG. 3A) and activation marker upregulation (FIGS. 3B and 3C) were increased with co-incubation with CD32 expressing CHO cells.

Figure 4:
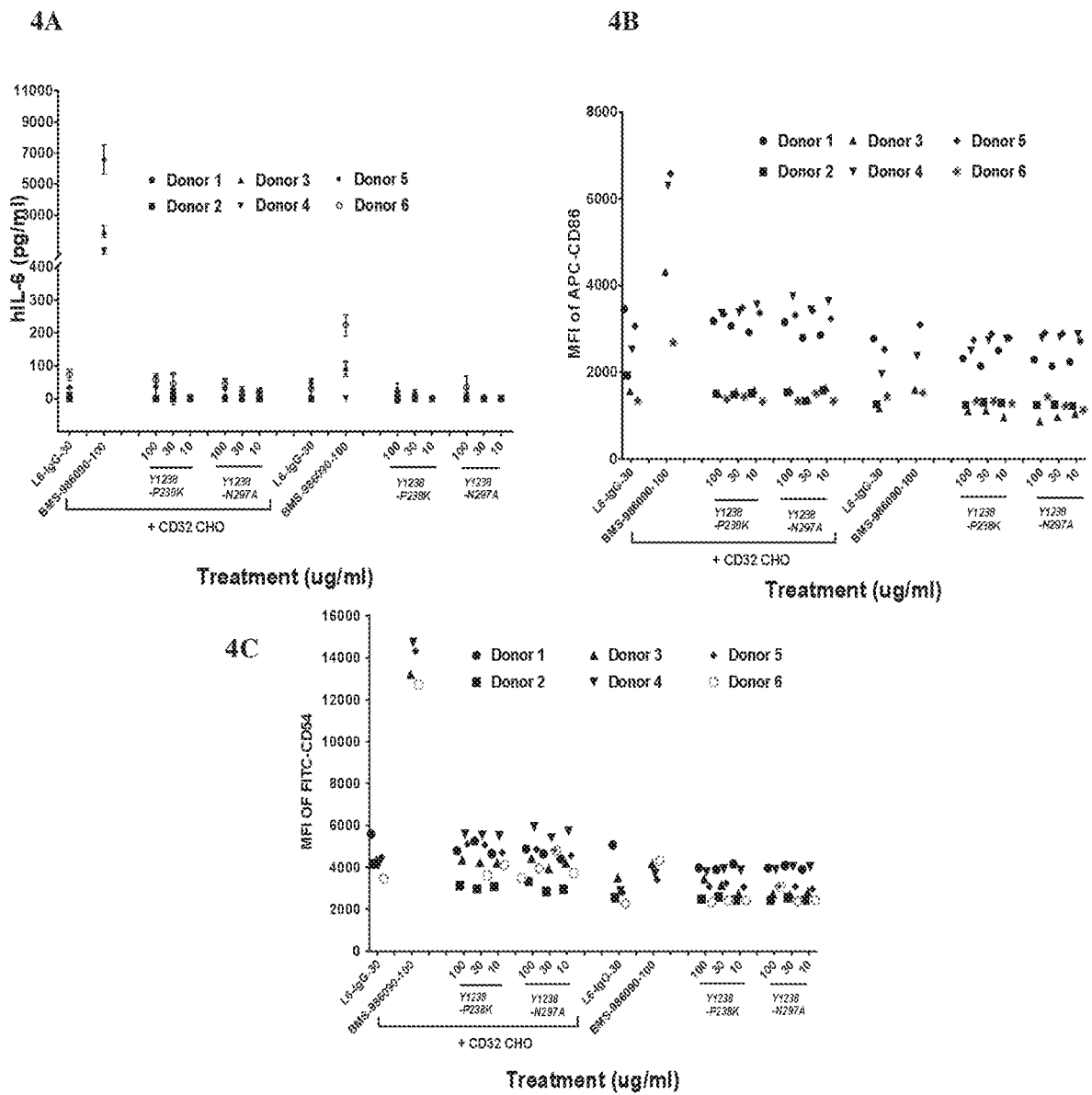
FIG. 4, comprising
Figure 5:
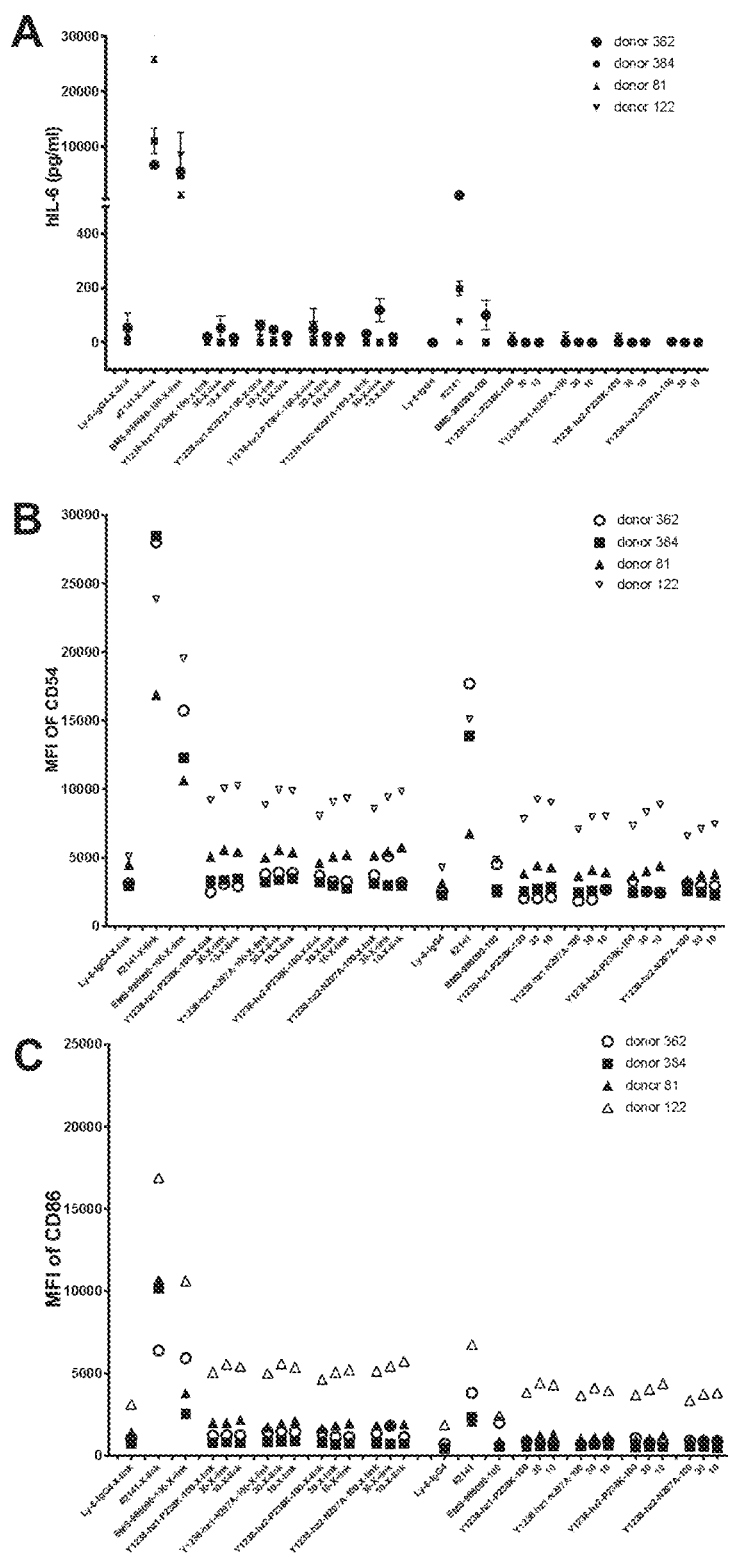
FIG. 5, comprising

Chimeric Y1238-P238K and Y1238-N297A were further tested in iDC from additional donors, confirming that these molecules do not activate immature dendritic cells either alone or in the addition of CD32 CHO cells, FIG. 4. The positive controls in these studies are BMS-986090 and 2141; both antibodies lead to iDC activation in cells from a subset of donors when used in solution (FIGS. 3 and 4). However, iDC activation was dramatically increased with CD32 CHO cell clustering/cross-linking, which was observed in cells from every donor tested under these conditions.

Example 2: Humanized CD40 Antagonist Antibody Y1238 Demonstrates Potent Inhibition of CD40 Signaling and No Agonist Signals when Formatted with Isotypes Containing P238K or N297A Mutations Humanization background/procedure is as discussed in section "II. Engineered and Modified Antibodies" in WO2017004006, which is incorporated herein by reference in its entirety. Based on this analysis, 11 $V_H$ sequences (SEQ ID NOS: 23-33) and 5 $V_K$ sequences (SEQ ID NOS: 34-38) were selected for testing. Substitutions are indicated in bold and by dotted underline. The CDRs in each variable heavy and variable light, in CDR1-CDR2-CDR3 orientation, are indicated by underlining, i.e., GYAFTNYLIE (SEQ ID NO:

17), VINPGSGGTNYNEKFKG (SEQ ID NO: 18), and SQLGRRFDY (SEQ ID NO: 19) respectively for the variable heavy CDRs (Table 12) and KASQDVRTGVA (SEQ ID NO: 20), SASYRNT (SEQ ID NO: 21), and QQHYSPPYT (SEQ ID NO: 22) for the variable light CDRs respectively (Table 13).

TABLE 12

Humanized Y1238 variable heavy sequences:

| SEQ ID NO: | Hz-HC# | ID | Sequence |
|---|---|---|---|
| 23 | hz-HC1 | h-Y1238_VH | QVQLVQSGAEVKKPGASVKVSCKAS<u>GY AFTNYLIE</u>WVRQAPGQGLEWMG<u>VINPG SGGTNYNEKFKG</u>RVTMTRDTSISTAYME LSRLRSDDTAVYYCAR<u>SQLGRRFDY</u>WG QGTLVTVSS |
| 24 | hz-HC2 | h-Y1238_VH_R72A | QVQLVQSGAEVKKPGASVKVSCKAS<u>GY AFTNYLIE</u>WVRQAPGQGLEWMG<u>VINPG SGGTNYNEKFKG</u>RVTMT<u>A</u>DTSISTAYME LSRLRSDDTAVYYCAR<u>SQLGRRFDY</u>WG QGTLVTVSS |
| 25 | hz-HC3 | h-Y1238_VH_T74K | QVQLVQSGAEVKKPGASVKVSCKAS<u>GY AFTNYLIE</u>WVRQAPGQGLEWMG<u>VINPG SGGTNYNEKFKG</u>RVTMTRD<u>K</u>SISTAYM ELSRLRSDDTAVYYCAR<u>SQLGRRFDY</u>W GQGTLVTVSS |
| 26 | hz-HC4 | h-Y1238_VH_R72A-T74K | QVQLVQSGAEVKKPGASVKVSCKAS<u>GY AFTNYLIE</u>WVRQAPGQGLEWMG<u>VINPG SGGTNYNEKFKG</u>RVTMT<u>ADK</u>SISTAYM ELSRLRSDDTAVYYCAR<u>SQLGRRFDY</u>W GQGTLVTVSS |
| 27 | hz-HC5 | h-Y1238_VH_A40R-R72A-T74K | QVQLVQSGAEVKKPGASVKVSCKAS<u>GY AFTNYLIE</u>WVRQ<u>R</u>PGQGLEWMG<u>VINPG SGGTNYNEKFKG</u>RVTMT<u>ADK</u>SISTAYM ELSRLRSDDTAVYYCAR<u>SQLGRRFDY</u>W GQGTLVTVSS |
| 28 | hz-HC6 | h-Y1238_VH_A40-M70L-R72A-T74K | QVQLVQSGAEVKKPGASVKVSCKAS<u>GY AFTNYLIE</u>WVRQ<u>R</u>PGQGLEWMG<u>VINPG SGGTNYNEKFKG</u>RVT<u>LTADK</u>SISTAYME LSRLRSDDTAVYYCAR<u>SQLGRRFDY</u>WG QGTLVTVSS |
| 29 | hz-HC7 | h-Y1238_VH_K12V-A40R-R72A-T74K-I76S-E82Q-Y95F | QVQLVQSGAEV<u>V</u>KPGASVKVSCKAS<u>GY AFTNYLIE</u>WVRQ<u>R</u>PGQGLEWMG<u>VINPG SGGTNYNEKFKG</u>RVTMT<u>ADKS</u>STAYM <u>Q</u>LSRLRSDDTAVY<u>F</u>CAR<u>SQLGRRFDY</u>W GQGTLVTVSS |

TABLE 12-continued

Humanized Y1238 variable heavy sequences:

| SEQ ID NO: | Hz-HC# | ID | Sequence |
|---|---|---|---|
| 30 | hz-HC8 | h-Y1238_VH_K12V-A40R-M70L-R72A-T74K-I76S-E82Q-Y95F | QVQLVQSGAEVVKPGASVKVSCKAS<u>GY</u><br><u>AFTNYLIE</u>WVRQRPGQGLEWMG<u>VINPG</u><br><u>SGGTNYNEKFKG</u>RVTLTADKSSTAYM<br>QLSRLRSDDTAVYFCAR<u>SQLGRRFDY</u>W<br>GQGTLVTVSS |
| 31 | hz-HC9 | h-Y1238_VH_K12V-A40R-M70L-R72A-T74K-I76S-E82Q-Y95F-L113T | QVQLVQSGAEVVKPGASVKVSCKAS<u>GY</u><br><u>AFTNYLIE</u>WVRQRPGQGLEWMG<u>VINPG</u><br><u>SGGTNYNEKFKG</u>RVTLTADKSSTAYM<br>QLSRLRSDDTAVYFCAR<u>SQLGRRFDY</u>W<br>GQGTLVTVSS |
| 32 | hz-HC10 | h-Y1238_VH_A410R-T74K | QVQLVQSGAEVKKPGASVKVSCKAS<u>GY</u><br><u>AFTNYLIE</u>WVRQRPGQGLEWMG<u>VINPG</u><br><u>SGGTNYNEKFKG</u>RVTMTRDKSISTAYM<br>ELSRLRSDDTAVYYCAR<u>SQLGRRFDY</u>W<br>GQGTLVTVSS |
| 33 | hz-HC11 | h-Y1238_VH_A40R-T74K-I76S-Y95F | QVQLVQSGAEVKKPGASVKVSCKAS<u>GY</u><br><u>AFTNYLIE</u>WVRQRPGQGLEWMG<u>VINPG</u><br><u>SGGTNYNEKFKG</u>RVTMTRDKSSTAYM<br>ELSRLRSDDTAVYFCAR<u>SQLGRRFDY</u>W<br>GQGTLVTVSS |

TABLE 13

Humanized Y1238 variable light sequences:

| SEQ ID NO: | Hz-LC# | ID | Sequence |
|---|---|---|---|
| 34 | hz-LC1 | h-Y1238_VK | DIQMTQSPSSLSASVGDRVTITC<u>KASQDVR</u><br><u>TGVAW</u>YQQKPGKAPKLLIY<u>SASYRNT</u>GVP<br>SRFSGSGSGTDFTFTISSLQPEDIATYYC<u>QQ</u><br><u>HYSPPYT</u>FGGGTKVEIK |
| 35 | hz-LC2 | h-Y1238_VK_G66R | DIQMTQSPSSLSASVGDRVTITC<u>KASQDVR</u><br><u>TGVAW</u>YQQKPGKAPKLLIY<u>SASYRNT</u>GVP<br>SRFSGSRSGTDFTFTISSLQPEDIATYYC<u>QQ</u><br><u>HYSPPYT</u>FGGGTKVEIK |
| 36 | hz-LC3 | h-Y1238_VK_K42Q-A43S-G66R-T85V | DIQMTQSPSSLSASVGDRVTITC<u>KASQDVR</u><br><u>TGVAW</u>YQQKPGQSPKLLIY<u>SASYRNT</u>GVP<br>SRFSGSRSGTDFTFTISSLQPEDIAVYYC<u>QQ</u><br><u>HYSPPYT</u>FGGGTKVEIK |

TABLE 13-continued

Humanized Y1238 variable light sequences:

| SEQ ID NO: | Hz-LC# | ID | Sequence |
|---|---|---|---|
| 37 | hz-LC4 | h-Y1238_VK_K42Q-A43S-G66R-P80A-T85V | DIQMTQSPSSLSASVGDRVTITC<u>KASQDVR</u><br>TGVAWYQQKPGQSPKLLIY<u>SASYRNT</u>GVP<br>SRFSGS<u>R</u>SGTDFTFTISSLQAEDIAVYYC<u>QQ</u><br><u>HYSPPYT</u>FGGGTKVEIK |
| 38 | hz-LC5 | h-Y1238_VK_G66R-K42Q_T85V | DIQMTQSPSSLSASVGDRVTITC<u>KASQDVR</u><br>TGVAWYQQKPGQAPKLLIY<u>SASYRNT</u>GVP<br>SRFSGS<u>R</u>SGTDFTFTISSLQPEDIAVYYC<u>QQ</u><br><u>HYSPPYT</u>FGGGTKVEIK |

The $V_H$ sequences were formatted in the context of an IgG1.3f isotype. The $V_K$ sequences were formatted as a full light chain with a common CL sequence. All 55 combinations of these humanized HC and LC constructs, as well as the chimeric Y1238 molecule were expressed as 3 ml supernatants for binding analysis by SPR. Each of the 56 supernatants, as well as a purified Y1238-chimeric IgG1 antibody, was captured on a protein A sensor chip and tested for binding to two concentrations (i.e., 200 nM and 1000 nM) of hCD40-monomer using BIAcore™ SPR in a screening assay. All antibodies, except for those containing hz-HC3, captured at high levels (>300 RU) using a 100-fold dilution of the expression supernatant, indicating a high antibody titer in the supernatant except for the hz-HC3 samples. The kinetic data for the two concentrations of hCD40-monomer were fit to a 1:1 Langmuir model, to yield estimates of the kinetic and affinity values for these interactions, and for comparison of the different molecules. These data showed that the captured antibodies bound with high affinity to CD40; the estimated KD values between 2.65 nM and 18.2 nM, see TABLE 14. For a given light chain, the antibodies with heavy chains hzHC1, hz-HC2, hz-HC4, hz-HC5, hz-HC6, hz-HC7, hz-HC8 and hz-HC9 demonstrated higher CD40 affinity than those containing hz-HC10 or hz-HC11. Also, for a given heavy chain, the antibodies with light chains hz-LC1 or hz-LC2 had higher CD40 affinity than those with hz-LC3, hz-LC4 or hz-LC5. A full kinetic titration series of CD40 binding to representative supernatants and purified chimeric Y1238 also demonstrated that the estimated $K_D$ values based on the 2 point (200 nM and 1000 nM) screening data, were reasonable estimates of the binding kinetics and affinity for the supernatant samples when compared to a full kinetic titration series of analyte as shown in TABLE 14.

TABLE 14

SPR kinetic and affinity data for human-CD40 monomer binding to humanized Y1238 antibodies captured on a protein A sensor chip surface. Data are shown for a 2 point screening assay where 200 nM and 1000 nM samples of human-CD40 monomer were tested, as well as for a "full kinetics" assay where a full concentration series of human-CD40 monomer was tested.

| HC | LC | Antibody/supernatant # | Ab ID# | Sample | Assay | Capture level | ka (1/Ms) | kd (1/s) | KD (M) |
|---|---|---|---|---|---|---|---|---|---|
| hz-HC1 | hz-LC1 | Sup 1 | hz1 | supernatant | 2 pt screen | 466 | 4.8E+04 | 2.0E−04 | 4.2E−09 |
| hz-HC1 | hz-LC2 | Sup 2 | hz2 | supernatant | 2 pt screen | 819 | 4.5E+04 | 2.3E−04 | 5.2E−09 |
| hz-HC1 | hz-LC3 | Sup 3 | hz3 | supernatant | 2 pt screen | 850 | 4.8E+04 | 4.8E−04 | 1.0E−08 |
| hz-HC1 | hz-LC4 | Sup 4 | hz4 | supernatant | 2 pt screen | 784 | 4.8E+04 | 4.2E−04 | 8.9E−09 |
| hz-HC1 | hz-LC5 | Sup 5 | hz5 | supernatant | 2 pt screen | 917 | 4.7E+04 | 5.0E−04 | 1.1E−08 |
| hz-HC2 | hz-LC1 | Sup 6 | hz6 | supernatant | 2 pt screen | 903 | 4.5E+04 | 1.2E−04 | 2.7E−09 |
| hz-HC2 | hz-LC2 | Sup 7 | hz7 | supernatant | 2 pt screen | 988 | 4.3E+04 | 1.1E−04 | 2.7E−09 |
| hz-HC2 | hz-LC3 | Sup 8 | hz8 | supernatant | 2 pt screen | 694 | 4.6E+04 | 2.9E−04 | 6.2E−09 |
| hz-HC2 | hz-LC4 | Sup 9 | hz9 | supernatant | 2 pt screen | 735 | 4.7E+04 | 3.1E−04 | 6.6E−09 |
| hz-HC2 | hz-LC5 | Sup 10 | hz10 | supernatant | 2 pt screen | 861 | 4.5E+04 | 2.7E−04 | 5.9E−09 |
| hz-HC3 | hz-LC1 | Sup 11 | hz11 | supernatant | 2 pt screen | 2 | | | |
| hz-HC3 | hz-LC2 | Sup 12 | hz12 | supernatant | 2 pt screen | 1 | | | |
| hz-HC3 | hz-LC3 | Sup 13 | hz13 | supernatant | 2 pt screen | 2 | | | |
| hz-HC3 | hz-LC4 | Sup 14 | hz14 | supernatant | 2 pt screen | 1 | | | |
| hz-HC3 | hz-LC5 | Sup 15 | hz15 | supernatant | 2 pt screen | 0 | | | |
| hz-HC4 | hz-LC1 | Sup 16 | hz16 | supernatant | 2 pt screen | 1034 | 4.5E+04 | 1.2E−04 | 2.7E−09 |
| hz-HC4 | hz-LC2 | Sup 17 | hz17 | supernatant | 2 pt screen | 1002 | 4.2E+04 | 1.8E−04 | 4.4E−09 |

TABLE 14-continued

SPR kinetic and affinity data for human-CD40 monomer binding to humanized Y1238 antibodies captured on a protein A sensor chip surface. Data are shown for a 2 point screening assay where 200 nM and 1000 nM samples of human-CD40 monomer were tested, as well as for a "full kinetics" assay where a full concentration series of human-CD40 monomer was tested.

| HC | LC | Antibody/ supernatant # | Ab ID# | Sample | Assay | Capture level | ka (1/Ms) | kd (1/s) | KD (M) |
|---|---|---|---|---|---|---|---|---|---|
| hz-HC4 | hz-LC3 | Sup 18 | hz18 | supernatant | 2 pt screen | 1016 | 4.6E+04 | 3.5E−04 | 7.6E−09 |
| hz-HC4 | hz-LC4 | Sup 19 | hz19 | supernatant | 2 pt screen | 942 | 4.5E+04 | 2.8E−04 | 6.3E−09 |
| hz-HC4 | hz-LC5 | Sup 20 | hz20 | supernatant | 2 pt screen | 1123 | 4.5E+04 | 3.7E−04 | 8.3E−09 |
| hz-HC5 | hz-LC1 | Sup 21 | hz21 | supernatant | 2 pt screen | 956 | 4.2E+04 | 1.5E−04 | 3.5E−09 |
| hz-HC5 | hz-LC2 | Sup 22 | hz22 | supernatant | 2 pt screen | 1111 | 4.0E+04 | 1.2E−04 | 2.9E−09 |
| hz-HC5 | hz-LC3 | Sup 23 | hz23 | supernatant | 2 pt screen | 788 | 4.3E+04 | 3.1E−04 | 7.2E−09 |
| hz-HC5 | hz-LC4 | Sup 24 | hz24 | supernatant | 2 pt screen | 1007 | 4.3E+04 | 3.2E−04 | 7.4E−09 |
| hz-HC5 | hz-LC5 | Sup 25 | hz25 | supernatant | 2 pt screen | 838 | 4.3E+04 | 2.8E−04 | 6.6E−09 |
| hz-HC6 | hz-LC1 | Sup 26 | hz26 | supernatant | 2 pt screen | 975 | 4.1E+04 | 1.2E−04 | 2.9E−09 |
| hz-HC6 | hz-LC2 | Sup 27 | hz27 | supernatant | 2 pt screen | 1027 | 4.0E+04 | 1.3E−04 | 3.3E−09 |
| hz-HC6 | hz-LC3 | Sup 28 | hz28 | supernatant | 2 pt screen | 1051 | 4.2E+04 | 2.4E−04 | 5.6E−09 |
| hz-HC6 | hz-LC4 | Sup 29 | hz29 | supernatant | 2 pt screen | 820 | 4.2E+04 | 2.8E−04 | 6.5E−09 |
| hz-HC6 | hz-LC5 | Sup 30 | hz30 | supernatant | 2 pt screen | 1058 | 4.2E+04 | 3.3E−04 | 7.7E−09 |
| hz-HC7 | hz-LC1 | Sup 31 | hz31 | supernatant | 2 pt screen | 1004 | 3.9E+04 | 1.2E−04 | 3.0E−09 |
| hz-HC7 | hz-LC2 | Sup 32 | hz32 | supernatant | 2 pt screen | 1033 | 3.7E+04 | 1.7E−04 | 4.5E−09 |
| hz-HC7 | hz-LC3 | Sup 33 | hz33 | supernatant | 2 pt screen | 878 | 4.0E+04 | 3.5E−04 | 8.7E−09 |
| hz-HC7 | hz-LC4 | Sup 34 | hz34 | supernatant | 2 pt screen | 792 | 4.0E+04 | 2.8E−04 | 7.1E−09 |
| hz-HC7 | hz-LC5 | Sup 35 | hz35 | supernatant | 2 pt screen | 974 | 4.0E+04 | 3.7E−04 | 9.2E−09 |
| hz-HC8 | hz-LC1 | Sup 36 | hz36 | supernatant | 2 pt screen | 973 | 3.9E+04 | 1.4E−04 | 3.7E−09 |
| hz-HC8 | hz-LC2 | Sup 37 | hz37 | supernatant | 2 pt screen | 926 | 3.7E+04 | 1.1E−04 | 2.8E−09 |
| hz-HC8 | hz-LC3 | Sup 38 | hz38 | supernatant | 2 pt screen | 1012 | 3.9E+04 | 3.2E−04 | 8.2E−09 |
| hz-HC8 | hz-LC4 | Sup 39 | hz39 | supernatant | 2 pt screen | 784 | 4.0E+04 | 3.0E−04 | 7.5E−09 |
| hz-HC8 | hz-LC5 | Sup 40 | hz40 | supernatant | 2 pt screen | 1001 | 3.9E+04 | 2.6E−04 | 6.5E−09 |
| hz-HC9 | hz-LC1 | Sup 41 | hz41 | supernatant | 2 pt screen | 977 | 3.8E+04 | 1.7E−04 | 4.4E−09 |
| hz-HC9 | hz-LC2 | Sup 42 | hz42 | supernatant | 2 pt screen | 972 | 3.6E+04 | 2.0E−04 | 5.4E−09 |
| hz-HC9 | hz-LC3 | Sup 43 | hz43 | supernatant | 2 pt screen | 994 | 3.9E+04 | 2.9E−04 | 7.6E−09 |
| hz-HC9 | hz-LC4 | Sup 44 | hz44 | supernatant | 2 pt screen | 866 | 3.9E+04 | 3.3E−04 | 8.5E−09 |
| hz-HC9 | hz-LC5 | Sup 45 | hz45 | supernatant | 2 pt screen | 1029 | 3.9E+04 | 3.8E−04 | 9.6E−09 |
| hz-HC10 | hz-LC1 | Sup 46 | hz46 | supernatant | 2 pt screen | 1182 | 3.9E+04 | 2.0E−04 | 5.1E−09 |
| hz-HC10 | hz-LC2 | Sup 47 | hz47 | supernatant | 2 pt screen | 1134 | 3.6E+04 | 3.2E−04 | 8.8E−09 |
| hz-HC10 | hz-LC3 | Sup 48 | hz48 | supernatant | 2 pt screen | 988 | 3.9E+04 | 5.5E−04 | 1.4E−08 |
| hz-HC10 | hz-LC4 | Sup 49 | hz49 | supernatant | 2 pt screen | 977 | 3.9E+04 | 4.8E−04 | 1.2E−08 |
| hz-HC10 | hz-LC5 | Sup 50 | hz50 | supernatant | 2 pt screen | 975 | 3.9E+04 | 6.1E−04 | 1.6E−08 |
| hz-HC11 | hz-LC1 | Sup 51 | hz51 | supernatant | 2 pt screen | 1349 | 3.7E+04 | 2.5E−04 | 6.7E−09 |
| hz-HC11 | hz-LC2 | Sup 52 | hz52 | supernatant | 2 pt screen | 1321 | 3.5E+04 | 2.3E−04 | 6.5E−09 |
| hz-HC11 | hz-LC3 | Sup 53 | hz53 | supernatant | 2 pt screen | 1288 | 3.7E+04 | 6.7E−04 | 1.8E−08 |

TABLE 14-continued

SPR kinetic and affinity data for human-CD40 monomer binding to humanized Y1238 antibodies captured on a protein A sensor chip surface. Data are shown for a 2 point screening assay where 200 nM and 1000 nM samples of human-CD40 monomer were tested, as well as for a "full kinetics" assay where a full concentration series of human-CD40 monomer was tested.

| HC | LC | Antibody/ supernatant # | Ab ID# | Sample | Assay | Capture level | ka (1/Ms) | kd (1/s) | KD (M) |
|---|---|---|---|---|---|---|---|---|---|
| hz-HC11 | hz-LC4 | Sup 54 | hz54 | supernatant | 2 pt screen | 931 | 3.8E+04 | 5.6E−04 | 1.5E−08 |
| hz-HC11 | hz-LC5 | Sup 55 | hz55 | supernatant | 2 pt screen | 1107 | 3.7E+04 | 5.6E−04 | 1.5E−08 |
| HC-Chim | LC-Chim | Sup 56 | chimeric | supernatant | 2 pt screen | 326 | 5.7E+04 | 3.2E−04 | 5.6E−09 |
| HC-Chim | LC-Chim | Y1238-IgG1 | chimeric | purified | 2 pt screen | 468 | 5.6E+04 | 3.8E−04 | 6.7E−09 |
| HC-Chim | LC-Chim | Y1238-IgG1 | chimeric | purified | 2 pt screen | 461 | 5.9E+04 | 4.0E−04 | 6.9E−09 |
| HC-Chim | LC-Chim | Y1238-IgG1 | chimeric | purified | 2 pt screen | 444 | 5.8E+04 | 5.0E−04 | 8.6E−09 |
| hz-HC1 | hz-LC1 | Sup 1 | hz1 | supernatant | full kinetics | | 6.5E+04 | 1.9E−04 | 3.0E−09 |
| HC-Chim | LC-Chim | Sup 56 | chimeric | supernatant | full kinetics | | 8.6E+04 | 2.2E−04 | 2.6E−09 |
| HC-Chim | LC-Chim | Y1238-IgG1 | chimeric | purified | full kinetics | | 8.3E+04 | 2.7E−04 | 3.2E−09 |

Based on the supernatant screening SPR data and bias towards constructs with fewer framework back-mutations, a subset of humanized Y1238 antibodies were selected for expression, purification, and further characterization. Two of these antibodies (i.e., Y1238-hz1 and Y1238-hz2) were formatted with P238K and N297A isotypes (i.e., SEQ ID NOS: 39, 40, 42, and 43 for heavy chains; see TABLE 15 for light chains) and tested for CD40 and FcgR binding by SPR.

The CD40 binding SPR data showed that each antibody bound the CD40 target with high affinity, TABLE 16. The data is compared to that of another anti-CD40 antibody, antibody BI-mAb-B (i.e., SEQ ID NOS: 95 and 96, disclosed in U.S. Pat. No. 9,090,696 and referred to therein as "Antibody B"), which binds with much lower affinity than the humanized Y1238 molecules, TABLE 15. The Fc domain is underlined.

TABLE 15

| Protein ID | HC | LC |
|---|---|---|
| Y1238-hz1-P238K | QVQLVQSGAEVKKPGASVKV SCKASGYAFTNYLIEWVRQAP GQGLEWMGVINPGSGGTNYN EKFKGRVTMTRDTSISTAYME LSRLRSDDTAVYYCARSQLGR RFDYWGQGTLVTVSSASTKG PSVFPLAPSSKSTSGGTAALGC LVKDYFPEPVTVSWNSGALTS GVHTFPAVLQSSGLYSLSSVV TVPSSSLGTQTYICNVNHKPSN TKVDKRV<u>EPKSCDKTHTCPPC PAPELLGGKSVFLFPPKPKDTL MISRTPEVTCVVVDVSHEDPE VKFNWYVDGVEVHNAKTKP REEQYNSTYRVVSVLTVLHQ DWLNGKEYKCKVSNKALPAP IEKTISKAKGQPREPQVYTLPP SRDELTKNQVSLTCLVKGFYP SDIAVEWESNGQPENNYKTTP PVLDSDGSFFLYSKLTVDKSR WQQGNVFSCSVMHEALHNH YTQKSLSLSPG</u> SEQ ID NO: 39 | DIQMTQSPSSLSASVGDRVTITCK ASQDVRTGVAWYQQKPGKAPK LLIYSASYRNTGVPSRFSGS<u>G</u>SGT DFTFTISSLQPEDIATYYCQQHYS PPYTFGGGTKVEIKRTVAAPSVFI FPPSDEQLKSGTASVVCLLNNFY PREAKVQWKVDNALQSGNSQES VTEQDSKDSTYSLSSTLTLSKAD YEKHKVYACEVTHQGLSSPVTK SFNRGEC SEQ ID NO: 41 |
| Y1238 hz1-N297A | QVQLVQSGAEVKKPGASVKV SCKASGYAFTNYLIEWVRQAP GQGLEWMGVINPGSGGTNYN EKFKGRVTMTRDTSISTAYME LSRLRSDDTAVYYCARSQLGR RFDYWGQGTLVTVSSASTKG PSVFPLAPSSKSTSGGTAALGC LVKDYFPEPVTVSWNSGALTS GVHTFPAVLQSSGLYSLSSVV TVPSSSLGTQTYICNVNHKPSN TKVDKRV<u>EPKSCDKTHTCPPC PAPELLGGPSVFLFPPKPKDTL</u> | DIQMTQSPSSLSASVGDRVTITCK ASQDVRTGVAWYQQKPGKAPK LLIYSASYRNTGVPSRFSGS<u>G</u>SGT DFTFTISSLQPEDIATYYCQQHYS PPYTFGGGTKVEIKRTVAAPSVFI FPPSDEQLKSGTASVVCLLNNFY PREAKVQWKVDNALQSGNSQES VTEQDSKDSTYSLSSTLTLSKAD YEKHKVYACEVTHQGLSSPVTK SFNRGEC SEQ ID NO: 41 |

TABLE 15-continued

| Protein ID | HC | LC |
|---|---|---|
| | MISRTPEVTCVVVDVSHEDPE VKFNWYVDGVEVHNAKTKP REEQYASTYRVVSVLTVLHQ DWLNGKEYKCKVSNKALPAP IEKTISKAKGQPREPQVYTLPP SREEMTKNQVSLTCLVKGFYP SDIAVEWESNGQPENNYKTTP PVLDSDGSFFLYSKLTVDKSR WQQGNVFSCSVMHEALHNH YTQKSLSLSPG SEQ ID NO: 40 | |
| Y1238-hz2-P238K | QVQLVQSGAEVKKPGASVKV SCKASGYAFTNYLIEWVRQAP GQGLEWMGVINPSGGTNYN EKFKGRVTMTRDTSISTAYME LSRLRSDDTAVYYCARSQLGR RFDYWGQGTLVTVSSASTKG PSVFPLAPSSKSTSGGTAALGC LVKDYFPEPVTVSWNSGALTS GVHTFPAVLQSSGLYSLSSVV TVPSSSLGTQTYICNVNHKPSN TKVDKRVEPKSCDKTHTCPPC PAPELLGGKSVFLFPPKPKDTL MISRTPEVTCVVVDVSHEDPE VKFNWYVDGVEVHNAKTKP REEQYNSTYRVVSVLTVLHQ DWLNGKEYKCKVSNKALPAP IEKTISKAKGQPREPQVYTLPP SRDELTKNQVSLTCLVKGFYP SDIAVEWESNGQPENNYKTTP PVLDSDGSFFLYSKLTVDKSR WQQGNVFSCSVMHEALHNH YTQKSLSLSPG SEQ ID NO: 42 | DIQMTQSPSSLSASVGDRVTTTCK ASQDVRTGVAWYQQKPGKAPK LLIYSASYRNTGVPSRFSGSRSGT DFTFTISSLQPEDIATYYCQQHYS PPYTFGGGTKVEIKRTVAAPSVFI FPPSDEQLKSGTASVVCLLNNFY PREAKVQWKVDNALQSGNSQES VTEQDSKDSTYSLSSTLTLSKAD YEKHKVYACEVTHQGLSSPVTK SFNRGEC SEQ ID NO: 44 |
| Y1238-hz2-N297A | QVQLVQSGAEVKKPGASVKV SCKASGYAFTNYLIEWVRQAP GQGLEWMGVINPSGGTNYN EKFKGRVTMTRDTSISTAYME LSRLRSDDTAVYYCARSQLGR RFDYVVGQGTLVTVSSASTKG PSVFPLAPSSKSTSGGTAALGC LVKDYFPEPVTVSWNSGALTS GVHTFPAVLQSSGLYSLSSVV TVPSSSLGTQTYICNVNHKPSN TKVDKRVEPKSCDKTHTCPPC PAPELLGGPSVFLFPPKPKDTL MISRTPEVTCVVVDVSHEDPE VKFNWYVDGVEVHNAKTKP REEQYASTYRVVSVLTVLHQ DWLNGKEYKCKVSNKALPAP IEKTISKAKGQPREPQVYTLPP SREEMTKNQVSLTCLVKGFYP SDIAVEWESNGQPENNYKTTP PVLDSDGSFFLYSKLTVDKSR WQQGNVFSCSVMHEALHNH YTQKSLSLSPG SEQ ID NO: 43 | DIQMTQSPSSLSASVGDRVTTTCK ASQDVRTGVAWYQQKPGKAPK LLIYSASYRNTGVPSRFSGSRSGT DFTFTISSLQPEDIATYYCQQHYS PPYTFGGGTKVEIKRTVAAPSVFI FPPSDEQLKSGTASVVCLLNNFY PREAKVQWKVDNALQSGNSQES VTEQDSKDSTYSLSSTLTLSKAD YEKHKVYACEVTHQGLSSPVTK SFNRGEC SEQ ID NO: 44 |
| BI-mAb-B | EVQLVESGGGLVKPGGSLRLS CAASGFTFSDYGMHWVRQAP GKGLEWVAYISSGNRIIYYAD TVKGRFTISRDNAKNSLYLQM NSLRAEDTAVYYCARQDGYR YAMDYWGQGTLVTVSSASTK GPSVFPLAPSSKSTSGGTAALG CLVKDYFPEPVTVSWNSGALT SGVHTFPAVLQSSGLYSLSSV VTVPSSSLGTQTYICNVNHKPS NTKVDKRVEPKSCDKTHTCPP CPAPEAAGGPSVFLFPPKPKD TLMISRTPEVTCVVVDVSHED PEVKFNWYVDGVEVHNAKTK PREEQYNSTYRVVSVLTVLHQ DWLNGKEYKCKVSNKALPAP IEKTISKAKGQPREPQVYTLPP SREEMTKNQVSLTCLVKGFYP | DIVMTQSPDSLAVSLGEKVTINC KSSQSLLNSGNQKNYLTWHQQK PGQPPKLLIYWTSTRESGVPDRFS GSGSGTDFTLTISSLQAEDVAVY YCQNDYTYPLTFGGGTKVEIKRT VAAPSVFIFPPSDEQLKSGTASVV CLLNNFYPREAKVQWKVDNALQ SGNSQESVTEQDSKDSTYSLSSTL TLSKADYEKHKVYACEVTHQGL SSPVTKSFNRGEC SEQ ID NO: 96 |

TABLE 15-continued

| Protein ID | HC | LC |
|---|---|---|
| | | SDIAVEWESNGQPENNYKTTP PVLDSDGSFFLYSKLTVDKSR WQQGNVFSCSVMHEALHNH YTQKSLSLSPGK SEQ ID NO: 95 |

The alignment of the two light chain sequences for Hz1 and Hz2 from TABLE 15 (SEQ ID NOS: 41 and 44) is as follows and displays a one mutation difference (at position 66; underlined below) between the two sequences:

```
41  (1)    DIQMTQSPSSLSASVGDRVTITCKASQDVRTGVAWYQQKPGKAPKLLIYS 44  (1)    DIQMTQSPSSLSASVGDRVTITCKASQDVRTGVAWYQQKPGRAPKLLIYS
                51                                              100

41  (51)   ASYRNTGVPSRFSGSGSGTDFTFTISSLQPEDIATYYCQQHYSPPYTFGG 44  (51)   ASYRNTGVPSRFSGSRSGTDFTFTISSLQPEDIATYYCQQHYSPPYTFGG
               101                                              150

41  (101)  GTKVEIKRTVAAPSVFIFPPSDEQLKSGTASVVCLLNNFYPREAKVQWKV 44  (101)  GTKVEIKRTVAAPSVFIFPPSDEQLKSGTASVVCLLNNFYPREAKVQWKV
               151                                              200

41  (151)  DNALQSGNSGESVTEQDSKDSTYSLSSTLTLSKADYEKHKVYACEVTHQG 44  (151)  DNALQSGNSQESVTEQDSKDSTYSLSSTLTLSKADYEKHKVYACEVTHQG
               201                                214

41  (201)  LSSPVTKSFNRGEC 44  (201)  LSSPVTKSFNRGEC
```

TABLE 16

SPR kinetic and affinity data for human-CD40 monomer binding to humanized Y1238 antibodies or BI-mAb-B captured on a protein A sensor chip surface.

| Sample | ka (1/Ms) | kd (1/s) | KD (nM) |
|---|---|---|---|
| Y1238-hz1-P238K (n = 3) | 7.8 ± 0.8E+04 | 3.9 ± 0.7E−04 | 5.0 ± 0.7 |
| Y1238-hz1-N297A (n = 2) | 8.0 ± 1.4E+04 | 3.9 ± 0.7E−04 | 5.0 ± 1.8 |
| YI238-hz2-P238K (n = 2) | 7.0 ± 0.9E+04 | 4.3 ± 0.7E−04 | 6.2 ± 0.2 |
| Y1238-hz2-N297A | 6.6E+04 | 4.0E−04 | 6.0 |
| BI-mAb-B (n = 2) | 6.1 ± 0.3E+04 | 2.1 ± 1.6E−03 | 35 ± 1 |

All the Y1238 antibodies are demonstrated potent antagonists of B cell proliferation driven by either soluble CD40L trimer or cellular CD40L from CD40L-expressing CHO cells (see TABLE 17). In contrast, the competitor antibody BI-mAb-B and 5F11-45-P238K showed potent inhibition of B cell proliferation driven by soluble CD40L signals, but was less effective at inhibiting B cell proliferation driven by cellular CD40L (CHO cells overexpressing CD40L). The Y1238 chimeric and humanized antibodies exhibited only about a 10-fold shift in potency when cellular CD40L was used to stimulated B cells.

TABLE 17

Inhibition of tonsillar human B cells driven either by soluble CD40L timer or cell associated CD40L from CD40L overexpressing CHO cells.

| | CD40L Trimer IC50 (ng/ml) | | CHO CD40L IC50 (ng/ml) | |
|---|---|---|---|---|
| | Average | STDEV (n) | Average | STDEV (n) |
| Y1238 | 3.4 | 1.5 (15) | 19.9 | 6.8 (4) |
| Y1238-P238K | 3.4 | 0.7 (15) | 18.4 | 5.5 (2) |
| Y1238-N297A | 3.6 | 1.0 (6) | 17.0 | 8.6 (2) |
| Y1238-hz1-P238K | 3.1 | 1.0 (7) | 32 | 6 (7) |
| Y1238-hz1-N297A | 3.1 | 0.8 (8) | 35 | 8 (8) |
| Y1238-hz2-P238K | 2.7 | 0.7 (8) | 21 | 5 (7) |
| Y1238-hz2-N297A | 2.9 | 0.4 (5) | 20 | 6 (5) |
| 5F11-45-P238K | 10.0 | 4.6 (14) | 66% @ 1 μg/ml* | (9) |
| BI-mAb-B | 7.4 | 3.5 (19) | 58% @ 1 μg/ml* | (6) |

IC50 for inhibition of proliferation of B cells is given in ng/ml. Standard deviation (STDEV) and the number of donors (n) is indicated.
*BI mAb-B and 5F11-45-P238K did not completely inhibit B cell proliferation the average inhibition at 1 μg/ml is given.

FcgR binding for the humanized Y1238 antibodies (i.e., Y1238-hz1-N297A, Y1238-hz1-P238K, Y1238-hz2-P238K and Y1238-hz1-N297A) were consistent with previous data for the chimeric Y1238 antibodies and 5F11-45 antibodies, showing very weak binding responses for all of the low affinity FcgRs, TABLE 18.

TABLE 18

% Rmax data for 1 μM or 10 μM humanized Y1238 antibodies binding to anti-His Fab captured hFcgR-His proteins.

| Sample | Conc (μM) | hCD64 | hCD32a-H131 | hCD32a-R131 | hCD32b | hCD16a-V158 | hCD16b-NA2 |
|---|---|---|---|---|---|---|---|
| Y1238-hz1-P238K | 1 | 60% | 0% | 0% | 0% | 0% | 0% |
| Y1238-hz1-N297A | 1 | 59% | 0% | 0% | 0% | 1% | 0% |
| Y1238-hz2-P238K | 1 | 63% | 0% | 0% | 0% | 0% | 0% |
| Y1238-hz2-N297A | 1 | 62% | 0% | 1% | 0% | 1% | 0% |
| Y1238-hz1-P238K | 10 | 65% | 1% | 1% | 1% | 0% | 0% |
| Y1238-hz1-N297A | 10 | 64% | 1% | 3% | 1% | 3% | 0% |
| Y1238-hz2-P238K | 10 | 66% | 2% | 3% | 2% | 1% | 0% |
| Y1238-hz2-N297A | 10 | 65% | 3% | 7% | 2% | 7% | 1% |

Figure 6:
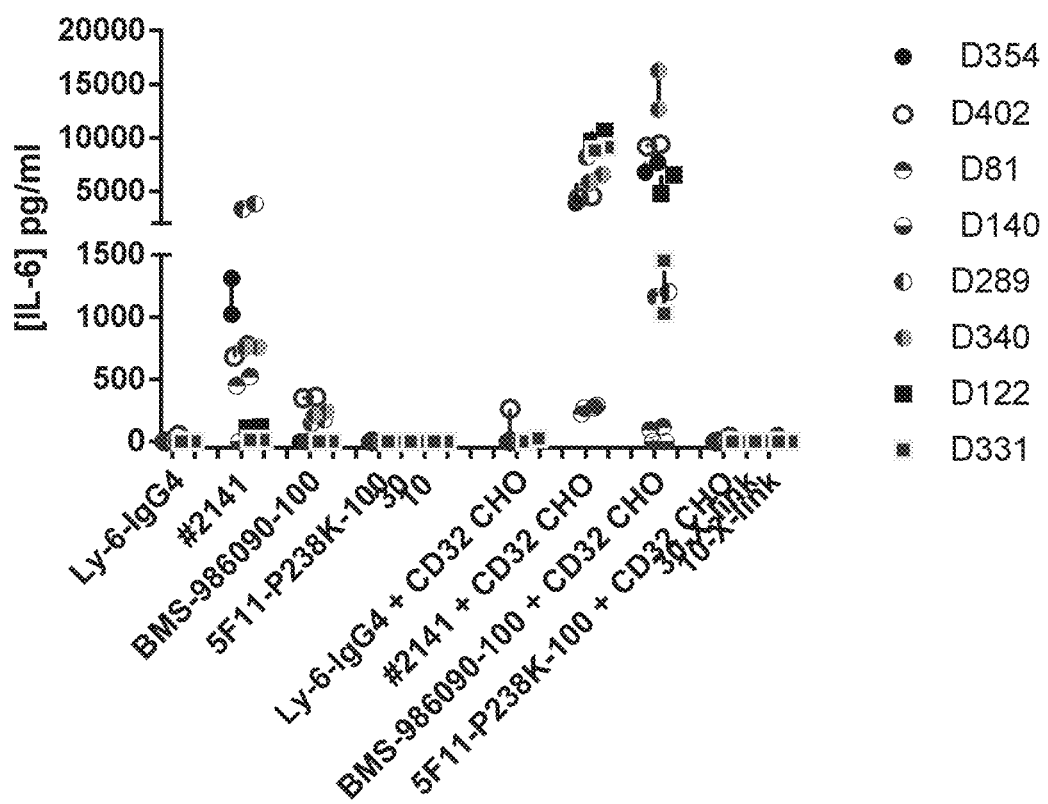
FIG. 6, comprising
Figure 6:
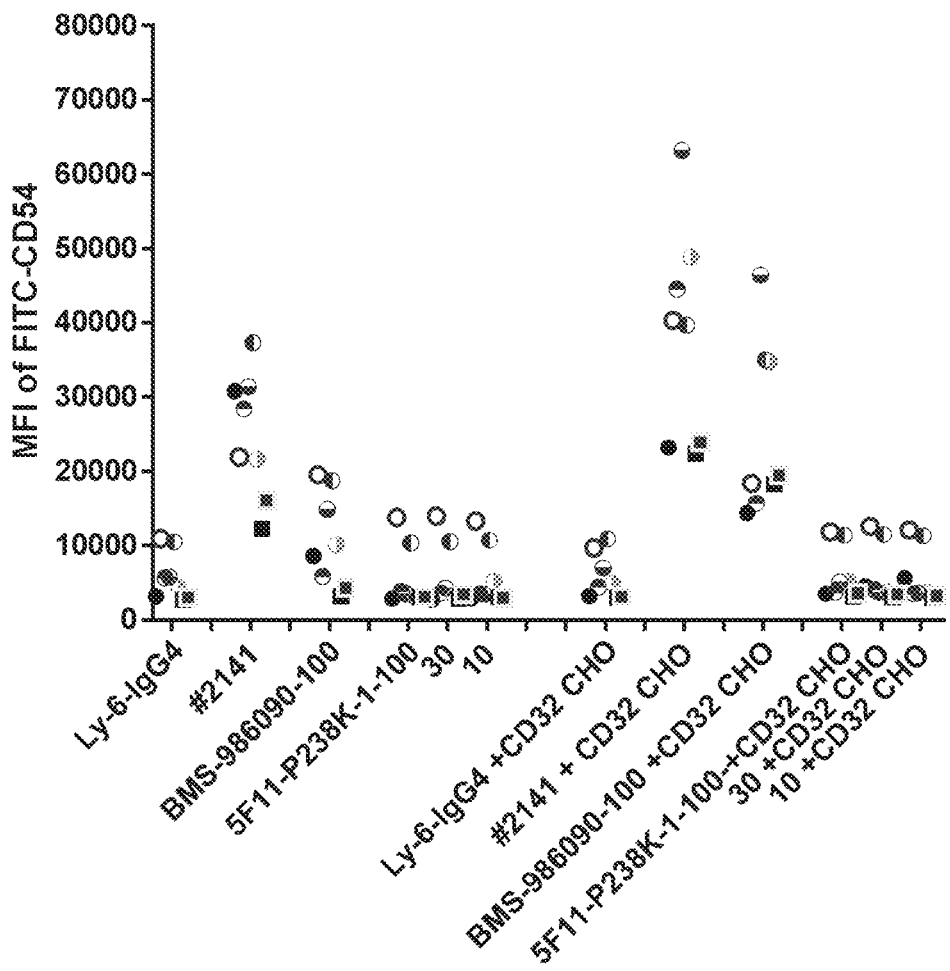
Figure 6:
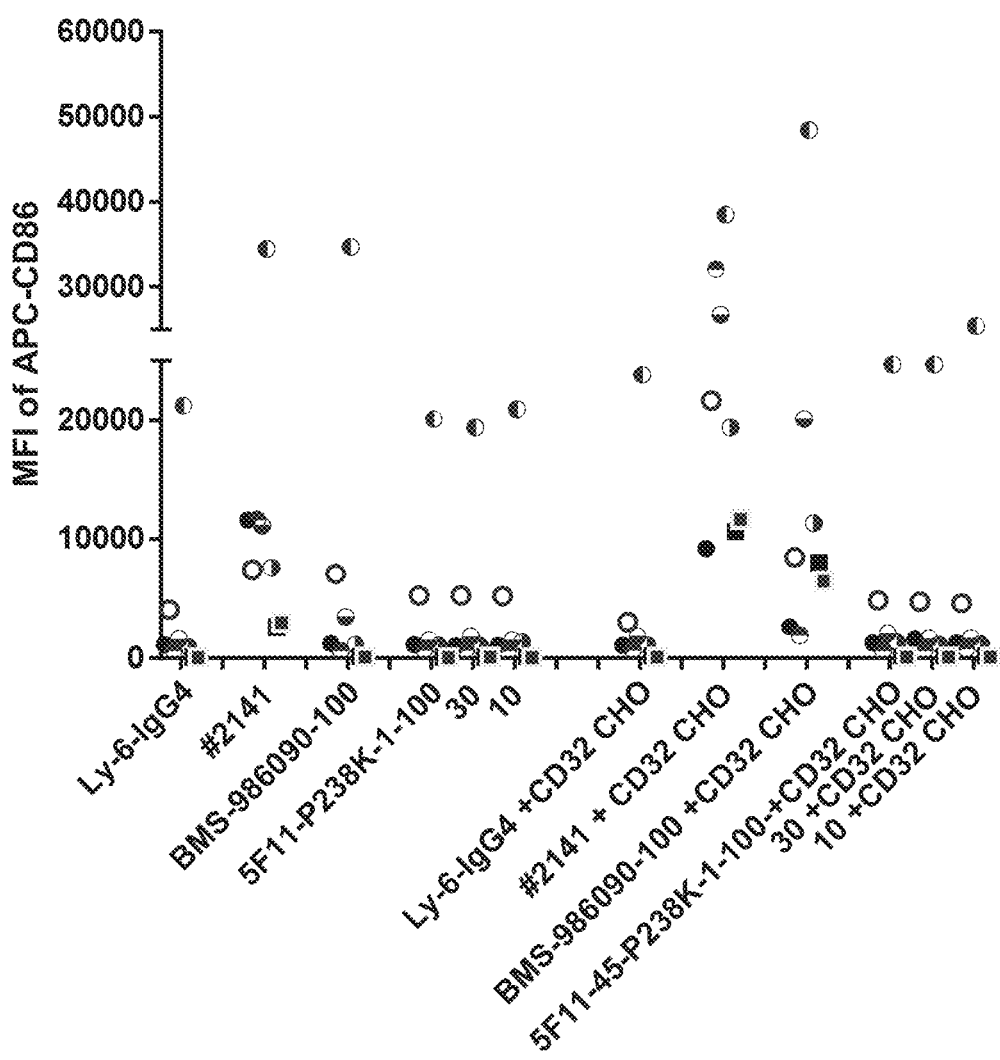

In addition, humanized versions of Y1238 antibodies exhibited minimal activation of iDC over the negative control protein L6-IgG4 when tested either alone or with the addition of FcgR CD32 expressing CHO cells. This observation is consistent with the inability of the humanized Y1238 antibodies to activate CD40 even with the exaggerated cross-linking provided by the CD32 overexpressing CHO cells. In contrast, both the 2141 and BMS-986090 controls showed donor-dependent moderate activation of iDC alone which was robustly increased when cross-linked or clustered by the CD32 CHO cells, FIG. 5 and FIG. 6. Similarly, 5F11-45-P238K, when tested across a larger panel of iDC donors, did not exhibit activation alone or with CD32 mediated clustering or cross-linking, FIG. 6.

Materials and Methods for the Examples

FCGR BINDING SPR: FcgR binding can be measured in vitro using purified FcgRs using methods such as BIAcore™ surface plasmon resonance (SPR). One method tests the binding of purified antibodies to His-tagged FcgR proteins (FcgR-His) which are captured on the immobilized Fab fragment of an anti-His antibody. These experiments are performed on either a BIAcore™ T100 or BIAcore™ T200 instrument (GE Healthcare Life Sciences, Marlborough, Mass.) at 25° C. The Fab fragment from a murine anti-6×His antibody (generated in house) is immobilized on a CM5 sensor chip using standard ethyl(dimethylaminopropyl) carbodiimide (EDC)/N-hydroxysuccinimide (NHS) chemistry with ethanolamine blocking, to a density of ~3000 RU in a running buffer of 10 mM HEPES pH 7.4, 150 mM NaCl, 3 mM EDTA, 0.05% surfactant p20 (HBS-EP+). All remaining studies are performed using a running buffer of 10 mM NaPO4, 130 mM NaCl, 0.05% p20 (PBS-T) pH 7.1. Various FcγR proteins containing a C-terminal 6× poly-histidine tag (generated in house) are captured on this surface (typically using FcgR-his protein concentration of ~7 μg/ml) using a contact time of 30 sec at 10 μl/min. Various concentrations of purified antibody are tested for binding, for example using an association time of 120 seconds at 30 μl/min, and a dissociation time of 120 seconds at 30 μl/min. FcgR proteins tested in these studies include the "high affinity" FcgR CD64 (hFcgRI), as well as the "low affinity" FcgRs CD32a-H131 (FcgRIIa-H131), CD32a-R131 (FcgRIIa-R131), CD32b (FcgRIIb), CD16a-V158 (FcgRIIIa-V158), and CD16b-NA2 (FcgRIIIb-NA2).

To quantitatively analyze the binding responses and compare the FcgR binding of different molecules, the SPR binding data can be analyzed by calculating the maximum binding response as a percentage of the theoretical maximum binding response (% Rmax), using the equation:

% $R$max=(Binding Response Analyte)/[((Mw Analyte)/(Mw Ligand))×(Response Ligand)×(analyte:ligand stoichiometry)]  EQUATION 1:

where "Analyte" is the antibody and Ligand is the captured FcgR protein.

This analysis does not take into account the mass of glycosylation of antibody or FcgR, and assumes 100% fractional activity for the captured ligand. Since the FcgRs are glycosylated, the % Rmax values are typically less than 100% even under saturating conditions. The % Rmax analysis is particularly useful for evaluating the binding of the "low affinity" FcgRs CD32a-H131, CD32a-R131, CD32b, CD16a-V158 and CD16b-NA2, which have relatively fast association and dissociation rates and affinities near or below the analyte concentrations tested (1 uM), so saturation of the surface is generally not achieved under these conditions. In contrast, the "high affinity" FcgR CD64 binds with higher affinity and slower dissociation kinetics than the other FcgRs particularly to IgG1 and IgG4. Thus, these isotypes do typically saturate the CD64 surface under micromolar analyte concentrations, and are more difficult to differentiate binding affinities using % Rmax. For these interactions, differences between antibodies can be easily observed by comparison of the dissociation rates in the sensorgram data.

CD40 BINDING KINETICS AND AFFINITY: The monovalent CD40 binding affinity of the antibody molecules is measured by SPR on a BIAcore™ T100 or T200 instrument (GE Healthcare) at 25° C. by capturing antibody on an immobilized protein A sensor chip surface, and then binding human-CD40-monomer protein (generated in house) using an association time of 180 seconds, dissociation time of 360 seconds at 30 μl/min in PBS-T (phosphate buffered saline with Tween®20) at pH 7.1.

PRIMARY CELL ISOLATION AND CULTURE: PBMCs (peripheral blood mononuclear cells) are isolated from heparinized human blood by Ficoll density gradient separation. Monocytes are isolated from PBMC following the Manual EasySep protocol (STEMCELL, Vancouver, Canada). One million of isolated monocytes are plated in in each well of a 6-well plate in 6 m is of complete media (RPMI-1640, 10% heat-inactivated fetal bovine serum, 100 units/ml penicillin-streptomycin), containing human IL-4 (Interleukin-4, 100 ng/ml) and human GM-CSF (Granulocyte macrophage colony-stimulating factor, 100 ng/ml) and incubated for 6 days at 37° C./5% CO$_2$, changing media every other day and replacing it with fresh media containing the same concentration of cytokines. iDCs were harvested on day 6, washed thoroughly, and re-suspended in complete media.

TREATMENT OF iDCS WITH ANTI-CD40 ANTIBODIES IN THE PRESENCE OR ABSENCE OF FcγR CLUSTERING/CROSSLINKING: Titrations of the various biological agents are made in complete media, and added to duplicate 96-well plates. In the case of cross-linking, antibodies are added to the cells for 30 min. prior to the addition of CD32a-expressing CHO cells at a ratio of 1:6. Cells were incubated at 37° C. at 5% $CO_2$ for approximately 18-20 hours. 150 μL of supernatant is removed from each well, diluted 1:5, and is evaluated for protein concentrations of IL-6, TNFα and IL-12 using a commercially available ELISA kits (R&D Systems, Minneapolis, Minn.), according to manufacturer's instructions. The cells remaining in the plates from the harvested supernatants, are combined into 1 sample per duplicate treatment, and transferred to a new 96-well round bottom (RB) plate, and placed at 4° C. Cells are washed with D-PBS (Dulbecco's Phosphate Buffered Saline), $Ca^{++}$ and $Mg^{++}$ free, and stained for 30 min. on ice for cell viability using the LIVE/DEAD® Fixable Near-IR Dead Cell Stain Kit (Invitrogen, Carlsbad, Calif.). Cells are washed and re-suspended in D-PBS, and Mg' free, 2% fetal bovine serum (FBS), 0.1% $NaN_3$ (staining buffer) and blocked with 5 μl/well of Human TruStain FcX™ (Fc Receptor Blocking Solution, Biolegend, San Diego, Calif.) in staining buffer.

DCs are immuno-stained with: PerCpCy5.5-conjugated αCD3, αCD19, αCD14 (Lin⁻), BUV395-conjugated αCD11c (BD Biosciences, San Diego, Calif.), APC-conjugated αCD86 (Biolegend, San Diego, Calif.), PE-conjugated αCD83 (eBioscience, San Diego, Calif.), FITC-conjugated αCD54 (Biolegend, San Diego, Calif.), and incubated at 4° C. for 45 minutes. Cells are washed twice in staining buffer and fixed (15 at RT, protected from light), by adding 100 μl of BD Cytofix Fixation Buffer (BD Bioscience, San Diego, Calif.). DCs are evaluated for CD86, ICAM-1 and CD83 expression using a LSRII-Fortessa Flow Cytometer (BD Biosciences, San Diego, Calif.), and FlowJo analysis software (Treestar, Ashland, Oreg.).

Inhibition of CD40L induces human B cell proliferation: Human tonsillar B cells are obtained from pediatric patients during routine tonsillectomy. The cells are isolated by mincing and gently mashing the tissue, passing the cells through a screen and isolating mononuclear cells with density gradient separation using human Lympholyte®-H separation media (Cedarlane Labs, Burlington, ON). Mononuclear cells are collected from the interface, washed, and rosetted with sheep red blood cells (SRBC, Colorado Serum Company; Denver, Colo.) for one hour at 4° C., followed by density gradient separation to remove T cells. Cells are again washed and re-suspended in RPMI containing 10% FBS (complete media). Titrations of antibodies are made in complete media, and added in triplicate to 96-well round bottom (RB) plates. $1 \times 10^5$ tonsillar human B cells are added and stimulated with either soluble IZ-hCD40L (2 μg/mL), or with Chinese hamster ovary cells stably transfected with human CD40L (CHO-hCD40L) irradiated with 10,000 Rads; cells are then plated at $2 \times 10^3$ cells/well, in a final volume of 200 μL in each well. Plates are incubated at 37° C. at 5% $CO_2$ for 72 hours, labeled for the last 6 hours with 0.5 μCi of $^3$[H]-thymidine per well, harvested, and counted by liquid scintillation. B cell proliferation was quantitated based on thymidine incorporation.

---

We claim:

1. An isolated antibody, or antigen binding portion thereof, that specifically binds to human CD40, wherein the antibody comprises a heavy chain, and a light chain, wherein:
   the heavy chain comprises a CDR1 comprising GYTFTDLSMHW (SEQ ID NO: 1), a CDR2 comprising YITPSSGYTAYNQKFKG (SEQ ID NO: 2), a CDR3 comprising LILQRGAY (SEQ ID NO: 3) and a human heavy chain constant region; and
   the light chain comprises a CDR1 comprising RASKNVDSYGNSFMHW (SEQ ID NO: 4), a CDR2 comprising RASNLES (SEQ ID NO: 5), and a CDR3 comprising QQSNEDPLT (SEQ ID NO: 6) and a human light chain constant region, and
   the human heavy chain constant region is a human IgG1 Fc domain comprising a mutation at Kabat position 238 that reduces binding to Fc-gamma-receptors (FcgRs), wherein proline 238 (P238) is mutated to one of the residues selected from the group consisting of: lysine, serine, alanine, and arginine, and wherein the antibody or antigen binding portion has binding to at least one FcgR selected from hCD32a/FcgRIIa, hCD32b/FcgRIIb, hCD16a/FcgRIIIa, or hCD16b/FcgRIIIb.

2. The isolated antibody, or antigen binding portion thereof of claim 1, wherein the antibody or antigen binding portion thereof antagonizes activities of CD40.

3. The isolated antibody or antigen binding portion thereof of claim 1, wherein the heavy chain variable region comprises the amino acid sequence of SEQ ID NO: 7 and the light chain variable region comprises the amino acid sequence of SEQ ID NO: 8.

4. The isolated antibody, or antigen binding portion thereof of claim 1, wherein P238 is mutated to serine.

5. The isolated antibody, or antigen binding portion thereof of claim 1, wherein P238 is mutated to lysine.

6. The isolated antibody, or antigen binding portion thereof of claim 5, wherein the Fc domain comprises an amino acid sequence selected from the group consisting of: SEQ ID NO: 98 (IgG1a-P238K (-C-term Lys)), SEQ ID NO: 9 (IgG1a-P238K), SEQ ID NO: 99 (CH1-IgG1a-P238K (-C-term Lys)), SEQ ID NO: 10 (CH1-IgG1a-P238K), SEQ ID NO: 100 (IgG1f-P238K (-C-term Lys)), SEQ ID NO: 11 (IgG1f-P238K), SEQ ID NO: 101 (CH1-IgG1f-P238K (-C-term Lys)), and SEQ ID No: 12 (CH1-IgG1f-P238K).

7. The isolated antibody, or antigen binding portion thereof of claim 3, wherein the human IgG1 Fc domain comprises the amino acid sequence of SEQ ID NO: 98 or SEQ ID NO: 100.

8. The isolated antibody, or antigen binding portion thereof of claim 1, wherein the heavy chain comprises or consists of an amino acid sequence selected from the group consisting of: SEQ ID NO: 85, SEQ ID NO: 106, SEQ ID NO: 107, and SEQ ID NO: 108; and the light chain comprises or consists of the amino acid sequence of SEQ ID NO: 88.

9. The isolated antibody, or antigen binding portion thereof of claim 1, wherein the antibody or antigen binding portion thereof is humanized.

10. The isolated antibody, or antigen binding portion thereof of claim 1, wherein the antibody or antigen-binding portion thereof is linked to a therapeutic agent.

11. The isolated antibody, or antigen binding portion thereof of claim 1, wherein the antibody or antigen-binding portion thereof is linked to a second functional moiety having a different binding specificity than the antibody or antigen binding portion thereof.

12. A pharmaceutical composition comprising: a) the isolated antibody, or antigen binding portion thereof, of claim 1; and b) a pharmaceutically acceptable carrier.

13. A method of treating an immune response by antagonizing CD40 activity in a subject comprising administering to the subject the isolated antibody, or the antigen binding portion thereof, of claim 1.

14. The isolated antibody, or antigen binding portion thereof of claim 4, wherein the Fc domain comprises an amino acid sequence selected from the group consisting of: SEQ ID NO: 98 (IgG1a-P238K (-C-term Lys)), SEQ ID NO: 9 (IgG1a-P238K), SEQ ID NO: 99 (CH1-IgG1a-P238K (-C-term Lys)), SEQ ID NO: 10 (CH1-IgG1a-P238K), SEQ ID NO: 100 (IgG1f-P238K (-C-term Lys)), SEQ ID NO: 11 (IgG1f-P238K), SEQ ID NO: 101 (CH1-IgG1f-P238K (-C-term Lys)), and SEQ ID No: 12 (CH1-IgG1f-P238K).

15. The method of claim 13, wherein the subject has a disease selected from the group consisting of: Addison's disease, allergies, anaphylaxis, ankylosing spondylitis, asthma, atherosclerosis, atopic allergy, autoimmune diseases of the ear, autoimmune diseases of the eye, autoimmune hepatitis, autoimmune parotitis, bronchial asthma, coronary heart disease, Crohn's disease, diabetes, epididymitis, glomerulonephritis, Graves' disease, Guillain-Barre syndrome, Hashimoto's disease, hemolytic anemia, idiopathic thrombocytopenic purpura, inflammatory bowel disease, immune response to recombinant drug products, systemic lupus erythematosus, multiple sclerosis, myasthenia gravis, pemphigus, psoriasis, rheumatic fever, rheumatoid arthritis, sarcoidosis, scleroderma, Sjogren's syndrome, spondyloarthropathies, thyroiditis, transplant rejection, vasculitis, and ulcerative colitis.

* * * * *

UNITED STATES PATENT AND TRADEMARK OFFICE
CERTIFICATE OF CORRECTION

| | |
|---|---|
| PATENT NO. | : 11,220,550 B2 |
| APPLICATION NO. | : 15/988554 |
| DATED | : January 11, 2022 |
| INVENTOR(S) | : Aaron Yamniuk et al. |

It is certified that error appears in the above-identified patent and that said Letters Patent is hereby corrected as shown below:

In the Claims

At Column 191, Claim number 1, Line number 39, "or antigen binding portion has binding to at least one" should read -- or antigen binding portion has reduced binding to at least one --

Signed and Sealed this
Eighteenth Day of April, 2023

Katherine Kelly Vidal
*Director of the United States Patent and Trademark Office*

SEQUENCE LISTING

```
<160> NUMBER OF SEQ ID NOS: 119

<210> SEQ ID NO 1
<211> LENGTH: 11
<212> TYPE: PRT
<213> ORGANISM: Artificial Sequence
<220> FEATURE:
<223> OTHER INFORMATION: Synthetic peptide: 5F11-45-VH_CDR1

<400> SEQUENCE: 1

Gly Tyr Thr Phe Thr Asp Leu Ser Met His Trp
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic peptide: 5F11-45-VH_CDR2

<400> SEQUENCE: 2

Tyr Ile Thr Pro Ser Ser Gly Tyr Thr Ala Tyr Asn Gln Lys Phe Lys
1               5                   10                  15

Gly

<210> SEQ ID NO 3
<211> LENGTH: 8
<212> TYPE: PRT
<213> ORGANISM: Artificial Sequence
<220> FEATURE:
<223> OTHER INFORMATION: Synthetic peptide: 5F11-45-VH_CDR3
```

```
<400> SEQUENCE: 3

Leu Ile Leu Gln Arg Gly Ala Tyr
1               5

<210> SEQ ID NO 4
<211> LENGTH: 16
<212> TYPE: PRT
<213> ORGANISM: Artificial Sequence
<220> FEATURE:
<223> OTHER INFORMATION: Synthetic peptide: 5F11-45-VL_CDR1

<400> SEQUENCE: 4

Arg Ala Ser Lys Asn Val Asp Ser Tyr Gly Asn Ser Phe Met His Trp
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide: 5F11-45-VL_CDR2

<400> SEQUENCE: 5

Arg Ala Ser Asn Leu Glu Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide: 5F11-45-VL_CDR3

<400> SEQUENCE: 6

Gln Gln Ser Asn Glu Asp Pro Leu Thr
1               5

<210> SEQ ID NO 7
<211> LENGTH: 117
<212> TYPE: PRT
<213> ORGANISM: Artificial Sequence
<220> FEATURE:
<223> OTHER INFORMATION: Synthetic polypeptide: HC_VH_ 5F11-45

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Leu
            20                  25                  30

Ser Met His Trp Val Arg Gln Ala Pro Gly Gln Gly Leu Glu Trp Met
        35                  40                  45

Gly Tyr Ile Thr Pro Ser Ser Gly Tyr Thr Ala Tyr Asn Gln Lys Phe
    50                  55                  60

Lys Gly Lys Thr Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ile Leu Gln Arg Gly Ala Tyr Trp Gly Gln Gly Thr Leu
            100                 105                 110

Val Thr Val Ser Ser
            115
```

```
<210> SEQ ID NO 8
<211> LENGTH: 111
<212> TYPE: PRT
<213> ORGANISM: Artificial Sequence
<220> FEATURE:
<223> OTHER INFORMATION: Synthetic polypeptide: LC_VL_ 5F11-45

<400> SEQUENCE: 8

Asp Ile Val Leu Thr Gln Ser Pro Asp Ser Leu Ala Val Ser Leu Gly
 1               5                  10                  15

Glu Arg Ala Thr Ile Asn Cys Arg Ala Ser Lys Asn Val Asp Ser Tyr
             20                  25                  30

Gly Asn Ser Phe Met His Trp Tyr Gln Gln Lys Pro Gly Gln Pro Pro
         35                  40                  45

Lys Leu Leu Ile Tyr Arg Ala Ser Asn Leu Glu Ser Gly Val Pro Asp
     50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Asn
                 85                  90                  95

Glu Asp Pro Leu Thr Phe Gly Gln Gly Thr Lys Leu Glu Ile Lys
            100                 105                 110

<210> SEQ ID NO 9
<211> LENGTH: 232
<212> TYPE: PRT
<213> ORGANISM: Artificial Sequence
<220> FEATURE:
<223> OTHER INFORMATION: Synthetic polypeptide: Fc domain IgG1a-P238K

<400> SEQUENCE: 9

Glu Pro Lys Ser Cys Asp Lys Thr His Thr Cys Pro Pro Cys Pro Ala
 1               5                  10                  15

Pro Glu Leu Leu Gly Gly Lys Ser Val Phe Leu Phe Pro Pro Lys Pro
             20                  25                  30

Lys Asp Thr Leu Met Ile Ser Arg Thr Pro Glu Val Thr Cys Val Val
         35                  40                  45

Val Asp Val Ser His Glu Asp Pro Glu Val Lys Phe Asn Trp Tyr Val
     50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205
```

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 10
<211> LENGTH: 330
<212> TYPE: PRT
<213> ORGANISM: Artificial Sequence
<220> FEATURE:
<223> OTHER INFORMATION: Synthetic polypeptide: 5F11-CH1- IgG1a-P238K

<400> SEQUENCE: 10

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Lys Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 11
<211> LENGTH: 232
<212> TYPE: PRT
<213> ORGANISM: Artificial Sequence
<220> FEATURE:
<223> OTHER INFORMATION: Synthetic polypeptide: Fc domain IgG1f-P238K

<400> SEQUENCE: 11

Glu Pro Lys Ser Cys Asp Lys Thr His Thr Cys Pro Pro Cys Pro Ala
1               5                   10                  15

Pro Glu Leu Leu Gly Gly Lys Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 12
<211> LENGTH: 330
<212> TYPE: PRT
<213> ORGANISM: Artificial Sequence
<220> FEATURE:
<223> OTHER INFORMATION: Synthetic polypeptide: 5F11-CH1- IgG1f-P238K

<400> SEQUENCE: 12

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr

```
                65                  70                  75                  80
Tyr Ile Cys Asn Val Asn His Lys Pro Ser Asn Thr Lys Val Asp Lys
                    85                  90                  95
Arg Val Glu Pro Lys Ser Cys Asp Lys Thr His Thr Cys Pro Pro Cys
                    100                 105                 110
Pro Ala Pro Glu Leu Leu Gly Gly Lys Ser Val Phe Leu Phe Pro Pro
                    115                 120                 125
Lys Pro Lys Asp Thr Leu Met Ile Ser Arg Thr Pro Glu Val Thr Cys
                130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                    165                 170                 175
Glu Gln Tyr Asn Ser Thr Tyr Arg Val Val Ser Val Leu Thr Val Leu
                    180                 185                 190
His Gln Asp Trp Leu Asn Gly Lys Glu Tyr Lys Cys Lys Val Ser Asn
                    195                 200                 205
Lys Ala Leu Pro Ala Pro Ile Glu Lys Thr Ile Ser Lys Ala Lys Gly
                210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                    245                 250                 255
Pro Ser Asp Ile Ala Val Glu Trp Glu Ser Asn Gly Gln Pro Glu Asn
                    260                 265                 270
Asn Tyr Lys Thr Thr Pro Pro Val Leu Asp Ser Asp Gly Ser Phe Phe
                    275                 280                 285
Leu Tyr Ser Lys Leu Thr Val Asp Lys Ser Arg Trp Gln Gln Gly Asn
                290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                    325                 330

<210> SEQ ID NO 13
<211> LENGTH: 232
<212> TYPE: PRT
<213> ORGANISM: Artificial Sequence
<220> FEATURE:
<223> OTHER INFORMATION: Synthetic polypeptide: Fc domain IgG1a-N297A

<400> SEQUENCE: 13

Glu Pro Lys Ser Cys Asp Lys Thr His Thr Cys Pro Pro Cys Pro Ala
1               5                   10                  15
Pro Glu Leu Leu Gly Gly Pro Ser Val Phe Leu Phe Pro Pro Lys Pro
                    20                  25                  30
Lys Asp Thr Leu Met Ile Ser Arg Thr Pro Glu Val Thr Cys Val Val
                35                  40                  45
Val Asp Val Ser His Glu Asp Pro Glu Val Lys Phe Asn Trp Tyr Val
                50                  55                  60
Asp Gly Val Glu Val His Asn Ala Lys Thr Lys Pro Arg Glu Glu Gln
65                  70                  75                  80
Tyr Ala Ser Thr Tyr Arg Val Val Ser Val Leu Thr Val Leu His Gln
                    85                  90                  95
Asp Trp Leu Asn Gly Lys Glu Tyr Lys Cys Lys Val Ser Asn Lys Ala
```

```
                    100                 105                 110
Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 14
<211> LENGTH: 330
<212> TYPE: PRT
<213> ORGANISM: Artificial Sequence
<220> FEATURE:
<223> OTHER INFORMATION: Synthetic polypeptide: 5F11-CH1- IgG1a-N297A

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
```

```
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
                275                 280                 285
Leu Tyr Ser Lys Leu Thr Val Asp Lys Ser Arg Trp Gln Gln Gly Asn
            290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 15
<211> LENGTH: 232
<212> TYPE: PRT
<213> ORGANISM: Artificial Sequence
<220> FEATURE:
<223> OTHER INFORMATION: Synthetic polypeptide: Fc domain IgG1f-N297A

<400> SEQUENCE: 15

Glu Pro Lys Ser Cys Asp Lys Thr His Thr Cys Pro Pro Cys Pro Ala
1               5                   10                  15
Pro Glu Leu Leu Gly Gly Pro Ser Val Phe Leu Phe Pro Pro Lys Pro
            20                  25                  30
Lys Asp Thr Leu Met Ile Ser Arg Thr Pro Glu Val Thr Cys Val Val
        35                  40                  45
Val Asp Val Ser His Glu Asp Pro Glu Val Lys Phe Asn Trp Tyr Val
    50                  55                  60
Asp Gly Val Glu Val His Asn Ala Lys Thr Lys Pro Arg Glu Glu Gln
65                  70                  75                  80
Tyr Ala Ser Thr Tyr Arg Val Val Ser Val Leu Thr Val Leu His Gln
                85                  90                  95
Asp Trp Leu Asn Gly Lys Glu Tyr Lys Cys Lys Val Ser Asn Lys Ala
            100                 105                 110
Leu Pro Ala Pro Ile Glu Lys Thr Ile Ser Lys Ala Lys Gly Gln Pro
        115                 120                 125
Arg Glu Pro Gln Val Tyr Thr Leu Pro Pro Ser Arg Glu Glu Met Thr
    130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Tyr
            180                 185                 190
Ser Lys Leu Thr Val Asp Lys Ser Arg Trp Gln Gln Gly Asn Val Phe
        195                 200                 205
Ser Cys Ser Val Met His Glu Ala Leu His Asn His Tyr Thr Gln Lys
    210                 215                 220
Ser Leu Ser Leu Ser Pro Gly Lys
225                 230

<210> SEQ ID NO 16
<211> LENGTH: 330
<212> TYPE: PRT
```

-continued

```
<213> ORGANISM: Artificial Sequence
<220> FEATURE:
<223> OTHER INFORMATION: Synthetic polypeptide: 5F11-CH1- IgG1f-N297A

<400> SEQUENCE: 16

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 17
<211> LENGTH: 10
<212> TYPE: PRT
<213> ORGANISM: Artificial Sequence
<220> FEATURE:
<223> OTHER INFORMATION: Synthetic peptide: Y1238-VH_CDR1

<400> SEQUENCE: 17
```

Gly Tyr Ala Phe Thr Asn Tyr Leu Ile Glu
1               5                   10

<210> SEQ ID NO 18
<211> LENGTH: 17
<212> TYPE: PRT
<213> ORGANISM: Artificial Sequence
<220> FEATURE:
<223> OTHER INFORMATION: Synthetic peptide: Y1238-VH_CDR2

<400> SEQUENCE: 18

Val Ile Asn Pro Gly Ser Gly Gly Thr Asn Tyr Asn Glu Lys Phe Lys
1               5                   10                  15

Gly

<210> SEQ ID NO 19
<211> LENGTH: 9
<212> TYPE: PRT
<213> ORGANISM: Artificial Sequence
<220> FEATURE:
<223> OTHER INFORMATION: Synthetic peptide: Y1238-VH_CDR3

<400> SEQUENCE: 19

Ser Gln Leu Gly Arg Arg Phe Asp Tyr
1               5

<210> SEQ ID NO 20
<211> LENGTH: 11
<212> TYPE: PRT
<213> ORGANISM: Artificial Sequence
<220> FEATURE:
<223> OTHER INFORMATION: Synthetic peptide: Y1238-VL_CDR1

<400> SEQUENCE: 20

Lys Ala Ser Gln Asp Val Arg Thr Gly Val Ala
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Synthetic peptide: Y1238-VL_CDR2

<400> SEQUENCE: 21

Ser Ala Ser Tyr Arg Asn Thr
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic peptide: Y1238-VL_CDR3

<400> SEQUENCE: 22

Gln Gln His Tyr Ser Pro Pro Tyr Thr
1               5

<210> SEQ ID NO 23
<211> LENGTH: 118
<212> TYPE: PRT
<213> ORGANISM: Artificial Sequence
<220> FEATURE:
<223> OTHER INFORMATION: Synthetic polypeptide: hz-HC1 (h-Y1238_VH)

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gln Leu Gly Arg Arg Phe Asp Tyr Trp Gly Gln Gly Thr
            100                 105                 110

Leu Val Thr Val Ser Ser
        115

<210> SEQ ID NO 24
<211> LENGTH: 118
<212> TYPE: PRT
<213> ORGANISM: Artificial Sequence
<220> FEATURE:
<223> OTHER INFORMATION: Synthetic polypeptide: hz-HC2

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Lys Phe
    50                  55                  60

Lys Gly Arg Val Thr Met Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gln Leu Gly Arg Arg Phe Asp Tyr Trp Gly Gln Gly Thr
            100                 105                 110

Leu Val Thr Val Ser Ser
        115

<210> SEQ ID NO 25
<211> LENGTH: 118
<212> TYPE: PRT
<213> ORGANISM: Artificial Sequence
<220> FEATURE:
<223> OTHER INFORMATION: Synthetic polypeptide: hz-HC3

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Lys Phe

```
                   50                  55                  60
Lys Gly Arg Val Thr Met Thr Arg Asp Lys Ser Ile Ser Thr Ala Tyr
 65                  70                  75                  80

Met Glu Leu Ser Arg Leu Arg Ser Asp Asp Thr Ala Val Tyr Tyr Cys
                     85                  90                  95

Ala Arg Ser Gln Leu Gly Arg Arg Phe Asp Tyr Trp Gly Gln Gly Thr
                100                 105                 110

Leu Val Thr Val Ser Ser
                115

<210> SEQ ID NO 26
<211> LENGTH: 118
<212> TYPE: PRT
<213> ORGANISM: Artificial Sequence
<220> FEATURE:
<223> OTHER INFORMATION: Synthetic polypeptide: hz-HC4

<400> SEQUENCE: 26

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Ala Phe Thr Asn Tyr
                 20                  25                  30

Leu Ile Glu Trp Val Arg Gln Ala Pro Gly Gln Gly Leu Glu Trp Met
             35                  40                  45

Gly Val Ile Asn Pro Gly Ser Gly Gly Thr Asn Tyr Asn Glu Lys Phe
         50                  55                  60

Lys Gly Arg Val Thr Met Thr Ala Asp Lys Ser Ile Ser Thr Ala Tyr
 65                  70                  75                  80

Met Glu Leu Ser Arg Leu Arg Ser Asp Asp Thr Ala Val Tyr Tyr Cys
                     85                  90                  95

Ala Arg Ser Gln Leu Gly Arg Arg Phe Asp Tyr Trp Gly Gln Gly Thr
                100                 105                 110

Leu Val Thr Val Ser Ser
                115

<210> SEQ ID NO 27
<211> LENGTH: 118
<212> TYPE: PRT
<213> ORGANISM: Artificial Sequence
<220> FEATURE:
<223> OTHER INFORMATION: Synthetic polypeptide: hz-HC5

<400> SEQUENCE: 27

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Ala Phe Thr Asn Tyr
                 20                  25                  30

Leu Ile Glu Trp Val Arg Gln Arg Pro Gly Gln Gly Leu Glu Trp Met
             35                  40                  45

Gly Val Ile Asn Pro Gly Ser Gly Gly Thr Asn Tyr Asn Glu Lys Phe
         50                  55                  60

Lys Gly Arg Val Thr Met Thr Ala Asp Lys Ser Ile Ser Thr Ala Tyr
 65                  70                  75                  80

Met Glu Leu Ser Arg Leu Arg Ser Asp Asp Thr Ala Val Tyr Tyr Cys
                     85                  90                  95

Ala Arg Ser Gln Leu Gly Arg Arg Phe Asp Tyr Trp Gly Gln Gly Thr
                100                 105                 110
```

```
Leu Val Thr Val Ser Ser
        115

<210> SEQ ID NO 28
<211> LENGTH: 118
<212> TYPE: PRT
<213> ORGANISM: Artificial Sequence
<220> FEATURE:
<223> OTHER INFORMATION: Synthetic polypeptide: hz-HC6

<400> SEQUENCE: 28

Gln Val Gln Leu Val Gln Ser Gly Ala Glu Val Lys Pro Gly Ala
1               5                   10                  15

Ser Val Lys Val Ser Cys Lys Ala Ser Gly Tyr Ala Phe Thr Asn Tyr
                20                  25                  30

Leu Ile Glu Trp Val Arg Gln Arg Pro Gly Gln Gly Leu Glu Trp Met
            35                  40                  45

Gly Val Ile Asn Pro Gly Ser Gly Gly Thr Asn Tyr Asn Glu Lys Phe
        50                  55                  60

Lys Gly Arg Val Thr Leu Thr Ala Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gln Leu Gly Arg Arg Phe Asp Tyr Trp Gly Gln Gly Thr
            100                 105                 110

Leu Val Thr Val Ser Ser
        115

<210> SEQ ID NO 29
<211> LENGTH: 118
<212> TYPE: PRT
<213> ORGANISM: Artificial Sequence
<220> FEATURE:
<223> OTHER INFORMATION: Synthetic polypeptide: hz-HC7

<400> SEQUENCE: 29

Gln Val Gln Leu Val Gln Ser Gly Ala Glu Val Val Lys Pro Gly Ala
1               5                   10                  15

Ser Val Lys Val Ser Cys Lys Ala Ser Gly Tyr Ala Phe Thr Asn Tyr
                20                  25                  30

Leu Ile Glu Trp Val Arg Gln Arg Pro Gly Gln Gly Leu Glu Trp Met
            35                  40                  45

Gly Val Ile Asn Pro Gly Ser Gly Gly Thr Asn Tyr Asn Glu Lys Phe
        50                  55                  60

Lys Gly Arg Val Thr Met Thr Ala Asp Lys Ser Ser Ser Thr Ala Tyr
65                  70                  75                  80

Met Gln Leu Ser Arg Leu Arg Ser Asp Asp Thr Ala Val Tyr Phe Cys
                85                  90                  95

Ala Arg Ser Gln Leu Gly Arg Arg Phe Asp Tyr Trp Gly Gln Gly Thr
            100                 105                 110

Leu Val Thr Val Ser Ser
        115

<210> SEQ ID NO 30
<211> LENGTH: 118
<212> TYPE: PRT
<213> ORGANISM: Artificial Sequence
<220> FEATURE:
<223> OTHER INFORMATION: Synthetic polypeptide: hz-HC8
```

```
<400> SEQUENCE: 30

Gln Val Gln Leu Val Gln Ser Gly Ala Glu Val Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Arg Pro Gly Gln Gly Leu Glu Trp Met
        35                  40                  45

Gly Val Ile Asn Pro Gly Ser Gly Gly Thr Asn Tyr Asn Glu Lys Phe
    50                  55                  60

Lys Gly Arg Val Thr Leu Thr Ala Asp Lys Ser Ser Ser Thr Ala Tyr
65                  70                  75                  80

Met Gln Leu Ser Arg Leu Arg Ser Asp Asp Thr Ala Val Tyr Phe Cys
                85                  90                  95

Ala Arg Ser Gln Leu Gly Arg Arg Phe Asp Tyr Trp Gly Gln Gly Thr
                100                 105                 110

Leu Val Thr Val Ser Ser
        115

<210> SEQ ID NO 31
<211> LENGTH: 118
<212> TYPE: PRT
<213> ORGANISM: Artificial Sequence
<220> FEATURE:
<223> OTHER INFORMATION: Synthetic polypeptide: hz-HC9

<400> SEQUENCE: 31

Gln Val Gln Leu Val Gln Ser Gly Ala Glu Val Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Arg Pro Gly Gln Gly Leu Glu Trp Met
        35                  40                  45

Gly Val Ile Asn Pro Gly Ser Gly Gly Thr Asn Tyr Asn Glu Lys Phe
    50                  55                  60

Lys Gly Arg Val Thr Leu Thr Ala Asp Lys Ser Ser Ser Thr Ala Tyr
65                  70                  75                  80

Met Gln Leu Ser Arg Leu Arg Ser Asp Asp Thr Ala Val Tyr Phe Cys
                85                  90                  95

Ala Arg Ser Gln Leu Gly Arg Arg Phe Asp Tyr Trp Gly Gln Gly Thr
                100                 105                 110

Thr Val Thr Val Ser Ser
        115

<210> SEQ ID NO 32
<211> LENGTH: 118
<212> TYPE: PRT
<213> ORGANISM: Artificial Sequence
<220> FEATURE:
<223> OTHER INFORMATION: Synthetic polypeptide: hz-HC10

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Arg Pro Gly Gln Gly Leu Glu Trp Met
        35                  40                  45
```

Gly Val Ile Asn Pro Gly Ser Gly Gly Thr Asn Tyr Asn Glu Lys Phe
            50                  55                  60

Lys Gly Arg Val Thr Met Thr Arg Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gln Leu Gly Arg Arg Phe Asp Tyr Trp Gly Gln Gly Thr
                100                 105                 110

Leu Val Thr Val Ser Ser
            115

<210> SEQ ID NO 33
<211> LENGTH: 118
<212> TYPE: PRT
<213> ORGANISM: Artificial Sequence
<220> FEATURE:
<223> OTHER INFORMATION: Synthetic polypeptide: hz-HC11

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
                20                  25                  30

Leu Ile Glu Trp Val Arg Gln Arg Pro Gly Gln Gly Leu Glu Trp Met
            35                  40                  45

Gly Val Ile Asn Pro Gly Ser Gly Gly Thr Asn Tyr Asn Glu Lys Phe
            50                  55                  60

Lys Gly Arg Val Thr Met Thr Arg Asp Lys Ser Ser Thr Ala Tyr
65                  70                  75                  80

Met Glu Leu Ser Arg Leu Arg Ser Asp Asp Thr Ala Val Tyr Phe Cys
                85                  90                  95

Ala Arg Ser Gln Leu Gly Arg Arg Phe Asp Tyr Trp Gly Gln Gly Thr
                100                 105                 110

Leu Val Thr Val Ser Ser
            115

<210> SEQ ID NO 34
<211> LENGTH: 107
<212> TYPE: PRT
<213> ORGANISM: Artificial Sequence
<220> FEATURE:
<223> OTHER INFORMATION: Synthetic polypeptide: hz-LC1

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Arg Thr Gly
                20                  25                  30

Val Ala Trp Tyr Gln Gln Lys Pro Gly Lys Ala Pro Lys Leu Leu Ile
            35                  40                  45

Tyr Ser Ala Ser Tyr Arg Asn Thr Gly Val Pro Ser Arg Phe Ser Gly
            50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Pro Pro Tyr
                85                  90                  95

Thr Phe Gly Gly Gly Thr Lys Val Glu Ile Lys
                100                 105

<210> SEQ ID NO 35
<211> LENGTH: 107
<212> TYPE: PRT
<213> ORGANISM: Artificial Sequence
<220> FEATURE:
<223> OTHER INFORMATION: Synthetic polypeptide: hz-LC2

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Arg Thr Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Asn Thr Gly Val Pro Ser Arg Phe Ser Gly
    50                  55                  60

Ser Arg Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Pro Pro Tyr
                85                  90                  95

Thr Phe Gly Gly Gly Thr Lys Val Glu Ile Lys
            100                 105

<210> SEQ ID NO 36
<211> LENGTH: 107
<212> TYPE: PRT
<213> ORGANISM: Artificial Sequence
<220> FEATURE:
<223> OTHER INFORMATION: Synthetic polypeptide: hz-LC3

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Arg Thr Gly
            20                  25                  30

Val Ala Trp Tyr Gln Gln Lys Pro Gly Gln Ser Pro Lys Leu Leu Ile
        35                  40                  45

Tyr Ser Ala Ser Tyr Arg Asn Thr Gly Val Pro Ser Arg Phe Ser Gly
    50                  55                  60

Ser Arg Ser Gly Thr Asp Phe Thr Phe Thr Ile Ser Ser Leu Gln Pro
65                  70                  75                  80

Glu Asp Ile Ala Val Tyr Tyr Cys Gln Gln His Tyr Ser Pro Pro Tyr
                85                  90                  95

Thr Phe Gly Gly Gly Thr Lys Val Glu Ile Lys
            100                 105

<210> SEQ ID NO 37
<211> LENGTH: 107
<212> TYPE: PRT
<213> ORGANISM: Artificial Sequence
<220> FEATURE:
<223> OTHER INFORMATION: Synthetic polypeptide: hz-LC4

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Arg Thr Gly
            20                  25                  30

Val Ala Trp Tyr Gln Gln Lys Pro Gly Gln Ser Pro Lys Leu Leu Ile
            35                  40                  45

Tyr Ser Ala Ser Tyr Arg Asn Thr Gly Val Pro Ser Arg Phe Ser Gly
        50                  55                  60

Ser Arg Ser Gly Thr Asp Phe Thr Phe Thr Ile Ser Ser Leu Gln Ala
65                  70                  75                  80

Glu Asp Ile Ala Val Tyr Tyr Cys Gln Gln His Tyr Ser Pro Pro Tyr
                85                  90                  95

Thr Phe Gly Gly Gly Thr Lys Val Glu Ile Lys
                100                 105

<210> SEQ ID NO 38
<211> LENGTH: 107
<212> TYPE: PRT
<213> ORGANISM: Artificial Sequence
<220> FEATURE:
<223> OTHER INFORMATION: Synthetic polypeptide: hz-LC5

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Arg Thr Gly
            20                  25                  30

Val Ala Trp Tyr Gln Gln Lys Pro Gly Gln Ala Pro Lys Leu Leu Ile
            35                  40                  45

Tyr Ser Ala Ser Tyr Arg Asn Thr Gly Val Pro Ser Arg Phe Ser Gly
        50                  55                  60

Ser Arg Ser Gly Thr Asp Phe Thr Phe Thr Ile Ser Ser Leu Gln Pro
65                  70                  75                  80

Glu Asp Ile Ala Val Tyr Tyr Cys Gln Gln His Tyr Ser Pro Pro Tyr
                85                  90                  95

Thr Phe Gly Gly Gly Thr Lys Val Glu Ile Lys
                100                 105

<210> SEQ ID NO 39
<211> LENGTH: 447
<212> TYPE: PRT
<213> ORGANISM: Artificial Sequence
<220> FEATURE:
<223> OTHER INFORMATION: Synthetic polypeptide: HC_Y1238-hz1-P238K

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Met
            35                  40                  45

Gly Val Ile Asn Pro Gly Ser Gly Gly Thr Asn Tyr Asn Glu Lys Phe
        50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gln Leu Gly Arg Arg Phe Asp Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Lys Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 40
<211> LENGTH: 447
<212> TYPE: PRT
<213> ORGANISM: Artificial Sequence
<220> FEATURE:
<223> OTHER INFORMATION: Synthetic polypeptide: HC_Y1238-hz1-N297A

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

```
Gly Val Ile Asn Pro Gly Ser Gly Thr Asn Tyr Asn Glu Lys Phe
 50                  55                  60

Lys Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Ser Gln Leu Gly Arg Arg Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 41
<211> LENGTH: 214
```

<212> TYPE: PRT
<213> ORGANISM: Artificial Sequence
<220> FEATURE:
<223> OTHER INFORMATION: Synthetic polypeptide: LC_Y1238-hz1

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Arg Thr Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Asn Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Pro Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 42
<211> LENGTH: 447
<212> TYPE: PRT
<213> ORGANISM: Artificial Sequence
<220> FEATURE:
<223> OTHER INFORMATION: Synthetic polypeptide: HC_Y1238-hz2-P238K

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Thr Asn Tyr Asn Glu Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gln Leu Gly Arg Arg Phe Asp Tyr Trp Gly Gln Gly Thr
            100                 105                 110

```
Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
        210                 215                 220

His Thr Cys Pro Pro Cys Pro Ala Pro Glu Leu Leu Gly Gly Lys Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 43
<211> LENGTH: 447
<212> TYPE: PRT
<213> ORGANISM: Artificial Sequence
<220> FEATURE:
<223> OTHER INFORMATION: Synthetic polypeptide: HC_ Y1238-hz2-N297A

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
                20                  25                  30
```

-continued

Leu Ile Glu Trp Val Arg Gln Ala Pro Gly Gln Gly Leu Glu Trp Met
            35                  40                  45
Gly Val Ile Asn Pro Gly Ser Gly Gly Thr Asn Tyr Asn Glu Lys Phe
 50                  55                  60
Lys Gly Arg Val Thr Met Thr Arg Asp Thr Ser Ile Ser Thr Ala Tyr
 65                  70                  75                  80
Met Glu Leu Ser Arg Leu Arg Ser Asp Asp Thr Ala Val Tyr Tyr Cys
                 85                  90                  95
Ala Arg Ser Gln Leu Gly Arg Arg Phe Asp Tyr Trp Gly Gln Gly Thr
                100                 105                 110
Leu Val Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
            130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
            195                 200                 205
Asn Thr Lys Val Asp Lys Arg Val Glu Pro Lys Ser Cys Asp Lys Thr
            210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
            275                 280                 285
Lys Thr Lys Pro Arg Glu Glu Gln Tyr Ala Ser Thr Tyr Arg Val Val
            290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
            355                 360                 365
Leu Val Lys Gly Phe Tyr Pro Ser Asp Ile Ala Val Glu Trp Glu Ser
370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly
            435                 440                 445

<210> SEQ ID NO 44
<211> LENGTH: 214
<212> TYPE: PRT
<213> ORGANISM: Artificial Sequence
<220> FEATURE:
<223> OTHER INFORMATION: Synthetic polypeptide: LC_Y1238-hz2

<400> SEQUENCE: 44

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Arg Thr Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Asn Thr Gly Val Pro Ser Arg Phe Ser Gly
    50                  55                  60

Ser Arg Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Pro Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 45
<211> LENGTH: 277
<212> TYPE: PRT
<213> ORGANISM: Homo sapiens

<400> SEQUENCE: 45

```
Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
```

-continued

```
                100                 105                 110
Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
        130                 135                 140

Pro Cys Pro Val Gly Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
        180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
        210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
        260                 265                 270

Val Gln Glu Arg Gln
        275

<210> SEQ ID NO 46
<211> LENGTH: 25
<212> TYPE: PRT
<213> ORGANISM: Artificial Sequence
<220> FEATURE:
<223> OTHER INFORMATION: Synthetic peptide: 5F11-VH_FR1

<400> SEQUENCE: 46

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 47
<211> LENGTH: 25
<212> TYPE: PRT
<213> ORGANISM: Artificial Sequence
<220> FEATURE:
<223> OTHER INFORMATION: Synthetic peptide: Y1238-VH_FR1

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 48
<211> LENGTH: 25
<212> TYPE: PRT
<213> ORGANISM: Artificial Sequence
<220> FEATURE:
<223> OTHER INFORMATION: Synthetic peptide: Y1238-VH_FR1

<400> SEQUENCE: 48

Gln Val Gln Leu Val Gln Ser Gly Ala Glu Val Val Lys Pro Gly Ala
1               5                   10                  15
```

Ser Val Lys Val Ser Cys Lys Ala Ser
            20                  25

<210> SEQ ID NO 49
<211> LENGTH: 14
<212> TYPE: PRT
<213> ORGANISM: Artificial Sequence
<220> FEATURE:
<223> OTHER INFORMATION: Synthetic peptide: 5F11- and Y1238-VH_FR2

<400> SEQUENCE: 49

Trp Val Arg Gln Ala Pro Gly Gln Gly Leu Glu Trp Met Gly
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Synthetic peptide: Y1238-VH_FR2

<400> SEQUENCE: 50

Trp Val Arg Gln Arg Pro Gly Gln Gly Leu Glu Trp Met Gly
1               5                   10

<210> SEQ ID NO 51
<211> LENGTH: 32
<212> TYPE: PRT
<213> ORGANISM: Artificial Sequence
<220> FEATURE:
<223> OTHER INFORMATION: Synthetic polypeptide: 5F11-VH_FR3

<400> SEQUENCE: 51

Lys Thr Thr Leu Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 52
<211> LENGTH: 32
<212> TYPE: PRT
<213> ORGANISM: Artificial Sequence
<220> FEATURE:
<223> OTHER INFORMATION: Synthetic polypeptide: Y1238-VH_FR3

<400> SEQUENCE: 52

Arg Val Thr Met Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 53
<211> LENGTH: 32
<212> TYPE: PRT
<213> ORGANISM: Artificial Sequence
<220> FEATURE:
<223> OTHER INFORMATION: Synthetic polypeptide: Y1238-VH_FR3

<400> SEQUENCE: 53

Arg Val Thr Met Thr Ala Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

```
<210> SEQ ID NO 54
<211> LENGTH: 32
<212> TYPE: PRT
<213> ORGANISM: Artificial Sequence
<220> FEATURE:
<223> OTHER INFORMATION: Synthetic polypeptide: Y1238-VH_FR3

<400> SEQUENCE: 54

Arg Val Thr Met Thr Arg Asp Lys Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 55
<211> LENGTH: 32
<212> TYPE: PRT
<213> ORGANISM: Artificial Sequence
<220> FEATURE:
<223> OTHER INFORMATION: Synthetic polypeptide: Y1238-VH_FR3

<400> SEQUENCE: 55

Arg Val Thr Met Thr Ala Asp Lys Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 56
<211> LENGTH: 32
<212> TYPE: PRT
<213> ORGANISM: Artificial Sequence
<220> FEATURE:
<223> OTHER INFORMATION: Synthetic polypeptide: Y1238-VH_FR3

<400> SEQUENCE: 56

Arg Val Thr Leu Thr Ala Asp Lys Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 57
<211> LENGTH: 32
<212> TYPE: PRT
<213> ORGANISM: Artificial Sequence
<220> FEATURE:
<223> OTHER INFORMATION: Synthetic polypeptide: Y1238-VH_FR3

<400> SEQUENCE: 57

Arg Val Thr Met Thr Ala Asp Lys Ser Ser Ser Thr Ala Tyr Met Gln
1               5                   10                  15

Leu Ser Arg Leu Arg Ser Asp Asp Thr Ala Val Tyr Phe Cys Ala Arg
            20                  25                  30

<210> SEQ ID NO 58
<211> LENGTH: 32
<212> TYPE: PRT
<213> ORGANISM: Artificial Sequence
<220> FEATURE:
<223> OTHER INFORMATION: Synthetic polypeptide: Y1238-VH_FR3

<400> SEQUENCE: 58

Arg Val Thr Leu Thr Ala Asp Lys Ser Ser Ser Thr Ala Tyr Met Gln
1               5                   10                  15

Leu Ser Arg Leu Arg Ser Asp Asp Thr Ala Val Tyr Phe Cys Ala Arg
            20                  25                  30
```

```
<210> SEQ ID NO 59
<211> LENGTH: 32
<212> TYPE: PRT
<213> ORGANISM: Artificial Sequence
<220> FEATURE:
<223> OTHER INFORMATION: Synthetic polypeptide: Y1238-VH_FR3

<400> SEQUENCE: 59

Arg Val Thr Met Thr Arg Asp Lys Ser Ser Thr Ala Tyr Met Glu
1               5                   10                  15

Leu Ser Arg Leu Arg Ser Asp Asp Thr Ala Val Tyr Phe Cys Ala Arg
            20                  25                  30

<210> SEQ ID NO 60
<211> LENGTH: 11
<212> TYPE: PRT
<213> ORGANISM: Artificial Sequence
<220> FEATURE:
<223> OTHER INFORMATION: Synthetic peptide: 5F11- and Y1238-VH_FR4

<400> SEQUENCE: 60

Trp Gly Gln Gly Thr Leu Val Thr Val Ser Ser
1               5                   10

<210> SEQ ID NO 61
<211> LENGTH: 23
<212> TYPE: PRT
<213> ORGANISM: Artificial Sequence
<220> FEATURE:
<223> OTHER INFORMATION: Synthetic peptide: 5F11-VL_FR1

<400> SEQUENCE: 61

Asp Ile Val Leu Thr Gln Ser Pro Asp Ser Leu Ala Val Ser Leu Gly
1               5                   10                  15

Glu Arg Ala Thr Ile Asn Cys
            20

<210> SEQ ID NO 62
<211> LENGTH: 23
<212> TYPE: PRT
<213> ORGANISM: Artificial Sequence
<220> FEATURE:
<223> OTHER INFORMATION: Synthetic peptide: Y1238-VL_FR1

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 63
<211> LENGTH: 15
<212> TYPE: PRT
<213> ORGANISM: Artificial Sequence
<220> FEATURE:
<223> OTHER INFORMATION: Synthetic peptide: 5F11-VL_FR2

<400> SEQUENCE: 63

Trp Tyr Gln Gln Lys Pro Gly Gln Pro Pro Lys Leu Leu Ile Tyr
1               5                   10                  15

<210> SEQ ID NO 64
<211> LENGTH: 15
<212> TYPE: PRT
<213> ORGANISM: Artificial Sequence
```

```
<220> FEATURE:
<223> OTHER INFORMATION: Synthetic peptide: Y1238-VL_FR2

<400> SEQUENCE: 64

Trp Tyr Gln Gln Lys Pro Gly Lys Ala Pro Lys Leu Leu Ile Tyr
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Synthetic peptide: Y1238-VL_FR2

<400> SEQUENCE: 65

Trp Tyr Gln Gln Lys Pro Gly Gln Ser Pro Lys Leu Leu Ile Tyr
1               5                   10                  15

<210> SEQ ID NO 66
<211> LENGTH: 32
<212> TYPE: PRT
<213> ORGANISM: Artificial Sequence
<220> FEATURE:
<223> OTHER INFORMATION: Synthetic polypeptide: 5F11-VL_FR3

<400> SEQUENCE: 66

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 67
<211> LENGTH: 32
<212> TYPE: PRT
<213> ORGANISM: Artificial Sequence
<220> FEATURE:
<223> OTHER INFORMATION: Synthetic polypeptide: Y1238-VL_FR3

<400> SEQUENCE: 67

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 68
<211> LENGTH: 32
<212> TYPE: PRT
<213> ORGANISM: Artificial Sequence
<220> FEATURE:
<223> OTHER INFORMATION: Synthetic polypeptide: Y1238-VL_FR3

<400> SEQUENCE: 68

Gly Val Pro Ser Arg Phe Ser Gly Ser Arg Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 69
<211> LENGTH: 32
<212> TYPE: PRT
<213> ORGANISM: Artificial Sequence
<220> FEATURE:
<223> OTHER INFORMATION: Synthetic polypeptide: Y1238-VL_FR3

<400> SEQUENCE: 69
```

```
Gly Val Pro Ser Arg Phe Ser Gly Ser Arg Ser Gly Thr Asp Phe Thr
1               5                   10                  15

Phe Thr Ile Ser Ser Leu Gln Pro Glu Asp Ile Ala Val Tyr Tyr Cys
            20                  25                  30
```

<210> SEQ ID NO 70
<211> LENGTH: 32
<212> TYPE: PRT
<213> ORGANISM: Artificial Sequence
<220> FEATURE:
<223> OTHER INFORMATION: Synthetic polypeptide: Y1238-VL_FR3

<400> SEQUENCE: 70

```
Gly Val Pro Ser Arg Phe Ser Gly Ser Arg Ser Gly Thr Asp Phe Thr
1               5                   10                  15

Phe Thr Ile Ser Ser Leu Gln Ala Glu Asp Ile Ala Val Tyr Tyr Cys
            20                  25                  30
```

<210> SEQ ID NO 71
<211> LENGTH: 10
<212> TYPE: PRT
<213> ORGANISM: Artificial Sequence
<220> FEATURE:
<223> OTHER INFORMATION: Synthetic peptide: 5F11-VL_FR4

<400> SEQUENCE: 71

```
Phe Gly Gln Gly Thr Lys Leu Glu Ile Lys
1               5                   10
```

<210> SEQ ID NO 72
<211> LENGTH: 10
<212> TYPE: PRT
<213> ORGANISM: Artificial Sequence
<220> FEATURE:
<223> OTHER INFORMATION: Synthetic peptide: Y1238-VL_FR4

<400> SEQUENCE: 72

```
Phe Gly Gly Gly Thr Lys Val Glu Ile Lys
1               5                   10
```

<210> SEQ ID NO 73
<211> LENGTH: 5
<212> TYPE: PRT
<213> ORGANISM: Artificial Sequence
<220> FEATURE:
<223> OTHER INFORMATION: Synthetic peptide: Linker GGGGS

<400> SEQUENCE: 73

```
Gly Gly Gly Gly Ser
1               5
```

<210> SEQ ID NO 74
<211> LENGTH: 10
<212> TYPE: PRT
<213> ORGANISM: Artificial Sequence
<220> FEATURE:
<223> OTHER INFORMATION: Synthetic peptide: Linker (GGGGS)2

<400> SEQUENCE: 74

```
Gly Gly Gly Gly Ser Gly Gly Gly Gly Ser
1               5                   10
```

<210> SEQ ID NO 75
<211> LENGTH: 15
<212> TYPE: PRT
<213> ORGANISM: Artificial Sequence

```
<220> FEATURE:
<223> OTHER INFORMATION: Synthetic peptide: Linker (GGGGS)3

<400> SEQUENCE: 75

Gly Gly Gly Gly Ser Gly Gly Gly Gly Ser Gly Gly Gly Gly Ser
1               5                   10                  15

<210> SEQ ID NO 76
<211> LENGTH: 20
<212> TYPE: PRT
<213> ORGANISM: Artificial Sequence
<220> FEATURE:
<223> OTHER INFORMATION: Synthetic peptide: Linker (GGGGS)4

<400> SEQUENCE: 76

Gly Gly Gly Gly Ser Gly Gly Gly Gly Ser Gly Gly Gly Gly Ser Gly
1               5                   10                  15

Gly Gly Gly Ser
            20

<210> SEQ ID NO 77
<211> LENGTH: 25
<212> TYPE: PRT
<213> ORGANISM: Artificial Sequence
<220> FEATURE:
<223> OTHER INFORMATION: Synthetic peptide: Linker (GGGGS)5

<400> SEQUENCE: 77

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 78
<211> LENGTH: 3
<212> TYPE: PRT
<213> ORGANISM: Artificial Sequence
<220> FEATURE:
<223> OTHER INFORMATION: Synthetic peptide: Linker

<400> SEQUENCE: 78

Ala Ser Thr
1

<210> SEQ ID NO 79
<211> LENGTH: 6
<212> TYPE: PRT
<213> ORGANISM: Artificial Sequence
<220> FEATURE:
<223> OTHER INFORMATION: Synthetic peptide: Linker

<400> SEQUENCE: 79

Thr Val Ala Ala Pro Ser
1               5

<210> SEQ ID NO 80
<211> LENGTH: 3
<212> TYPE: PRT
<213> ORGANISM: Artificial Sequence
<220> FEATURE:
<223> OTHER INFORMATION: Synthetic peptide: Linker

<400> SEQUENCE: 80

Thr Val Ala
1
```

<210> SEQ ID NO 81
<211> LENGTH: 447
<212> TYPE: PRT
<213> ORGANISM: Artificial Sequence
<220> FEATURE:
<223> OTHER INFORMATION: Synthetic polypeptide: HC_ 5F11-45-IgG1f

<400> SEQUENCE: 81

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Leu
            20                  25                  30

Ser Met His Trp Val Arg Gln Ala Pro Gly Gln Gly Leu Glu Trp Met
        35                  40                  45

Gly Tyr Ile Thr Pro Ser Ser Gly Tyr Thr Ala Tyr Asn Gln Lys Phe
    50                  55                  60

Lys Gly Lys Thr Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ile Leu Gln Arg Gly Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365
```

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 82
<211> LENGTH: 447
<212> TYPE: PRT
<213> ORGANISM: Artificial Sequence
<220> FEATURE:
<223> OTHER INFORMATION: Synthetic polypeptide: HC_5F11-45-IgG1.3f (also
      referred to as HC_5F11-45-hIgG1.3f)

<400> SEQUENCE: 82

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Leu
            20                  25                  30

Ser Met His Trp Val Arg Gln Ala Pro Gly Gln Gly Leu Glu Trp Met
        35                  40                  45

Gly Tyr Ile Thr Pro Ser Ser Gly Tyr Thr Ala Tyr Asn Gln Lys Phe
    50                  55                  60

Lys Gly Lys Thr Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ile Leu Gln Arg Gly Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Glu Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

```
Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 83
<211> LENGTH: 447
<212> TYPE: PRT
<213> ORGANISM: Artificial Sequence
<220> FEATURE:
<223> OTHER INFORMATION: Synthetic polypeptide: HC_5F11-45-CTza

<400> SEQUENCE: 83

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Leu
            20                  25                  30

Ser Met His Trp Val Arg Gln Ala Pro Gly Gln Gly Leu Glu Trp Met
        35                  40                  45

Gly Tyr Ile Thr Pro Ser Ser Gly Tyr Thr Ala Tyr Asn Gln Lys Phe
50                  55                  60

Lys Gly Lys Thr Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ile Leu Gln Arg Gly Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205
```

```
Thr Lys Val Asp Lys Lys Val Glu Pro Lys Ser Cys Asp Lys Thr His
        210                 215                 220

Thr Ser Pro Pro Ser Pro Ala Pro Glu Leu Leu Gly Gly Ser Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 84
<211> LENGTH: 447
<212> TYPE: PRT
<213> ORGANISM: Artificial Sequence
<220> FEATURE:
<223> OTHER INFORMATION: Synthetic polypeptide: HC_5F11-45-N297A

<400> SEQUENCE: 84

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Leu
            20                  25                  30

Ser Met His Trp Val Arg Gln Ala Pro Gly Gln Gly Leu Glu Trp Met
        35                  40                  45

Gly Tyr Ile Thr Pro Ser Ser Gly Tyr Thr Ala Tyr Asn Gln Lys Phe
    50                  55                  60

Lys Gly Lys Thr Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ile Leu Gln Arg Gly Ala Tyr Trp Gly Gln Gly Thr Leu
            100                 105                 110

Val Thr Val Ser Ser Ala Ser Thr Lys Gly Pro Ser Val Phe Pro Leu
        115                 120                 125
```

```
Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 85
<211> LENGTH: 447
<212> TYPE: PRT
<213> ORGANISM: Artificial Sequence
<220> FEATURE:
<223> OTHER INFORMATION: Synthetic polypeptide: HC_5F11-45-P238K

<400> SEQUENCE: 85

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Leu
            20                  25                  30

Ser Met His Trp Val Arg Gln Ala Pro Gly Gln Gly Leu Glu Trp Met
        35                  40                  45
```

Gly Tyr Ile Thr Pro Ser Ser Gly Tyr Thr Ala Tyr Asn Gln Lys Phe
50                  55                  60

Lys Gly Lys Thr Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ile Leu Gln Arg Gly Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Lys Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 86
<211> LENGTH: 447

<212> TYPE: PRT
<213> ORGANISM: Artificial Sequence
<220> FEATURE:
<223> OTHER INFORMATION: Synthetic polypeptide: HC_5F11-45-SE

<400> SEQUENCE: 86

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Leu
            20                  25                  30

Ser Met His Trp Val Arg Gln Ala Pro Gly Gln Gly Leu Glu Trp Met
        35                  40                  45

Gly Tyr Ile Thr Pro Ser Ser Gly Tyr Thr Ala Tyr Asn Gln Lys Phe
    50                  55                  60

Lys Gly Lys Thr Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ile Leu Gln Arg Gly Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Glu His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380
```

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
        435                 440                 445

<210> SEQ ID NO 87
<211> LENGTH: 447
<212> TYPE: PRT
<213> ORGANISM: Artificial Sequence
<220> FEATURE:
<223> OTHER INFORMATION: Synthetic polypeptide: HC_5F11-45-V11

<400> SEQUENCE: 87

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Leu
            20                  25                  30

Ser Met His Trp Val Arg Gln Ala Pro Gly Gln Gly Leu Glu Trp Met
        35                  40                  45

Gly Tyr Ile Thr Pro Ser Ser Gly Tyr Thr Ala Tyr Asn Gln Lys Phe
    50                  55                  60

Lys Gly Lys Thr Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ile Leu Gln Arg Gly Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Asp Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Asp Glu Asp Gly Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Arg Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 88
<211> LENGTH: 218
<212> TYPE: PRT
<213> ORGANISM: Artificial Sequence
<220> FEATURE:
<223> OTHER INFORMATION: Synthetic polypeptide: LC_5F11-45

<400> SEQUENCE: 88

Asp Ile Val Leu Thr Gln Ser Pro Asp Ser Leu Ala Val Ser Leu Gly
1               5                   10                  15

Glu Arg Ala Thr Ile Asn Cys Arg Ala Ser Lys Asn Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 89
<211> LENGTH: 348
<212> TYPE: PRT
<213> ORGANISM: Artificial Sequence
<220> FEATURE:
<223> OTHER INFORMATION: Synthetic polypeptide: BMS-986090

<400> SEQUENCE: 89

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Glu Met Trp Trp Val Arg Gln Ala Pro Gly Lys Gly Leu Glu Arg Val
        35                  40                  45

Ser Ala Ile Asn Pro Gln Gly Thr Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Pro Phe Arg Phe Ser Asp Arg Gly Gln Gly Thr Leu Val
            100                 105                 110

Thr Val Ser Ser Ala Ser Thr Glu Ser Lys Tyr Gly Pro Pro Cys Pro
        115                 120                 125

Pro Cys Pro Ala Pro Glu Phe Leu Gly Gly Pro Ser Val Phe Leu Phe
    130                 135                 140

Pro Pro Lys Pro Lys Asp Thr Leu Met Ile Ser Arg Thr Pro Glu Val
145                 150                 155                 160

Thr Cys Val Val Val Asp Val Ser Gln Glu Asp Pro Glu Val Gln Phe
                165                 170                 175

Asn Trp Tyr Val Asp Gly Val Glu Val His Asn Ala Lys Thr Lys Pro
            180                 185                 190

Arg Glu Glu Gln Phe Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Gly Leu Pro Ser Ser Ile Glu Lys Thr Ile Ser Lys Ala
225                 230                 235                 240

Lys Gly Gln Pro Arg Glu Pro Gln Val Tyr Thr Leu Pro Pro Ser Gln
                245                 250                 255

Glu Glu Met Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
    290                 295                 300

Phe Phe Leu Tyr Ser Arg Leu Thr Val Asp Lys Ser Arg Trp Gln Glu
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Leu Gly Lys
            340                 345

<210> SEQ ID NO 90
<211> LENGTH: 448

```
<212> TYPE: PRT
<213> ORGANISM: Artificial Sequence
<220> FEATURE:
<223> OTHER INFORMATION: Synthetic polypeptide: HC_ Y1238-IgG1.3f

<400> SEQUENCE: 90
```

| | | | | | | | | | | | | | | | |
|---|---|---|---|---|---|---|---|---|---|---|---|---|---|---|---|
| Gln | Val | Gln | Leu | Gln | Gln | Ser | Gly | Ala | Glu | Leu | Val | Arg | Pro | Gly | Thr |
| 1 | | | | 5 | | | | | 10 | | | | | 15 | |
| Ser | Val | Lys | Val | Ser | Cys | Lys | Ala | Ser | Gly | Tyr | Ala | Phe | Thr | Asn | Tyr |
| | | | 20 | | | | | 25 | | | | | 30 | | |
| Leu | Ile | Glu | Trp | Val | Lys | Gln | Arg | Pro | Gly | Gln | Gly | Leu | Glu | Trp | Ile |
| | | | 35 | | | | | 40 | | | | | 45 | | |
| Gly | Val | Ile | Asn | Pro | Gly | Ser | Gly | Gly | Thr | Asn | Tyr | Asn | Glu | Lys | Phe |
| | 50 | | | | | 55 | | | | | 60 | | | | |
| Lys | Gly | Lys | Ala | Thr | Leu | Thr | Ala | Asp | Lys | Ser | Ser | Thr | Ala | Tyr |
| 65 | | | | | 70 | | | | | 75 | | | | | 80 |
| Met | Gln | Leu | Ser | Ser | Leu | Thr | Ser | Asp | Asp | Ser | Ala | Val | Tyr | Phe | Cys |
| | | | | 85 | | | | | 90 | | | | | 95 | |
| Ala | Arg | Ser | Gln | Leu | Gly | Arg | Arg | Phe | Asp | Tyr | Trp | Gly | Gln | Gly | Thr |
| | | | 100 | | | | | 105 | | | | | 110 | | |
| Thr | Leu | Thr | Val | Ser | Ser | Ala | Ser | Thr | Lys | Gly | Pro | Ser | Val | Phe | Pro |
| | | | 115 | | | | | 120 | | | | | 125 | | |
| Leu | Ala | Pro | Ser | Ser | Lys | Ser | Thr | Ser | Gly | Gly | Thr | Ala | Ala | Leu | Gly |
| | 130 | | | | | 135 | | | | | 140 | | | | |
| Cys | Leu | Val | Lys | Asp | Tyr | Phe | Pro | Glu | Pro | Val | Thr | Val | Ser | Trp | Asn |
| 145 | | | | | 150 | | | | | 155 | | | | | 160 |
| Ser | Gly | Ala | Leu | Thr | Ser | Gly | Val | His | Thr | Phe | Pro | Ala | Val | Leu | Gln |
| | | | | 165 | | | | | 170 | | | | | 175 | |
| Ser | Ser | Gly | Leu | Tyr | Ser | Leu | Ser | Ser | Val | Val | Thr | Val | Pro | Ser | Ser |
| | | | 180 | | | | | 185 | | | | | 190 | | |
| Ser | Leu | Gly | Thr | Gln | Thr | Tyr | Ile | Cys | Asn | Val | Asn | His | Lys | Pro | Ser |
| | | | 195 | | | | | 200 | | | | | 205 | | |
| Asn | Thr | Lys | Val | Asp | Lys | Arg | Val | Glu | Pro | Lys | Ser | Cys | Asp | Lys | Thr |
| | 210 | | | | | 215 | | | | | 220 | | | | |
| His | Thr | Cys | Pro | Pro | Cys | Pro | Ala | Pro | Glu | Ala | Glu | Gly | Ala | Pro | Ser |
| 225 | | | | | 230 | | | | | 235 | | | | | 240 |
| Val | Phe | Leu | Phe | Pro | Pro | Lys | Pro | Lys | Asp | Thr | Leu | Met | Ile | Ser | Arg |
| | | | | 245 | | | | | 250 | | | | | 255 | |
| Thr | Pro | Glu | Val | Thr | Cys | Val | Val | Val | Asp | Val | Ser | His | Glu | Asp | Pro |
| | | | 260 | | | | | 265 | | | | | 270 | | |
| Glu | Val | Lys | Phe | Asn | Trp | Tyr | Val | Asp | Gly | Val | Glu | Val | His | Asn | Ala |
| | | | 275 | | | | | 280 | | | | | 285 | | |
| Lys | Thr | Lys | Pro | Arg | Glu | Glu | Gln | Tyr | Asn | Ser | Thr | Tyr | Arg | Val | Val |
| | 290 | | | | | 295 | | | | | 300 | | | | |
| Ser | Val | Leu | Thr | Val | Leu | His | Gln | Asp | Trp | Leu | Asn | Gly | Lys | Glu | Tyr |
| 305 | | | | | 310 | | | | | 315 | | | | | 320 |
| Lys | Cys | Lys | Val | Ser | Asn | Lys | Ala | Leu | Pro | Ala | Pro | Ile | Glu | Lys | Thr |
| | | | | 325 | | | | | 330 | | | | | 335 | |
| Ile | Ser | Lys | Ala | Lys | Gly | Gln | Pro | Arg | Glu | Pro | Gln | Val | Tyr | Thr | Leu |
| | | | 340 | | | | | 345 | | | | | 350 | | |
| Pro | Pro | Ser | Arg | Glu | Glu | Met | Thr | Lys | Asn | Gln | Val | Ser | Leu | Thr | Cys |
| | | | 355 | | | | | 360 | | | | | 365 | | |
| Leu | Val | Lys | Gly | Phe | Tyr | Pro | Ser | Asp | Ile | Ala | Val | Glu | Trp | Glu | Ser |
| | 370 | | | | | 375 | | | | | 380 | | | | |

```
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445
```

<210> SEQ ID NO 91
<211> LENGTH: 448
<212> TYPE: PRT
<213> ORGANISM: Artificial Sequence
<220> FEATURE:
<223> OTHER INFORMATION: Synthetic polypeptide: HC_ Y1238-CTza

<400> SEQUENCE: 91

```
Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asn Pro Gly Ser Gly Gly Thr Asn Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Asp Asp Ser Ala Val Tyr Phe Cys
                85                  90                  95

Ala Arg Ser Gln Leu Gly Arg Arg Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Ser Pro Pro Ser Pro Ala Pro Glu Leu Leu Gly Gly Ser Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300
```

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Arg Asp Glu Leu Thr Lys Asn Gln Val Ser Leu Thr Cys
    355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 92
<211> LENGTH: 448
<212> TYPE: PRT
<213> ORGANISM: Artificial Sequence
<220> FEATURE:
<223> OTHER INFORMATION: Synthetic polypeptide: HC_ Y1238-N297A

<400> SEQUENCE: 92

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asn Pro Gly Ser Gly Gly Thr Asn Tyr Asn Glu Lys Phe
50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Asp Asp Ser Ala Val Tyr Phe Cys
                85                  90                  95

Ala Arg Ser Gln Leu Gly Arg Arg Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
        245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 93
<211> LENGTH: 448
<212> TYPE: PRT
<213> ORGANISM: Artificial Sequence
<220> FEATURE:
<223> OTHER INFORMATION: Synthetic polypeptide: HC_ Y1238-P238K

<400> SEQUENCE: 93

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asn Pro Gly Ser Gly Gly Thr Asn Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Asp Asp Ser Ala Val Tyr Phe Cys
                85                  90                  95

Ala Arg Ser Gln Leu Gly Arg Arg Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
            210                 215                 220

His Thr Cys Pro Pro Cys Pro Ala Pro Glu Leu Leu Gly Gly Lys Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 94
<211> LENGTH: 214
<212> TYPE: PRT
<213> ORGANISM: Artificial Sequence
<220> FEATURE:
<223> OTHER INFORMATION: Synthetic polypeptide: LC_Y1238

<400> SEQUENCE: 94

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Arg Thr Gly
            20                  25                  30

Val Ala Trp Tyr Gln Gln Lys Pro Gly Gln Ser Pro Lys Leu Leu Ile
            35                  40                  45

Tyr Ser Ala Ser Tyr Arg Asn Thr Gly Val Pro Asp Arg Phe Thr Gly
        50                  55                  60

```
Ser Arg Ser Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Pro Pro Tyr
                 85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 95
<211> LENGTH: 449
<212> TYPE: PRT
<213> ORGANISM: Artificial Sequence
<220> FEATURE:
<223> OTHER INFORMATION: Synthetic polypeptide: HC_BI-mAb-B

<400> SEQUENCE: 95

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
             20                  25                  30

Gly Met His Trp Val Arg Gln Ala Pro Gly Lys Gly Leu Glu Trp Val
         35                  40                  45

Ala Tyr Ile Ser Ser Gly Asn Arg Ile Ile Tyr Tyr Ala Asp Thr Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gln Asp Gly Tyr Arg Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

```
Ser Asn Thr Lys Val Asp Lys Arg Val Glu Pro Lys Ser Cys Asp Lys
        210                 215                 220

Thr His Thr Cys Pro Pro Cys Pro Ala Pro Glu Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
        435                 440                 445
Lys

<210> SEQ ID NO 96
<211> LENGTH: 220
<212> TYPE: PRT
<213> ORGANISM: Artificial Sequence
<220> FEATURE:
<223> OTHER INFORMATION: Synthetic polypeptide: LC_BI-mAb-B

<400> SEQUENCE: 96

Asp Ile Val Met Thr Gln Ser Pro Asp Ser Leu Ala Val Ser Leu Gly
1               5                   10                  15

Glu Lys Val Thr Ile Asn Cys Lys Ser Ser Gln Ser Leu Leu Asn Ser
            20                  25                  30

Gly Asn Gln Lys Asn Tyr Leu Thr Trp His Gln Gln Lys Pro Gly Gln
        35                  40                  45

Pro Pro Lys Leu Leu Ile Tyr Trp Thr Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Thr Tyr Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
```

```
                115                 120                 125
Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
                210                 215                 220

<210> SEQ ID NO 97
<211> LENGTH: 7
<212> TYPE: PRT
<213> ORGANISM: Artificial Sequence
<220> FEATURE:
<223> OTHER INFORMATION: Synthetic peptide: Linker

<400> SEQUENCE: 97

Ala Ser Thr Ser Gly Pro Ser
1               5

<210> SEQ ID NO 98
<211> LENGTH: 231
<212> TYPE: PRT
<213> ORGANISM: Artificial Sequence
<220> FEATURE:
<223> OTHER INFORMATION: Synthetic polypeptide: Fc domain IgG1a-P238K-
      (-C-term Lys)

<400> SEQUENCE: 98

Glu Pro Lys Ser Cys Asp Lys Thr His Thr Cys Pro Pro Cys Pro Ala
1               5                   10                  15

Pro Glu Leu Leu Gly Gly Lys Ser Val Phe Leu Phe Pro Pro Lys Pro
                20                  25                  30

Lys Asp Thr Leu Met Ile Ser Arg Thr Pro Glu Val Thr Cys Val Val
                35                  40                  45

Val Asp Val Ser His Glu Asp Pro Glu Val Lys Phe Asn Trp Tyr Val
            50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
                115                 120                 125

Arg Glu Pro Gln Val Tyr Thr Leu Pro Pro Ser Arg Asp Glu Leu Thr
                130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190
```

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly
225                 230

<210> SEQ ID NO 99
<211> LENGTH: 329
<212> TYPE: PRT
<213> ORGANISM: Artificial Sequence
<220> FEATURE:
<223> OTHER INFORMATION: Synthetic polypeptide: CH1- IgG1a-P238K
      (-C-term Lys)

<400> SEQUENCE: 99

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Lys Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr

```
305                 310                 315                 320
Gln Lys Ser Leu Ser Leu Ser Pro Gly
                325

<210> SEQ ID NO 100
<211> LENGTH: 231
<212> TYPE: PRT
<213> ORGANISM: Artificial Sequence
<220> FEATURE:
<223> OTHER INFORMATION: Synthetic polypeptide: Fc domain IgG1f-P238K
      (-C-term Lys)

<400> SEQUENCE: 100

Glu Pro Lys Ser Cys Asp Lys Thr His Thr Cys Pro Pro Cys Pro Ala
1               5                   10                  15

Pro Glu Leu Leu Gly Gly Lys Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 101
<211> LENGTH: 329
<212> TYPE: PRT
<213> ORGANISM: Artificial Sequence
<220> FEATURE:
<223> OTHER INFORMATION: Synthetic polypeptide: 5F11-CH1- IgG1f-P238K
      (-C-term Lys)

<400> SEQUENCE: 101

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
```

```
                35                  40                  45
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Lys Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 102
<211> LENGTH: 231
<212> TYPE: PRT
<213> ORGANISM: Artificial Sequence
<220> FEATURE:
<223> OTHER INFORMATION: Synthetic polypeptide: Fc domain IgG1a-N297A
      (-C-term Lys)

<400> SEQUENCE: 102

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
                35                  40                  45

Val Asp Val Ser His Glu Asp Pro Glu Val Lys Phe Asn Trp Tyr Val
                50                  55                  60
```

```
Asp Gly Val Glu Val His Asn Ala Lys Thr Lys Pro Arg Glu Glu Gln
65                  70                  75                  80

Tyr Ala Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly
225                 230

<210> SEQ ID NO 103
<211> LENGTH: 329
<212> TYPE: PRT
<213> ORGANISM: Artificial Sequence
<220> FEATURE:
<223> OTHER INFORMATION: Synthetic polypeptide: 5F11-CH1- IgG1a-N297A
      (-C-term Lys)

<400> SEQUENCE: 103

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190
```

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 104
<211> LENGTH: 231
<212> TYPE: PRT
<213> ORGANISM: Artificial Sequence
<220> FEATURE:
<223> OTHER INFORMATION: Synthetic polypeptide: Fc domain IgG1f-N297A
      (-C-term Lys)

<400> SEQUENCE: 104

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Ala Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys

```
            210                 215                 220
Ser Leu Ser Leu Ser Pro Gly
225                 230

<210> SEQ ID NO 105
<211> LENGTH: 329
<212> TYPE: PRT
<213> ORGANISM: Artificial Sequence
<220> FEATURE:
<223> OTHER INFORMATION: Synthetic polypeptide: 5F11-CH1- IgG1f-N297A
      (-C-term Lys)

<400> SEQUENCE: 105

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 106
<211> LENGTH: 446
<212> TYPE: PRT
<213> ORGANISM: Artificial Sequence
<220> FEATURE:
<223> OTHER INFORMATION: Synthetic polypeptide: HC_5F11-45-P238K
(-C-TERM LYS)

<400> SEQUENCE: 106

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Leu
            20                  25                  30

Ser Met His Trp Val Arg Gln Ala Pro Gly Gln Gly Leu Glu Trp Met
        35                  40                  45

Gly Tyr Ile Thr Pro Ser Ser Gly Tyr Thr Ala Tyr Asn Gln Lys Phe
    50                  55                  60

Lys Gly Lys Thr Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ile Leu Gln Arg Gly Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Lys Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365
```

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly
                435                 440                 445

<210> SEQ ID NO 107
<211> LENGTH: 446
<212> TYPE: PRT
<213> ORGANISM: Artificial Sequence
<220> FEATURE:
<223> OTHER INFORMATION: Synthetic polypeptide: HC_5F11-45-P238K
      (-C-TERM LYS)

<400> SEQUENCE: 107

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Leu
            20                  25                  30

Ser Met His Trp Val Arg Gln Ala Pro Gly Gln Gly Leu Glu Trp Met
        35                  40                  45

Gly Tyr Ile Thr Pro Ser Ser Gly Tyr Thr Ala Tyr Asn Gln Lys Phe
    50                  55                  60

Lys Gly Lys Thr Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ile Leu Gln Arg Gly Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Lys Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys

```
                    275                 280                 285
Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
                435                 440                 445

<210> SEQ ID NO 108
<211> LENGTH: 447
<212> TYPE: PRT
<213> ORGANISM: Artificial Sequence
<220> FEATURE:
<223> OTHER INFORMATION: Synthetic polypeptide: HC_5F11-45-P238K

<400> SEQUENCE: 108

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Leu
            20                  25                  30

Ser Met His Trp Val Arg Gln Ala Pro Gly Gln Gly Leu Glu Trp Met
        35                  40                  45

Gly Tyr Ile Thr Pro Ser Ser Gly Tyr Thr Ala Tyr Asn Gln Lys Phe
    50                  55                  60

Lys Gly Lys Thr Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ile Leu Gln Arg Gly Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
```

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Lys Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 109
<211> LENGTH: 446
<212> TYPE: PRT
<213> ORGANISM: Artificial Sequence
<220> FEATURE:
<223> OTHER INFORMATION: Synthetic polypeptide: HC_5F11-45-N297A
     (-C-TERM LYS)

<400> SEQUENCE: 109

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Leu
            20                  25                  30

Ser Met His Trp Val Arg Gln Ala Pro Gly Gln Gly Leu Glu Trp Met
        35                  40                  45

Gly Tyr Ile Thr Pro Ser Ser Gly Tyr Thr Ala Tyr Asn Gln Lys Phe
    50                  55                  60

Lys Gly Lys Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ile Leu Gln Arg Gly Ala Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 110
<211> LENGTH: 447
<212> TYPE: PRT
<213> ORGANISM: Artificial Sequence
<220> FEATURE:
<223> OTHER INFORMATION: Synthetic polypeptide: HC_5F11-45-N297A

<400> SEQUENCE: 110

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Leu
            20                  25                  30

-continued

Ser Met His Trp Val Arg Gln Ala Pro Gly Gln Gly Leu Glu Trp Met
         35                  40                  45
Gly Tyr Ile Thr Pro Ser Ser Gly Tyr Thr Ala Tyr Asn Gln Lys Phe
 50                  55                  60
Lys Gly Lys Thr Thr Leu Thr Ala Asp Lys Ser Thr Ser Thr Ala Tyr
 65                  70                  75                  80
Met Glu Leu Ser Ser Leu Arg Ser Glu Asp Thr Ala Val Tyr Tyr Cys
             85                  90                  95
Ala Arg Leu Ile Leu Gln Arg Gly Ala Tyr Trp Gly Gln Gly Thr Leu
             100                 105                 110
Val Thr Val Ser Ser Ala Ser Thr Lys Gly Pro Ser Val Phe Pro Leu
         115                 120                 125
Ala Pro Ser Ser Lys Ser Thr Ser Gly Gly Thr Ala Ala Leu Gly Cys
     130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
             165                 170                 175
Ser Gly Leu Tyr Ser Leu Ser Ser Val Val Thr Val Pro Ser Ser Ser
         180                 185                 190
Leu Gly Thr Gln Thr Tyr Ile Cys Asn Val Asn His Lys Pro Ser Asn
     195                 200                 205
Thr Lys Val Asp Lys Arg Val Glu Pro Lys Ser Cys Asp Lys Thr His
 210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
             245                 250                 255
Pro Glu Val Thr Cys Val Val Val Asp Val Ser His Glu Asp Pro Glu
         260                 265                 270
Val Lys Phe Asn Trp Tyr Val Asp Gly Val Glu Val His Asn Ala Lys
     275                 280                 285
Thr Lys Pro Arg Glu Glu Gln Tyr Ala Ser Thr Tyr Arg Val Val Ser
 290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
             325                 330                 335
Ser Lys Ala Lys Gly Gln Pro Arg Glu Pro Gln Val Tyr Thr Leu Pro
         340                 345                 350
Pro Ser Arg Asp Glu Leu Thr Lys Asn Gln Val Ser Leu Thr Cys Leu
     355                 360                 365
Val Lys Gly Phe Tyr Pro Ser Asp Ile Ala Val Glu Trp Glu Ser Asn
 370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
             405                 410                 415
Trp Gln Gln Gly Asn Val Phe Ser Cys Ser Val Met His Glu Ala Leu
         420                 425                 430
His Asn His Tyr Thr Gln Lys Ser Leu Ser Leu Ser Pro Gly Lys
     435                 440                 445

<210> SEQ ID NO 111
<211> LENGTH: 446
<212> TYPE: PRT
<213> ORGANISM: Artificial Sequence
<220> FEATURE:
<223> OTHER INFORMATION: Synthetic polypeptide: HC_5F11-45-N297A (-C-TERM LYS)

<400> SEQUENCE: 111

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Leu
            20                  25                  30

Ser Met His Trp Val Arg Gln Ala Pro Gly Gln Gly Leu Glu Trp Met
        35                  40                  45

Gly Tyr Ile Thr Pro Ser Ser Gly Tyr Thr Ala Tyr Asn Gln Lys Phe
    50                  55                  60

Lys Gly Lys Thr Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ile Leu Gln Arg Gly Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365
```

```
Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
            435                 440                 445

<210> SEQ ID NO 112
<211> LENGTH: 232
<212> TYPE: PRT
<213> ORGANISM: Artificial Sequence
<220> FEATURE:
<223> OTHER INFORMATION: Synthetic polypeptide: Fc domain consensus
<220> FEATURE:
<221> NAME/KEY: MOD_RES
<222> LOCATION: (23)..(23)
<223> OTHER INFORMATION: Pro or Lys
<220> FEATURE:
<221> NAME/KEY: MOD_RES
<222> LOCATION: (82)..(82)
<223> OTHER INFORMATION: Asn or Ala
<220> FEATURE:
<221> NAME/KEY: MOD_RES
<222> LOCATION: (141)..(141)
<223> OTHER INFORMATION: Asp or Glu
<220> FEATURE:
<221> NAME/KEY: MOD_RES
<222> LOCATION: (143)..(143)
<223> OTHER INFORMATION: Leu or Met
<220> FEATURE:
<221> NAME/KEY: MOD_RES
<222> LOCATION: (232)..(232)
<223> OTHER INFORMATION: Lys or absent

<400> SEQUENCE: 112

Glu Pro Lys Ser Cys Asp Lys Thr His Thr Cys Pro Pro Cys Pro Ala
1               5                   10                  15

Pro Glu Leu Leu Gly Gly Xaa Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Xaa Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Xaa Glu Xaa Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
```

```
               180                 185                 190
Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
        210                 215                 220

Ser Leu Ser Leu Ser Pro Gly Xaa
225                 230

<210> SEQ ID NO 113
<211> LENGTH: 351
<212> TYPE: DNA
<213> ORGANISM: Artificial Sequence
<220> FEATURE:
<223> OTHER INFORMATION: Synthetic polynucleotide: 5F11-45 VH

<400> SEQUENCE: 113
caggtgcagc tggtgcagtc tggggctgag gtgaagaagc ctgggtcctc ggtgaaggtc       60
tcctgcaagg cttctggata caccttcact gacttatcga tgcactgggt gcgacaggcc      120
cctggacaag gcttgagtg atgggatac attactccta gcagtggata tactgcgtac        180
aatcagaagt tcaagggcaa gaccacgttg accgcggaca atccacgag cacagcctac       240 atggagctga gcagcctgag atctgaggac acggccgtgt attactgtgc gagattgatc      300
ttacaacggg gagcttactg gggccaggga accctggtca ccgtctcctc a              351

<210> SEQ ID NO 114
<211> LENGTH: 333
<212> TYPE: DNA
<213> ORGANISM: Artificial Sequence
<220> FEATURE:
<223> OTHER INFORMATION: Synthetic polynucleotide: 5F11-45 VL

<400> SEQUENCE: 114
gacatcgtgc tgacccagtc tccagactcc ctggctgtgt ctctgggcga gagggccacc       60
atcaactgca gagccagtaa aaatgttgat agttatggca atagttttat gcactggtac      120
cagcagaaac caggacagcc tcctaagctg ctcatttacc gtgcatccaa cctagaatct      180
ggggtccctg accgattcag tggcagcggg tctgggacag atttcactct caccatcagc      240
agcctgcagg ctgaagatgt ggcagtttat tactgtcagc aaagtaatga ggatcctctc      300
acgtttggcc aggggaccaa gctggagatc aaa                                  333

<210> SEQ ID NO 115
<211> LENGTH: 1338
<212> TYPE: DNA
<213> ORGANISM: Artificial Sequence
<220> FEATURE:
<223> OTHER INFORMATION: Synthetic polynucleotide: 5F11-45-HC (no C-term
      lysine) with P238K

<400> SEQUENCE: 115
caggtgcagc tggtgcagtc tggggctgag gtgaagaagc ctgggtcctc ggtgaaggtc       60
tcctgcaagg cttctggata caccttcact gacttatcga tgcactgggt gcgacaggcc      120
cctggacaag gcttgagtg atgggatac attactccta gcagtggata tactgcgtac        180
aatcagaagt tcaagggcaa gaccacgttg accgcggaca atccacgag cacagcctac       240 atggagctga gcagcctgag atctgaggac acggccgtgt attactgtgc gagattgatc      300
ttacaacggg gagcttactg gggccaggga accctggtca ccgtctcctc agctagcacc      360
aagggcccat cggtcttccc cctggcaccc tcctccaaga gcacctctgg gggcacagcg      420
```

```
gccctgggct gcctggtcaa ggactacttc cccgaaccgg tgacggtgtc gtggaactca      480
ggcgccctga ccagcggcgt gcacaccttc ccggccgtcc tacagtcctc aggactctac      540
tccctcagca gcgtggtgac cgtgccctcc agcagcttgg gcacccagac ctacatctgc      600
aacgtgaatc acaagcccag caacaccaag gtggacaaga gagttgagcc caaatcttgt      660
gacaaaactc acacatgccc accgtgccca gcacctgaac tcctgggggg aaagtcagtc      720
ttcctcttcc cccaaaaacc caaggacacc ctcatgatct cccggacccc tgaggtcaca      780
tgcgtggtgg tggacgtgag ccacgaagac cctgaggtca agttcaactg gtacgtggac      840
ggcgtggagg tgcataatgc caagacaaag ccgcgggagg agcagtacaa cagcacgtac      900
cgtgtggtca gcgtcctcac cgtcctgcac caggactggc tgaatggcaa ggagtacaag      960
tgcaaggtct ccaacaaagc cctcccagcc cccatcgaga aaccatctc caaagccaaa      1020 gggcagcccc gagaaccaca ggtgtacacc ctgcccccat cccgggatga gctgaccaag      1080
aaccaggtca gcctgacctg cctggtcaaa ggcttctatc ccagcgacat cgccgtggag      1140
tgggagagca atgggcagcc ggagaacaac tacaagacca cgcctcccgt gctggactcc      1200
gacggctcct tcttcctcta cagcaagctc accgtggaca agagcaggtg gcagcagggg      1260
aacgtcttct catgctccgt gatgcatgag gctctgcaca accactacac gcagaagagc      1320
ctctccctgt ctccgggt                                                    1338

<210> SEQ ID NO 116
<211> LENGTH: 654
<212> TYPE: DNA
<213> ORGANISM: Artificial Sequence
<220> FEATURE:
<223> OTHER INFORMATION: Synthetic polynucleotide: 5F11-45-LC

<400> SEQUENCE: 116
gacatcgtgc tgacccagtc tccagactcc ctggctgtgt ctctgggcga gagggccacc       60
atcaactgca gagccagtaa aaatgttgat agttatggca atagttttat gcactggtac      120
cagcagaaac caggacagcc tcctaagctg ctcatttacc gtgcatccaa cctagaatct      180
ggggtccctg accgattcag tggcagcggg tctgggacag atttcactct caccatcagc      240
agcctgcagg ctgaagatgt ggcagtttat tactgtcagc aaagtaatga ggatcctctc      300
acgtttggcc aggggaccaa gctggagatc aaacgtacgg tggctgcacc atctgtcttc      360
atcttcccgc catctgatga gcagttgaaa tctggaactg cctctgttgt gtgcctgctg      420
aataacttct atcccagaga ggccaaagta cagtggaagg tggataacgc cctccaatcg      480
ggtaactccc aggagagtgt cacagagcag gacagcaagg acagcaccta cagcctcagc      540
agcaccctga cgctgagcaa agcagactac gagaaacaca aagtctacgc ctgcgaagtc      600
acccatcagg gcctgagctc gcccgtcaca aagagcttca caggggaga gtgt            654

<210> SEQ ID NO 117
<211> LENGTH: 1389
<212> TYPE: DNA
<213> ORGANISM: Artificial Sequence
<220> FEATURE:
<223> OTHER INFORMATION: Synthetic polynucleotide: 5F11-45-HC with
      signal peptide (no C-term lysine) with P238K

<400> SEQUENCE: 117
atgagggctt ggatcttctt tctgctctgc ctggccggga gagcgctcgc acaggtgcag       60
ctggtgcagt ctggggctga ggtgaagaag cctgggtcct cggtgaaggt ctcctgcaag      120
```

```
gcttctggat acaccttcac tgacttatcg atgcactggg tgcgacaggc ccctggacaa      180
gggcttgagt ggatgggata cattactcct agcagtggat atactgcgta caatcagaag      240
ttcaagggca agaccacgtt gaccgcggac aaatccacga gcacagccta catggagctg      300
agcagcctga gatctgagga cacggccgtg tattactgtg cgagattgat cttacaacgg      360
ggagcttact ggggccaggg aaccctggtc accgtctcct cagctagcac aagggccca       420 tcggtcttcc ccctggcacc ctcctccaag agcacctctg gggcacagc ggccctgggc       480 tgcctggtca aggactactt ccccgaaccg gtgacggtgt cgtggaactc aggcgccctg      540
accagcggcg tgcacacctt cccggccgtc ctacagtcct caggactcta ctccctcagc      600
agcgtggtga ccgtgccctc agcagcttg gcacccaga cctacatctg caacgtgaat        660
cacaagccca gcaacaccaa ggtggacaag agagttgagc ccaaatcttg tgacaaaact      720
cacacatgcc caccgtgccc agcacctgaa ctcctggggg gaaagtcagt cttcctcttc      780
cccccaaaac ccaaggacac cctcatgatc tcccggaccc ctgaggtcac atgcgtggtg      840
gtggacgtga gccacgaaga ccctgaggtc aagttcaact ggtacgtgga cggcgtggag      900
gtgcataatg ccaagacaaa gccgcgggag gagcagtaca acagcacgta ccgtgtggtc      960
agcgtcctca ccgtcctgca ccaggactgg ctgaatggca aggagtacaa gtgcaaggtc     1020
tccaacaaag ccctcccagc cccatcgag aaaaccatct ccaaagccaa agggcagccc      1080
cgagaaccac aggtgtacac cctgccccca tcccgggatg agctgaccaa gaaccaggtc     1140
agcctgacct gcctggtcaa aggcttctat cccagcgaca tcgccgtgga gtgggagagc     1200
aatgggcagc cggagaacaa ctacaagacc acgcctcccg tgctggactc cgacggctcc     1260
ttcttcctct acagcaagct caccgtggac aagagcaggt ggcagcaggg gaacgtcttc     1320
tcatgctccg tgatgcatga ggctctgcac aaccactaca cgcagaagag cctctccctg     1380
tctccgggt                                                            1389
```

<210> SEQ ID NO 118
<211> LENGTH: 705
<212> TYPE: DNA
<213> ORGANISM: Artificial Sequence
<220> FEATURE:
<223> OTHER INFORMATION: Synthetic polynucleotide: 5F11-45-LC with
      signal peptide (no C-term lysine)

<400> SEQUENCE: 118

```
atgagggctt ggatcttctt tctgctctgc ctggccgggc gcgccttggc cgacatcgtg       60
ctgacccagt ctccagactc cctggctgtg tctctgggcg agagggccac catcaactgc      120
agagccagta aaaatgttga tagttatggc aatagtttta tgcactggta ccagcagaaa      180
ccaggacagc ctcctaagct gctcatttac cgtgcatcca acctagaatc tggggtccct      240
gaccgattca gtggcagcgg gtctgggaca gatttcactc tcaccatcag cagcctgcag      300
gctgaagatg tggcagttta ttactgtcag caaagtaatg aggatcctct cacgtttggc      360
caggggacca agctggagat caaacgtacg gtggctgcac catctgtctt catcttcccg      420
ccatctgatg agcagttgaa atctggaact gcctctgttg tgtgcctgct gaataacttc      480
tatcccagag aggccaaagt acagtggaag gtggataacg ccctccaatc gggtaactcc      540
caggagagtg tcacagagca ggacagcaag gacagcacct acagcctcag cagcaccctg      600
acgctgagca aagcagacta cgagaaacac aaagtctacg cctgcgaagt cacccatcag      660
ggcctgagct cgcccgtcac aaagagcttc aacaggggag agtgt                      705
```

```
<210> SEQ ID NO 119
<211> LENGTH: 17
<212> TYPE: PRT
<213> ORGANISM: Artificial Sequence
<220> FEATURE:
<223> OTHER INFORMATION: Synthetic peptide: Signal Peptide

<400> SEQUENCE: 119

Met Arg Ala Trp Ile Phe Phe Leu Leu Cys Leu Ala Gly Arg Ala Leu
1               5                   10                  15

Ala
```